(12) United States Patent
Azimioara et al.

(10) Patent No.: US 8,575,168 B2
(45) Date of Patent: Nov. 5, 2013

(54) COMPOUNDS AND COMPOSITIONS AS MODULATORS OF GPR119 ACTIVITY

(75) Inventors: Mihai Azimioara, La Jolla, CA (US); Christopher Cow, Poway, CA (US); Robert Epple, San Diego, CA (US); Gerald Lelais, San Diego, CA (US); John Mecom, San Diego, CA (US); Victor Nikulin, Carlsbad, CA (US)

(73) Assignee: IRM LLC, Hamilton (BM)

( * ) Notice: Subject to any disclaimer, the term of this patent is extended or adjusted under 35 U.S.C. 154(b) by 362 days.

(21) Appl. No.: 12/896,735

(22) Filed: Oct. 1, 2010

(65) Prior Publication Data
US 2011/0245220 A1    Oct. 6, 2011

Related U.S. Application Data

(60) Provisional application No. 61/250,424, filed on Oct. 9, 2009, provisional application No. 61/365,112, filed on Jul. 16, 2010.

(51) Int. Cl.
*A61K 31/497* (2006.01)
*A61K 31/445* (2006.01)
*C07D 239/42* (2006.01)
*C07D 239/00* (2006.01)
*C07D 241/00* (2006.01)
*C07D 401/00* (2006.01)
*C07D 405/00* (2006.01)

(52) U.S. Cl.
USPC ............ 514/252.1; 514/252.12; 514/252.13; 514/256; 514/315; 514/316; 544/242; 544/336; 544/360; 546/187

(58) Field of Classification Search
USPC ........ 546/187; 544/242, 336, 360; 514/252.1, 514/252, 12, 252.13, 256, 315, 316
See application file for complete search history.

(56) References Cited

FOREIGN PATENT DOCUMENTS

| WO | WO2009038974 | 3/2009 |
| WO | WO2009126535 | 10/2009 |

OTHER PUBLICATIONS

Wu, et al., "2,5-Disubstituted pyridines as potent GPR118 agonists", Bioorganic & Medicinal Chemistry Letters, Apr. 15, 2010, pp. 2577-2581, vol. 20, No. 8, Elsevier Ltd.

*Primary Examiner* — Shengjun Wang
(74) *Attorney, Agent, or Firm* — Chihang Amy Smith; Genomics Institute of the Novartis Research Foundation

(57) ABSTRACT

The invention provides compounds, pharmaceutical compositions comprising such compounds and methods of using such compounds to treat or prevent diseases or disorders associated with the activity of GPR119.

13 Claims, No Drawings

COMPOUNDS AND COMPOSITIONS AS MODULATORS OF GPR119 ACTIVITY

CROSS-REFERENCE TO RELATED APPLICATIONS

This application claims the benefit of priority to U.S. Provisional Patent Application No. 61/250,424, filed 9 Oct. 2009 and U.S. Provisional Patent Application No. 61/365,112, filed 16 Jul. 2010. The full disclosures of these applications are incorporated herein by reference in their entirety and for all purposes.

BACKGROUND OF THE INVENTION

1. Field of the Invention

The invention provides compounds, pharmaceutical compositions comprising such compounds and methods of using such compounds to treat or prevent diseases or disorders associated with the activity of GPR119.

2. Background

GPR119 is a G-protein coupled receptor (GPCR) that is mainly expressed in the pancreas, small intestine, colon and adipose tissue. The expression profile of the human GPR119 receptor indicates its potential utility as a target for the treatment of obesity and diabetes. The novel compounds of this invention modulate the activity of GPR119 and are, therefore, expected to be useful in the treatment of GPR119-associated diseases or disorders such as, but not limited to, diabetes, obesity and associated metabolic disorders.

SUMMARY OF THE INVENTION

In one aspect, the present invention provides a compound of Formula I:

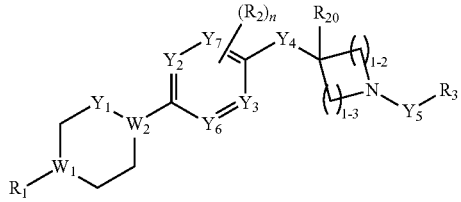

in which:

n is selected from 0, 1, 2, 3 and 4;

$R_1$ is selected from $-X_1S(O)_{0-2}X_2R_{4a}$, $-X_1C(O)OX_2R_{4a}$, $-X_1C(O)X_2R_{4a}$, $-X_1S(O)_{0-2}X_2OR_{4a}$, $-X_1C(O)NR_{4b}X_2R_{4a}$, $-X_1S(O)_{0-2}X_2C(O)R_{4a}$, $-X_1S(O)_{0-2}X_2C(O)OR_{4a}$, $-X_1S(O)_{0-2}X_2OC(O)R_{4a}$ and $-X_1S(O)_{0-2}NR_{4a}R_{4b}$; wherein $X_1$ is selected from a bond, O, $NR_{5a}R_{5b}$ and $C_{1-4}$alkylene; $X_2$ is selected from a bond and $C_{1-4}$alkylene; $R_{4a}$ is selected from hydrogen, halo, hydroxy, $C_{1-6}$alkyl, halo-substituted-$C_{1-6}$alkyl, hydroxy-substituted-$C_{1-6}$alkyl, $C_{2-6}$alkenyl, $C_{6-10}$aryl, heteroaryl, $C_{3-8}$heterocycloalkyl and $C_{3-8}$cycloalkyl; wherein said aryl, heteroaryl, cycloalkyl and heterocycloalkyl of $R_{4a}$ is optionally substituted with 1 to 3 radicals independently selected from hydroxy, halo, $C_{1-6}$alkyl, halo-substituted-$C_{1-6}$alkyl, hydroxy-substituted-$C_{1-6}$alkyl, cyano-substituted-$C_{1-6}$alkyl, $C_{1-6}$alkoxy, halo-substituted-$C_{1-6}$alkoxy, $C_{6-10}$aryl-$C_{1-4}$alkoxy and $-X_3C(O)OX_4R_{5c}$; wherein $R_{4b}$ is selected from hydrogen and $C_{1-6}$alkyl; and $R_{5a}$ and $R_{5b}$ are independently selected from hydrogen and $C_{1-6}$alkyl; wherein $X_3$ and $X_4$ are independently selected from a bond and $C_{1-4}$alkylene; $R_{5c}$ is selected from hydrogen and $C_{1-6}$alkyl;

$R_2$ is independently selected from hydrogen, halo, hydroxy, $C_{1-6}$alkyl, halo-substituted-$C_{1-6}$alkyl, hydroxy-substituted-$C_{1-6}$alkyl, $C_{1-6}$alkoxy, halo-substituted-$C_{1-6}$alkoxy, $-C(O)R_6$, and $-C(O)OR_6$; wherein $R_6$ is selected from hydrogen and $C_{1-6}$alkyl;

$R_{20}$ is selected from hydrogen and methyl;

$W_1$ and $W_2$ are independently selected from $CR_7$ and N; wherein $R_7$ is selected from hydrogen, halo, cyano, $C_{1-6}$alkyl and $-C(O)OR_8$; wherein $R_8$ is selected from hydrogen and $C_{1-6}$alkyl;

$Y_1$ is selected from $CH_2$ and $C(O)$; or $Y_1$ and $W_2$ taken together can form a double bond where $W_2$ is C and $Y_1$ is CH;

$Y_2$, $Y_3$, $Y_6$ and $Y_7$ are independently selected from N and $CR_9$, where at least two of $Y_2$, $Y_3$, $Y_6$ and $Y_7$ are $CR_9$; where $R_9$ is selected from hydrogen, halo, hydroxy, $C_{1-6}$alkyl, halo-substituted-$C_{1-6}$alkyl, hydroxy-substituted-$C_{1-6}$alkyl, $C_{1-6}$alkoxy, halo-substituted-$C_{1-6}$alkoxy, $-C(O)R_{10}$, and $-C(O)OR_{10}$; wherein $R_{10}$ is selected from hydrogen and $C_{1-6}$alkyl;

$Y_4$ is selected from O, $CR_{11a}R_{11b}$, $NR_{11a}$ and $S(O)_{0-2}$; each $R_{11a}$ and $R_{11b}$ are independently selected from hydrogen and $C_{1-6}$alkyl; wherein the alkyl of $R_{11a}$ or $R_{11b}$ is optionally substituted with hydroxy, $C_{1-4}$alkyl, halo, halo-substituted-$C_{1-4}$alkyl, $C_{1-4}$alkoxy, halo-substituted-$C_{1-4}$alkoxy and $-NR_{12a}R_{12b}$; wherein $R_{12a}$ and $R_{12b}$ are independently selected from hydrogen and $C_{1-4}$alkyl;

$Y_5$ is selected from $(CR_{13a}R_{13b})_{1-3}$; wherein $R_{13a}$ and $R_{13b}$ are independently selected from hydrogen, halo and $C_{1-6}$alkyl; wherein the alkyl of $R_{13a}$ or $R_{13b}$ is optionally substituted with 1 to 5 substituents independently selected from hydroxy, $C_{1-4}$alkyl, halo, halo-substituted-$C_{1-4}$alkyl, $C_{1-4}$alkoxy and halo-substituted-$C_{1-4}$alkoxy; or $R_{13a}$ and $R_3$ together with the atoms to which they are attached form oxetan-3-yl;

$R_3$ is selected from $C_{6-10}$aryl and heteroaryl; wherein said aryl or heteroaryl of $R_3$ is optionally substituted with 1 to 4 $R_{14}$ radicals; wherein each $R_{14}$ is independently selected from hydrogen, $C_{1-6}$alkyl, halo, cyano, $C_{1-6}$alkoxy, halo-substituted-$C_{1-6}$alkyl, halo-substituted-$C_{1-6}$alkoxy, $C_{3-8}$cycloalkyl and $C_{1-10}$heterocycloalkyl; wherein the alkyl, cycloalkyl, heterocycloalkyl and alkoxy of $R_{14}$ is optionally substituted by 1 to 3 groups selected from $C_{1-6}$alkyl, halo, $C_{1-6}$alkoxy, halo-substituted-$C_{1-6}$alkyl and halo-substituted-$C_{1-6}$alkoxy;

In a second aspect, the present invention provides a pharmaceutical composition which contains a compound of Formula I or a N-oxide derivative, individual isomers and mixture of isomers thereof; or a pharmaceutically acceptable salt thereof, in admixture with one or more suitable excipients.

In a third aspect, the present invention provides a method of treating a disease in an animal in which modulation of GPR119 activity can prevent, inhibit or ameliorate the pathology and/or symptomology of the diseases, which method comprises administering to the animal a therapeutically effective amount of a compound of Formula I or a N-oxide derivative, individual isomers and mixture of isomers thereof, or a pharmaceutically acceptable salt thereof.

In a fourth aspect, the present invention provides the use of a compound of Formula I in the manufacture of a medicament for treating a disease in an animal in which GPR119 activity contributes to the pathology and/or symptomology of the disease.

In a fifth aspect, the present invention provides a process for preparing compounds of Formula I and the N-oxide derivatives, prodrug derivatives, protected derivatives, individual isomers and mixture of isomers thereof, and the pharmaceutically acceptable salts thereof.

DETAILED DESCRIPTION OF THE INVENTION

Definitions

"Alkyl" as a group and as a structural element of other groups, for example halo-substituted-alkyl and alkoxy, can be straight-chained, branched, cyclic or spiro. $C_{1-6}$alkoxy includes methoxy, ethoxy, and the like. Halo-substituted alkyl includes trifluoromethyl, pentafluoroethyl, and the like.

"Aryl" means a monocyclic or fused bicyclic aromatic ring assembly containing six to ten ring carbon atoms. For example, aryl can be phenyl or naphthyl, preferably phenyl.

"Heteroaryl" is as defined as an unsaturated or partially unsaturated ring system containing between 5 and 10 ring members where one or more of the ring members is a heteroatom or divalent group selected from O, N, C(O), $S(O)_{0-2}$ and $NR_{25}$; wherein $R_{25}$ is selected from hydrogen, $C_{1-6}$alkyl and a nitrogen protecting group. For example, heteroaryl includes pyridyl, indolyl, indazolyl, quintoxalinyl, quintolinyl, benzofuranyl, benzopyranyl, benzothiopyranyl, benzo[1,3]dioxole, imidazolyl, benzo-imidazolyl, pyrimidinyl, furanyl, oxazolyl, isoxazolyl, triazolyl, tetrazolyl, pyrazolyl, thienyl, 1H-pyridin-2-onyl, 6-oxo-1,6-dihydro-pyridin-3-yl, etc.

Heteroaryl also includes the N-oxide derivatives, for example, pyridine N-oxide derivatives with the following structure:

"Cycloalkyl" means a saturated or partially unsaturated, monocyclic, fused bicyclic or bridged polycyclic ring assembly containing the number of ring atoms indicated. For example, $C_{3-10}$cycloalkyl includes cyclopropyl, cyclobutyl, cyclopentyl, cyclohexyl, etc.

"Enantiomers" as used in this application for compounds of Formula I, describe each chiral center as labeled R or S according to a system by which its substituents are each assigned a priority, according to the Cahn Ingold Prelog priority rules (CIP), based on atomic number. If the center is oriented so that the lowest-priority of the four is pointed away from a viewer, the viewer will then see two possibilities: if the priority of the remaining three substituents decreases in clockwise direction, it is labeled R (for Rectus), if it decreases in counterclockwise direction, it is S (for Sinister).

"Heterocycloalkyl" means cycloalkyl, as defined in this application, provided that one or more of the ring carbons indicated, are replaced by a moiety selected from —O—, —N=, —NR—, —C(O)—, —S—, —S(O)— or —S(O)$_2$—; wherein R is hydrogen, $C_{1-4}$alkyl or a nitrogen protecting group or any substitution defined by $R_1$-$R_6$ in the Summary of the Invention. For example, $C_{3-8}$heterocycloalkyl as used in this application to describe compounds of the invention includes morpholino, pyrrolidinyl, piperazinyl, piperidinyl, piperidinylone, 1,4-dioxa-8-aza-spiro[4.5]dec-8-yl, 2-oxo-pyrrolidin-1-yl, 2-oxo-piperidin-1-yl, etc.

GPR119 means G protein-coupled receptor 119 (GenBank® Accession No. AAP72125) is also referred to in the literature as RUP3 and GPR116. The term GPR119 as used herein includes the human sequences found in GeneBank accession number AY288416, naturally-occurring allelic variants, mammalian orthologs, and recombinant mutants thereof.

"Halogen" (or halo) preferably represents chloro or fluoro, but can also be bromo or iodo.

"Treat", "treating" and "treatment" refer to a method of alleviating or abating a disease and/or its attendant symptoms.

DESCRIPTION OF THE PREFERRED EMBODIMENTS

The present invention provides compounds, compositions and methods for the treatment of diseases in which modulation of GPR119 activity can prevent, inhibit or ameliorate the pathology and/or symptomology of the diseases, which method comprises administering to the animal a therapeutically effective amount of a compound of Formula I.

In one embodiment, with reference to compounds of Formula I, are compounds of Formula Ia:

in which:

A is selected from $C_{6-10}$aryl and a 5-6 member heteroaryl containing 1 to 3 heteroatoms selected from O, S and N;

n is selected from 0, 1 and 2;

$R_1$ is selected from $S(O)_{0-2}R_{4a}$, —C(O)$X_2R_{4a}$ and —C(O)OX$_2R_{4a}$; wherein $X_2$ is selected from a bond and $C_{1-4}$alkylene; $R_{4a}$ is selected from $C_{1-6}$alkyl, halo-substituted-$C_{1-6}$alkyl, $C_{3-8}$heterocycloalkyl and $C_{6-10}$aryl; wherein said $C_{3-8}$heterocycloalkyl or $C_{6-10}$aryl of $R_{4a}$ is optionally substituted with $C_{1-6}$alkyl;

$R_2$ is halo;

$R_{20}$ is selected from hydrogen and methyl;

$W_2$ is selected from $CR_7$ and N; wherein $R_7$ is selected from hydrogen and halo;

$Y_1$ is selected from $CH_2$ and C(O); or $Y_1$ and $W_2$ taken together can form a double bond where $W_2$ is C and $Y_1$ is CH;

$Y_2$, $Y_3$, $Y_6$ and $Y_7$ are independently selected from N and $CR_9$; where at least two of $Y_2$, $Y_3$, $Y_6$ and $Y_7$ are $CR_9$; wherein each $R_9$ is independently selected from hydrogen and halo;

$Y_5$ is selected from $(CR_{13a}R_{13b})_{1-3}$; wherein $R_{13a}$ and $R_{13b}$ are independently selected from hydrogen and $C_{1-6}$alkyl; wherein the alkyl of $R_{13a}$ or $R_{13b}$ is optionally substituted with a radical selected from hydroxy, $C_{1-4}$alkyl, halo, halo-substituted-$C_{1-4}$alkyl, $C_{1-4}$alkoxy and halo-substituted-$C_{1-4}$alkoxy; and $R_{14}$ is selected from hydrogen, $C_{1-6}$alkyl, halo, cyano, $C_{1-6}$alkoxy, halo-substituted-$C_{1-6}$alkyl and halo-substituted-$C_{1-6}$alkoxy.

In another embodiment, n is selected from 0, 1 and 2; A is selected from phenyl, pyridinyl, thiazolyl, 1H-1,2,4-triazole substituted with methyl, pyrimidinyl and naphthyl; $R_1$ is selected from $S(O)_{0-2}R_{4a}$, —C(O)$X_2R_{4a}$ and —C(O)OX$_2R_{4a}$; wherein $X_2$ is selected from a bond and methylene; $R_{4a}$ is selected from methyl, trifluoromethyl, t-butyl, pyranyl, hydroxypropyl, propyl, piperidinyl substituted with t-butoxycarbonyl, pyrrolidinyl and phenyl; $R_2$ is halo; $W_2$ is selected from CH and N; and $Y_1$ is selected from $CH_2$ and C(O); or $Y_1$ and $W_2$ taken together can form a double bond where $W_2$ is C and $Y_1$ is CH.

In another embodiment, $Y_2$, $Y_3$, $Y_6$ and $Y_7$ are independently selected from N and CH, where at least two of $Y_2$, $Y_3$, $Y_6$ and $Y_7$ are $CR_9$; wherein each $R_9$ is independently selected from hydrogen and halo; $Y_5$ is selected from —$CH_2$—, —CH($CH_3$)$CH_2$—, —CH($C_2H_5$)—, —CH($CH_2OH$)— and —CH($CH_3$)—; and $R_{14}$ is selected from hydrogen, halo, methyl, isopropyl, t-butyl, cyclopropyl, difluoroethyl, trifluoromethyl, trifluoromethoxy, methoxy, difluoromethoxy and fluorooxetanyl.

In another embodiment are compounds selected from: 4-(methylsulfonyl)-1-(5-(1-(4-(trifluoromethoxy)benzyl)azetidin-3-yloxy)pyrazin-2-yl)piperazin-2-one; 4-(3,5-difluoro-4-(1-(1-(4-(trifluoromethyl)phenyl)propyl)azetidin-3-yloxy)phenyl)-1-(methylsulfonyl)piperidine; 3-chloro-2-((3-(2,6-difluoro-4-(1-(methylsulfonyl)piperidin-4-yl)phenoxy)azetidin-1-yl)methyl)-5-(trifluoromethyl)pyridine; 2-((3-(2,6-difluoro-4-(1-(methylsulfonyl)piperidin-4-yl)phenoxy)azetidin-1-yl)methyl)-5-(trifluoromethyl)pyrimidine; 4-(3,5-difluoro-4-(1-(4-(3-fluorooxetan-3-yl)benzyl)azetidin-3-yloxy)phenyl)-1-(methylsulfonyl)piperidine; 2-(3-(2,6-difluoro-4-(1-(methylsulfonyl)piperidin-4-yl)phenoxy)azetidin-1-yl)-2-(4-(trifluoromethyl)phenyl)ethanol; 4-(3,5-difluoro-4-(1-(naphthalen-2-ylmethyl)azetidin-3-yloxy)phenyl)-1-(methylsulfonyl)piperidine; 4-(3,5-difluoro-4-(1-(naphthalen-1-ylmethyl)azetidin-3-yloxy)phenyl)-1-(methylsulfonyl)piperidine; 1-(3,5-difluoro-4-(1-(4-(trifluoromethyl)benzyl)azetidin-3-yloxy)phenyl)-4-(methylsulfonyl)piperazine; 1-(3,5-difluoro-4-(1-(4-(trifluoromethyl)benzyl)azetidin-3-yloxy)phenyl)-4-(methylsulfonyl)piperazin-2-one; 4-(3,5-difluoro-4-(1-(4-(trifluoromethyl)benzyl)azetidin-3-yloxy)phenyl)-1-(methylsulfonyl)-1,2,3,6-tetrahydropyridine; 1-(4-(3,5-difluoro-4-(1-(4-(trifluoromethyl)benzyl)azetidin-3-yloxy)phenyl)-5,6-dihydropyridin-1(2H)-yl)-2,2,2-trifluoroethanone; 4-(3,5-difluoro-4-(1-(4-(trifluoromethyl)benzyl)azetidin-3-yloxy)phenyl)-1-(tetrahydro-2H-pyran-4-ylsulfonyl)piperidine; tert-butyl 4-(4-(3,5-difluoro-4-(1-(4-(trifluoromethyl)benzyl)azetidin-3-yloxy)phenyl)piperidin-1-ylsulfonyl)piperidine-1-carboxylate; 4-(3,5-difluoro-4-(1-(4-(trifluoromethyl)benzyl)azetidin-3-yloxy)phenyl)-1-(piperidin-4-ylsulfonyl)piperidine; t-butyl 3-(4-(3,5-difluoro-4-(1-(4-(trifluoromethyl)benzyl)azetidin-3-yloxy)phenyl)piperidin-1-ylsulfonyl)pyrrolidine-1-carboxylate; 4-(3,5-difluoro-4-(1-(4-(trifluoromethyl)benzyl)azetidin-3-yloxy)phenyl)-1-(pyrrolidin-3-ylsulfonyl)piperidine; 3-(4-(3,5-difluoro-4-(1-(4-(trifluoromethyl)benzyl)azetidin-3-yloxy)phenyl)piperidin-1-ylsulfonyl)propan-1-ol; 2-(4-(methylsulfonyl)piperazin-1-yl)-5-(1-(4-(trifluoromethyl)benzyl)azetidin-3-yloxy)pyrimidine; 4-(3,5-Difluoro-4-(1-(4-(trifluoromethyl)benzyl)pyrrolidin-3-yloxy)phenyl)-1-(methylsulfonyl)piperidine; 4-(3,5-difluoro-4-(3-methyl-1-(4-(trifluoromethyl)benzyl)azetidin-3-yloxy)phenyl)-1-(methylsulfonyl)piperidine; 3-((3-(2,6-difluoro-4-(1-(methylsulfonyl)piperidin-4-yl)phenoxy)azetidin-1-yl)methyl)-5-(trifluoromethyl)-1,2,4-oxadiazole; 1-(3-fluoro-4-(1-(4-(trifluoromethyl)benzyl)azetidin-3-yloxy)phenyl)-4-(methylsulfonyl)piperazine; 3-tert-butyl-5-((3-(2,6-difluoro-4-(1-(methylsulfonyl)piperidin-4-yl)phenoxy)azetidin-1-yl)methyl)-1,2,4-oxadiazole; 5-((3-(2,6-difluoro-4-(1-(methylsulfonyl)piperidin-4-yl)phenoxy)azetidin-1-yl)methyl)-3-isopropyl-1,2,4-oxadiazole; 3-cyclopropyl-5-((3-(2,6-difluoro-4-(1-(methylsulfonyl)piperidin-4-yl)phenoxy)azetidin-1-yl)methyl)-1,2,4-oxadiazole; 3-((3-(2,6-difluoro-4-(1-(methylsulfonyl)piperidin-4-yl)phenoxy)azetidin-1-yl)methyl)-5-isopropyl-1,2,4-oxadiazole; 5-((3-(2,6-difluoro-4-(1-(methylsulfonyl)piperidin-4-yl)phenoxy)azetidin-1-yl)methyl)-3-(trifluoromethyl)-1,2,4-oxadiazole; 5-((3-(2,6-difluoro-4-(1-(methylsulfonyl)piperidin-4-yl)phenoxy)azetidin-1-yl)methyl)-3-(1,1-difluoroethyl)-1,2,4-oxadiazole; 4-(3,5-difluoro-4-(1-((1-methyl-3-(trifluoromethyl)-1H-pyrazol-5-yl)methyl)azetidin-3-yloxy)phenyl)-1-(methylsulfonyl)piperidine; 2-((3-(2,6-difluoro-4-(1-(methylsulfonyl)piperidin-4-yl)phenoxy)azetidin-1-yl)methyl)-4-(trifluoromethyl)thiazole; 4-((3-(2,6-difluoro-4-(1-(methylsulfonyl)piperidin-4-yl)phenoxy)azetidin-1-yl)methyl)-2-(trifluoromethyl)thiazole; 4-(3,5-difluoro-4-(1-((1-methyl-3-(trifluoromethyl)-1H-1,2,4-triazol-5-yl)methyl)azetidin-3-yloxy)phenyl)-1-(methylsulfonyl)piperidine; 4-(propane-1-sulfonyl)-1-{5-[(1-{[4-(trifluoromethyl)phenyl]methyl}azetidin-3-yl)oxy]pyridin-2-yl}piperazin-2-one; 4-methanesulfonyl-1-{5-[(1-{[4-(propan-2-yl)phenyl]methyl}azetidin-3-yl)oxy]pyridin-2-yl}piperazin-2-one; 4-methanesulfonyl-1-{5-[(1-{[4-(propan-2-yl)phenyl]methyl}azetidin-3-yl)oxy]pyrazin-2-yl}piperazin-2-one; 4-methanesulfonyl-1-{5-[(1-{[4-(trifluoromethoxy)phenyl]methyl}azetidin-3-yl)oxy]pyrazin-2-yl}piperazin-2-one; 4-{3,5-difluoro-4-[(1-{1-[4-(trifluoromethyl)phenyl]ethyl}azetidin-3-yl)oxy]phenyl}-1-methanesulfonylpiperidine; 4-methanesulfonyl-1-{5-[(1-{[4-(trifluoromethyl)phenyl]methyl}azetidin-3-yl)oxy]pyrazin-2-yl}piperazin-2-one; 2-(4-methanesulfonylpiperazin-1-yl)-5-[(1-{[4-(propan-2-yl)phenyl]methyl}azetidin-3-yl)oxy]pyrazine; 4-methanesulfonyl-1-{5-[(1-{[4-(trifluoromethyl)phenyl]methyl}azetidin-3-yl)oxy]pyridin-2-yl}piperazin-2-one; 1-methanesulfonyl-4-{5-[(1-{[4-(trifluoromethyl)phenyl]methyl}azetidin-3-yl)oxy]pyridin-2-yl}piperazine; 1-(propane-1-sulfonyl)-4-{5-[(1-{[4-(trifluoromethyl)phenyl]methyl}azetidin-3-yl)oxy]pyridin-2-yl}piperazine; 2-(4-methanesulfonylpiperazin-1-yl)-5-[(1-{[4-(trifluoromethyl)phenyl]methyl}azetidin-3-yl)oxy]pyrazine; 1-methanesulfonyl-4-{5-[(1-{[4-(trifluoromethoxy)phenyl]methyl}azetidin-3-yl)oxy]pyridin-2-yl}piperazine; 1-methanesulfonyl-4-{4-[(1-{[4-(propan-2-yl)phenyl]methyl}azetidin-3-yl)oxy]phenyl}piperazine; 1-methanesulfonyl-4-{5-[(1-{[4-(propan-2-yl)phenyl]methyl}azetidin-3-yl)oxy]pyridin-2-yl}piperazine; 1-[5-({1-[(4-chlorophenyl)methyl]azetidin-3-yl}oxy)pyridin-2-yl]-4-methanesulfonylpiperazine; 4-{3,5-difluoro-4-[(1-{1-[4-(trifluoromethyl)phenyl]propan-2-yl}azetidin-3-yl)oxy]phenyl}-1-methanesulfonylpiperidine; 1-{5-[(1-{[4-(difluoromethoxy)phenyl]methyl}azetidin-3-yl)oxy]pyridin-2-yl}-4-methanesulfonylpiperazine; 1-methanesulfonyl-4-[5-({1-[(4-methylphenyl)methyl]azetidin-3-yl}oxy)pyridin-2-yl]piperazine; 1-methanesulfonyl-4-[5-({1-[(4-methoxyphenyl)methyl]azetidin-3-yl}oxy)pyridin-2-yl]piperazine; benzyl 4-{5-[(1-{[4-(propan-2-yl)phenyl]methyl}azetidin-3-yl)oxy]pyrazin-2-yl}piperazine-1-carboxylate; 1-methanesulfonyl-4-{5-[(1-{[3-(trifluoromethyl)phenyl]methyl}azetidin-3-yl)oxy]pyridin-2-yl}piperazine; benzyl 3-oxo-4-{5-[(1-{[4-(propan-2-yl)phenyl]methyl}azetidin-3-yl)oxy]pyridin-2-yl}piperazine-1-carboxylate; 4-{3,5-difluoro-4-[(1-{[4-(trifluoromethyl)phenyl]methyl}azetidin-3-yl)oxy]phenyl}-1-methanesulfonylpiperidine; 4-{3,5-difluoro-4-[(1-{[4-(trifluoromethyl)phenyl]methyl}azetidin-3-yl)oxy]phenyl}-1-methanesulfonyl-1,2,3,6-tetrahydropyridine; 4-{3,5-difluoro-4-[(1-{[4-(trifluoromethyl)phenyl]methyl}azetidin-3-yl)oxy]phenyl}-1-(oxane-4-sulfonyl)piperidine; 3-(4-{3,5-difluoro-4-[(1-{[4-(trifluoromethyl)phenyl]methyl}azetidin-3-yl)oxy]phenyl}piperidine-1-sulfonyl)propan-1-ol; 4-{3,5-difluoro-4-[(1-{[4-(3-fluorooxetan-3-yl)phenyl]methyl}azetidin-3-yl)oxy]phenyl}-1-methanesulfonylpiperidine; 4-{3,5-difluoro-4-[(1-{[3-(trifluoromethyl)-1,2,4-oxadiazol-5-yl]methyl}azetidin-3-yl)oxy]phenyl}-1-methanesulfonylpiperidine; 4-{3,5-difluoro-4-[(1-{[4-(trifluoromethyl)-1,3-thiazol-2-yl]methyl}azetidin-3-yl)oxy]phenyl}-1-methanesulfonylpiperidine; 4-{3,5-difluoro-4-[(1-{[3-(propan-2-yl)-1,2,4-oxadiazol-5-yl]methyl}azetidin-3-yl)oxy]phenyl}-1-methanesulfonylpiperidine; 4-{3,5-difluoro-4-[(1-{[1- methyl-3-(trifluoromethyl)-1H-pyrazol-5-yl]methyl}azetidin-3-yl)oxy]phenyl}-1-methanesulfonylpiperidine; 4-{4-[(1-{[3-(1,1-difluoroethyl)-1,2,4-oxadiazol-5-yl]methyl}azetidin-3-yl)oxy]-3,5-difluorophenyl}-1-methanesulfonylpiperidine; 1-{3-fluoro-4-[(1-{[4-(trifluoromethyl)phenyl]methyl}azetidin-3-yl)oxy]phenyl}-4-methanesulfonylpiperazine; 4-[4-({1-[(3-cyclopropyl-1,2,4-oxadiazol-5-yl)methyl]azetidin-3-yl}oxy)-3,5-difluorophenyl]-1-methanesulfonylpiperidine; 4-(3,5-difluoro-4-{[1-(naphthalen-2-ylmethyl)azetidin-3-yl]oxy}phenyl)-1-methanesulfonylpiperidine; 1-{3,5-difluoro-4-[(1-{[4-(trifluoromethyl)phenyl]methyl}azetidin-3-yl)oxy]phenyl}-4-methanesulfonylpiperazine; 2-(4-methanesulfonylpiperazin-1-yl)-5-[(1-{[4-(trifluoromethyl)phenyl]methyl}azetidin-3-yl)oxy]pyrimidine; tert-butyl 3-(4-{3,5-difluoro-4-[(1-{[4-(trifluoromethyl)phenyl]methyl}azetidin-3-yl)oxy]phenyl}piperidine-1-sulfonyl)pyrrolidine-1-carboxylate; 4-{3,5-difluoro-4-[(1-{1-[4-(trifluoromethyl)phenyl]propyl}azetidin-3-yl)oxy]phenyl}-1-methanesulfonylpiperidine; 4-[4-({1-[(5-tert-butyl-1,2,4-oxadiazol-3-yl)methyl]azetidin-3-yl}oxy)-3,5-difluorophenyl]-1-methanesulfonylpiperidine; tert-butyl 4-(4-{3,5-difluoro-4-[(1-{[4-(trifluoromethyl)phenyl]methyl}azetidin-3-yl)oxy]phenyl}piperidine-1-sulfonyl)piperidine-1-carboxylate; 3-chloro-2-({3-[2,6-difluoro-4-(1-methanesulfonylpiperidin-4-yl)phenoxy]azetidin-1-yl}methyl)-5-(trifluoromethyl)pyridine; 1-{3,5-difluoro-4-[(1-{[4-(trifluoromethyl)phenyl]methyl}azetidin-3-yl)oxy]phenyl}-4-methanesulfonylpiperazin-2-one; 4-{3,5-difluoro-4-[(1-{[5-(propan-2-yl)-1,2,4-oxadiazol-3-yl]methyl}azetidin-3-yl)oxy]phenyl}-1-methanesulfonylpiperidine; 4-{3,5-difluoro-4-[(1-{[2-(trifluoromethyl)-1,3-thiazol-4-yl]methyl}azetidin-3-yl)oxy]phenyl}-1-methanesulfonylpiperidine; 4-{3,5-difluoro-4-[(1-{[4-(trifluoromethyl)phenyl]methyl}azetidin-3-yl)oxy]phenyl}-1-(piperidine-4-sulfonyl)piperidine; 4-{3,5-difluoro-4-[(1-{[4-(trifluoromethyl)phenyl]methyl}azetidin-3-yl)oxy]phenyl}-1-(pyrrolidine-3-sulfonyl)piperidine; 4-(3,5-difluoro-4-{[1-(naphthalen-1-ylmethyl)azetidin-3-yl]oxy}phenyl)-1-methanesulfonylpiperidine; 1-(4-{3,5-difluoro-4-[(1-{[4-(trifluoromethyl)phenyl]methyl}azetidin-3-yl)oxy]phenyl}-1,2,3,6-tetrahydropyridin-1-yl)-2,2,2-trifluoroethan-1-one; 2-({3-[2,6-difluoro-4-(1-methanesulfonylpiperidin-4-yl)phenoxy]azetidin-1-yl}methyl)-5-(trifluoromethyl)pyrimidine; and 2-{3-[2,6-difluoro-4-(1-methanesulfonylpiperidin-4-yl)phenoxy]azetidin-1-yl}-2-[4-(trifluoromethyl)phenyl]ethan-1-ol.

In another embodiment are compounds of Formula Ib:

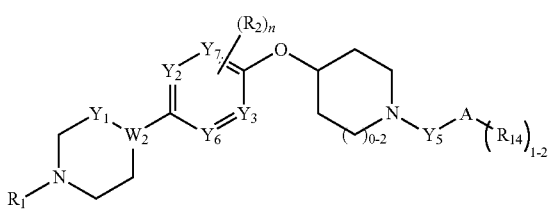

Ib in which: A is selected from $C_{6-10}$aryl and a 5-6 member heteroaryl containing 1 to 3 heteroatoms selected from N, S and O; n is selected from 0, 1 and 2; is selected from $S(O)_{0-2}R_{4a}$ and —$C(O)OX_2R_{4a}$; wherein $X_2$ is selected from a bond and $C_{1-4}$alkylene; $R_{4a}$ is selected from $C_{1-6}$alkyl and $C_{6-10}$aryl; $R_2$ is halo; $W_2$ is selected from $CR_7$ and N; wherein $R_7$ is selected from hydrogen and halo; $Y_1$ is selected from $CH_2$ and $C(O)$; $Y_2$, $Y_3$, $Y_6$ and $Y_7$ are independently selected from N and $CR_9$, wherein $R_9$ is selected from hydrogen and halo; wherein at least two of $Y_2$, $Y_3$, $Y_6$ and $Y_7$ are $CR_9$; $Y_5$ is selected from $(CR_{13a}R_{13b})_{1-3}$; wherein $R_{13a}$ and $R_{13b}$ are independently selected from hydrogen and $C_{1-6}$alkyl; and $R_{14}$ is selected from $C_{1-6}$alkyl, halo, cyano, $C_{1-6}$alkoxy, halo-substituted-$C_{1-6}$alkyl and halo-substituted-$C_{1-6}$alkoxy.

In a further embodiment, n is selected from 0, 1 and 2; A is selected from phenyl, oxadiazolyl, 1H-1,2,4-triazolyl, pyrazolyl and thiazolyl; $R_1$ is selected from $S(O)_{0-2}R_{4a}$ and —$C(O)OX_2R_{4a}$; wherein $X_2$ is methylene; $R_{4a}$ is selected from methyl, propyl and phenyl; $R_2$ is halo; $W_2$ is selected from $CR_7$ and N; wherein $R_7$ is selected from hydrogen and halo; and $Y_1$ is selected from $CH_2$ and $C(O)$.

In a further embodiment, $Y_2$, $Y_3$, $Y_6$ and $Y_7$ are independently selected from N and $CR_9$, wherein $R_9$ is selected from hydrogen and halo; wherein at least two of $Y_2$, $Y_3$, $Y_6$ and $Y_7$ are $CR_9$; $Y_5$ is selected from —$CH_2$—, —$CH(CH_3)CH_2$— and —$CH(CH_3)$—; and $R_{14}$ is selected from methyl, halo, isopropyl, fluoroisopropyl, t-butyl, cyclopropyl, difluoromethyl, difluoroethyl, trifluoromethyl, trifluoromethoxy, methoxy and difluoromethoxy.

In a further embodiment are compounds selected from: 5-((4-(2,6-difluoro-4-(1-(methylsulfonyl)piperidin-4-yl)phenoxy)piperidin-1-yl)methyl)-2-(trifluoromethyl)pyridine; 4-(3,5-difluoro-4-(1-(3-(trifluoromethyl)benzyl)piperidin-4-yloxy)phenyl)-1-(methylsulfonyl)piperidine; 5-((4-(5-(4-(Methylsulfonyl)piperazin-1-yl)pyrazin-2-yloxy) piperidin-1-yl)methyl)-3-(trifluoromethyl)-1,2,4-oxadiazole; 5-((4-(2,6-difluoro-4-(4-fluoro-1-(methylsulfonyl)piperidin-4-yl)phenoxy)piperidin-1-yl)methyl)-3-(trifluoromethyl)-1,2,4-oxadiazole; 5-((4-(2,3-difluoro-4-(1-(methylsulfonyl)piperidin-4-yl)phenoxy) piperidin-1-yl)methyl)-3-(trifluoromethyl)-1,2,4-oxadiazole; 5-((4-(2,5-difluoro-4-(1-(methylsulfonyl)piperidin-4-yl)phenoxy)piperidin-1-yl)methyl)-3-(trifluoromethyl)-1,2,4-oxadiazole; 5-((4-(3,5-difluoro-4-(1-(methylsulfonyl)piperidin-4-yl)phenoxy)piperidin-1-yl)methyl)-3-(trifluoromethyl)-1,2,4-oxadiazole; 5-(1-(4-(2,6-difluoro-4-(1-(methylsulfonyl)piperidin-4-yl)phenoxy) piperidin-1-yl)ethyl)-3-(trifluoromethyl)-1,2,4-oxadiazole; 5-((4-(2-fluoro-4-(1-(methylsulfonyl)piperidin-4-yl)phenoxy)piperidin-1-yl)methyl)-3-(trifluoromethyl)-1,2,4-oxadiazole; 5-((4-(3-fluoro-4-(1-(methylsulfonyl)piperidin-4-yl)phenoxy)piperidin-1-yl)methyl)-3-(trifluoromethyl)-1,2,4-oxadiazole; 4-(3,5-difluoro-4-(1-((1-methyl-3-(trifluoromethyl)-1H-pyrazol-5-yl)methyl)piperidin-4-yloxy)phenyl)-1-(methylsulfonyl)piperidine; 2-((4-(2,6-difluoro-4-(1-(methylsulfonyl)piperidin-4-yl)phenoxy) piperidin-1-yl)methyl)-4-(trifluoromethyl)thiazole; 4-((4-(2,6-difluoro-4-(1-(methylsulfonyl)piperidin-4-yl)phenoxy) piperidin-1-yl)methyl)-2-(trifluoromethyl)thiazole; 4-(3,5-difluoro-4-(1-((1-methyl-3-(trifluoromethyl)-1H-1,2,4-triazol-5-yl)methyl)piperidin-4-yloxy)phenyl)-1-(methylsulfonyl)piperidine; 3-((4-(2,6-difluoro-4-(1-(methylsulfonyl)piperidin-4-yl)phenoxy)piperidin-1-yl) methyl)-5-(trifluoromethyl)-1,2,4-oxadiazole; 5-((4-(2,6-difluoro-4-(1-(methylsulfonyl)piperidin-4-yl)phenoxy) piperidin-1-yl)methyl)-3-isopropyl-1,2,4-oxadiazole; 2-((4-(5-(1-(methylsulfonyl)piperidin-4-yl)pyrazin-2-yloxy) piperidin-1-yl)methyl)-4-(trifluoromethyl)thiazole; 5-((4-(4-(1-(methylsulfonyl)piperidin-4-yl)phenoxy)piperidin-1-yl) methyl)-3-(trifluoromethyl)-1,2,4-oxadiazole; 4-(3,5-

Difluoro-4-(1-(4-(trifluoromethyl)benzyl)azetidin-3-yloxy)phenyl)-1-(methylsulfonyl)piperidineine; 5-((4-(2,6-Difluoro-4-(1-(methylsulfonyl)piperidin-4-yl)phenoxy)piperidin-1-yl)methyl)-3-(trifluoromethyl)-1,2,4-oxadiazole; 5-((4-(2,6-difluoro-4-(1-(methylsulfonyl)piperidin-4-yl)phenoxy)piperidin-1-yl)methyl)-3-isopropyl-1,2,4-oxadiazole; 5-((4-(2,6-difluoro-4-(1-(methylsulfonyl)piperidin-4-yl)phenoxy)piperidin-1-yl)methyl)-3-(1,1-difluoroethyl)-1,2,4-oxadiazole; 5-((4-(2,6-difluoro-4-(1-(methylsulfonyl)piperidin-4-yl)phenoxy)piperidin-1-yl)methyl)-3-(difluoromethyl)-1,2,4-oxadiazole; 5-((4-(2,6-difluoro-4-(1-(methylsulfonyl)piperidin-4-yl)phenoxy)piperidin-1-yl)methyl)-3-(2-fluoropropan-2-yl)-1,2,4-oxadiazole; 4-(3,5-Difluoro-4-(1-(4-(trifluoromethyl)benzyl)pyrrolidin-3-yloxy)phenyl)-1-(methylsulfonyl)piperidine; 4-(2,6-difluoro-4-(1-(methylsulfonyl)piperidin-4-yl)phenoxy)-1-(4-(trifluoromethyl)benzyl)azepane; 4-{3,5-difluoro-4-[(1-{[4-(trifluoromethyl)-1,3-thiazol-2-yl]methyl}piperidin-4-yl)oxy]phenyl}-1-methanesulfonylpiperidine; 4-{2-fluoro-4-[(1-{[3-(trifluoromethyl)-1,2,4-oxadiazol-5-yl]methyl}piperidin-4-yl)oxy]phenyl}-1-methanesulfonylpiperidine; 4-{3-fluoro-4-[(1-{[3-(trifluoromethyl)-1,2,4-oxadiazol-5-yl]methyl}piperidin-4-yl)oxy]phenyl}-1-methanesulfonylpiperidine; 4-{3,5-difluoro-4-[(1-{[2-(trifluoromethyl)-1,3-thiazol-4-yl]methyl}piperidin-4-yl)oxy]phenyl}-1-methanesulfonylpiperidine; 4-{3,5-difluoro-4-[(1-{[1-methyl-3-(trifluoromethyl)-1H-pyrazol-5-yl]methyl}piperidin-4-yl)oxy]phenyl}-1-methanesulfonylpiperidine; and 4-{3,5-difluoro-4-[(1-{[3-(trifluoromethyl)-1,2,4-oxadiazol-5-yl]methyl}piperidin-4-yl)oxy]phenyl}-4-fluoro-1-methanesulfonylpiperidine.

Further compounds of the invention are detailed in the Examples and Tables, infra.

The present invention also includes all suitable isotopic variations of the compounds of the invention, or pharmaceutically acceptable salts thereof. An isotopic variation of a compound of the invention or a pharmaceutically acceptable salt thereof is defined as one in which at least one atom is replaced by an atom having the same atomic number but an atomic mass different from the atomic mass usually found in nature. Examples of isotopes that may be incorporated into the compounds of the invention and pharmaceutically acceptable salts thereof include but are not limited to isotopes of hydrogen, carbon, nitrogen and oxygen such as $^2H$, $^3H$, $^{11}C$, $^{13}C$, $^{14}C$, $^{15}N$, $^{17}O$, $^{18}O$, $^{35}S$, $^{18}F$, $^{36}Cl$ and $^{123}I$. Certain isotopic variations of the compounds of the invention and pharmaceutically acceptable salts thereof, for example, those in which a radioactive isotope such as $^3H$ or $^{14}C$ is incorporated, are useful in drug and/or substrate tissue distribution studies. In particular examples, $^3H$ and $^{14}C$ isotopes may be used for their ease of preparation and detectability. In other examples, substitution with isotopes such as $^2H$ may afford certain therapeutic advantages resulting from greater metabolic stability, such as increased in vivo half-life or reduced dosage requirements. Isotopic variations of the compounds of the invention or pharmaceutically acceptable salts thereof can generally be prepared by conventional procedures using appropriate isotopic variations of suitable reagents. For example, the following three examples can be deuterated as shown:

Deuterated Derivatives of Formula I

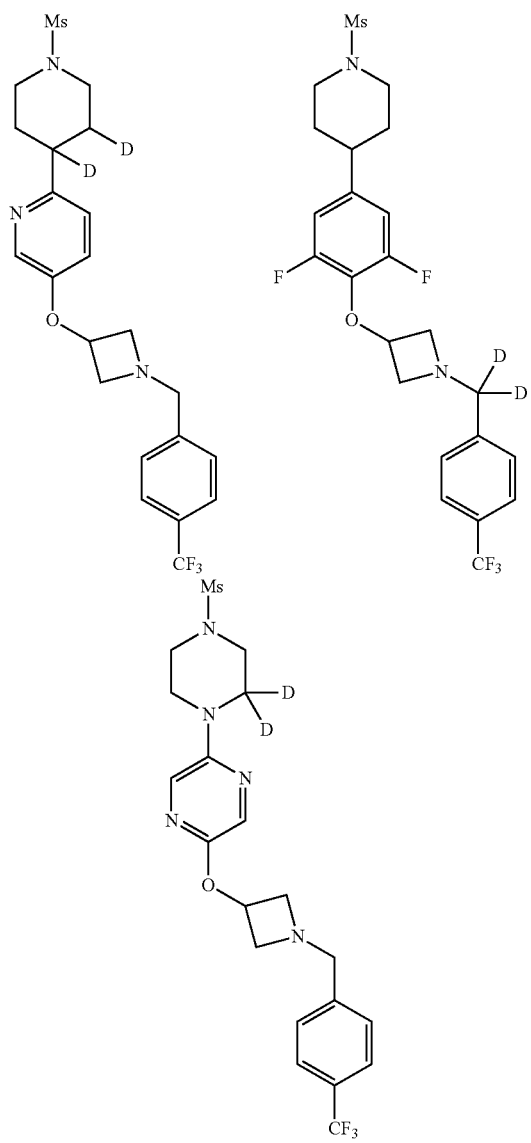

Pharmacology and Utility

Compounds of the invention modulate the activity of GPR119 and, as such, are useful for treating diseases or disorders in which the activity of GPR119 contributes to the pathology and/or symptomology of the disease. This invention further provides compounds of this invention for use in the preparation of medicaments for the treatment of diseases or disorders in which GPR119 activity contributes to the pathology and/or symptomology of the disease.

The resultant pathologies of Type II diabetes are impaired insulin signaling at its target tissues and failure of the insulin-producing cells of the pancreas to secrete an appropriate degree of insulin in response to a hyperglycemic signal. Current therapies to treat the latter include inhibitors of the β-cell ATP-sensitive potassium channel to trigger the release of endogenous insulin stores, or administration of exogenous insulin. Neither of these achieves accurate normalization of blood glucose levels and both carry the risk of inducing hypoglycemia. For these reasons, there has been intense interest in the development of pharmaceuticals that function in a glucose-dependent action, i.e. potentiators of glucose signaling. Physiological signaling systems which function in this manner are well-characterized and include the gut peptides GLP-1, GIP and PACAP. These hormones act via their cognate G-protein coupled receptor to stimulate the production of cAMP in pancreatic β-cells. The increased cAMP does not appear to result in stimulation of insulin release during the fasting or pre-prandial state. However, a series of biochemical targets of cAMP signaling, including the ATP-sensitive potassium channel, voltage-sensitive potassium channels and the exocytotic machinery, are modified in such a way that the insulin secretory response to a postprandial glucose stimulus is markedly enhanced. Accordingly, agonists of novel, similarly functioning, β-cell GPCRs, including GPR119, would also stimulate the release of endogenous insulin and consequently promote normoglycemia in Type II diabetes. It is also established that increased cAMP, for example as a result of GLP-1 stimulation, promotes β-cell proliferation, inhibits β-cell death and thus improves islet mass. This positive effect on β-cell mass is expected to be beneficial in both Type II diabetes, where insufficient insulin is produced, and Type I diabetes, where β-cells are destroyed by an inappropriate autoimmune response.

Some β-cell GPCRs, including GPR119, are also present in the hypothalamus where they modulate hunger, satiety, decrease food intake, controlling or decreasing weight and energy expenditure. Hence, given their function within the hypothalamic circuitry, agonists or inverse agonists of these receptors mitigate hunger, promote satiety and therefore modulate weight.

It is also well-established that metabolic diseases exert a negative influence on other physiological systems. Thus, there is often the codevelopment of multiple disease states (e.g. type I diabetes, type II diabetes, inadequate glucose tolerance, insulin resistance, hyperglycemia, hyperlipidemia, hypertriglyceridemia, hypercholesterolemia, dyslipidemia, obesity or cardiovascular disease in "Syndrome X") or secondary diseases which clearly occur secondary to diabetes (e.g. kidney disease, peripheral neuropathy). Thus, it is expected that effective treatment of the diabetic condition will in turn be of benefit to such interconnected disease states.

In an embodiment of the invention is a method for treatment of a metabolic disease and/or a metabolic-related disorder in an individual comprising administering to the individual in need of such treatment a therapeutically effective amount of a compound of the invention or a pharmaceutical composition thereof. The metabolic diseases and metabolic-related disorders are selected from, but not limited to, hyperlipidemia, type 1 diabetes, type 2 diabetes mellitus, idiopathic type 1 diabetes (Type Ib), latent autoimmune diabetes in adults (LADA), early-onset type 2 diabetes (EOD), youth-onset atypical diabetes (YOAD), maturity onset diabetes of the young (MODY), malnutrition-related diabetes, gestational diabetes, coronary heart disease, ischemic stroke, restenosis after angioplasty, peripheral vascular disease, intermittent claudication, myocardial infarction (e.g. necrosis and apoptosis), dyslipidemia, post-prandial lipemia, conditions of impaired glucose tolerance (IGT), conditions of impaired fasting plasma glucose, metabolic acidosis, ketosis, arthritis, obesity, osteoporosis, hypertension, congestive heart failure, left ventricular hypertrophy, peripheral arterial disease, diabetic retinopathy, macular degeneration, cataract, diabetic nephropathy, glomerulosclerosis, chronic renal failure, diabetic neuropathy, metabolic syndrome, syndrome X, premenstrual syndrome, coronary heart disease, angina pectoris, thrombosis, atherosclerosis, myocardial infarction, transient ischemic attacks, stroke, vascular restenosis, hyperglycemia, hyperinsulinemia, hyperlipidemia, hypertryglyceridemia, insulin resistance, impaired glucose metabolism, conditions of impaired glucose tolerance, conditions of impaired fasting plasma glucose, obesity, erectile dysfunction, skin and connective tissue disorders, foot ulcerations and ulcerative colitis, endothelial dysfunction and impaired vascular compliance.

In an embodiment of the invention are therapeutic benefits of GPR119 activity modulators derived from increasing levels of GIP and PPY. For example, neuroprotection, learning and memory, seizures and peripheral neuropathy.

GLP-1 and GLP-1 receptor agonists have been shown to be effective for treatment of neurodegenerative diseases and other neurological disorders. GLP-1 and exendin-4 have been shown to stimulate neurite outgrowth and enhance cell survival after growth factor withdrawal in PC12 cells. In a rodent model of neurodegeneration, GLP-1 and exendin-4 restore cholinergic marker activity in the basal forebrain. Central infusion of GLP-1 and exendin-4 also reduce the levels of amyloid-β peptide in mice and decrease amyloid precursor protein amount in cultured PC12 cells. GLP-1 receptor agonists have been shown to enhance learning in rats and the GLP-1 receptor knockout mice show deficiencies in learning behavior. The knockout mice also exhibit increased susceptibility to kainate-induced seizures which can be prevented by administration of GLP-1 receptor agonists. GLP-1 and exendin-4 has also been shown to be effective in treating pyridoxine-induced peripheral nerve degeneration, an experimental model of peripheral sensory neuropathy.

Glucose-dependent insulinotropic polypeptide (GIP) has also been shown to have effects on proliferation of hippocampal progenitor cells and in enhancing sensorimotor coordination and memory recognition.

In an embodiment of the invention are therapeutic benefits of GPR119 activity modulators. For example, GLP-2 and short bowel syndrome (SBS). Several studies in animals and from clinical trials have shown that GLP-2 is a trophic hormone that plays an important role in intestinal adaptation. Its role in regulation of cell proliferation, apoptosis, and nutrient absorption has been well documented. Short bowel syndrome is characterized by malabsorption of nutrients, water and vitamins as a result of disease or surgical removal of parts of the small intestine (eg. Crohn's disease). Therapies that improve intestinal adaptation are thought to be beneficial in treatment of this disease. In fact, phase II studies in SBS patients have shown that teduglutide, a GLP-2 analog, modestly increased fluid and nutrient absorption.

In an embodiment of the invention are therapeutic benefits of GPR119 activity modulators derived from increasing levels of GIP and PPY. For example, GLP-1, GIP and osteoporosis. GLP-1 has been shown to increase calcitonin and calcitonin related gene peptide (CGRP) secretion and expression in a murine C-cell line (CA-77). Calcitonin inhibits bone resorption by osteoclasts and promotes mineralization of skeletal bone. Osteoporosis is a disease that is characterized by reduced bone mineral density and thus GLP-1 induced increase in calcitonin might be therapeutically beneficial.

GIP has been reported to be involved in upregulation of markers of new bone formation in osetoblasts including collagen type I mRNA and in increasing bone mineral density. Like GLP-1, GIP has also been shown to inhibit bone resorption.

In an embodiment of the invention are therapeutic benefits of GPR119 activity modulators derived from increasing levels of GIP and PPY. For example, PPY and gastric emptying. GPR119 located on the pancreatic polypeptide (PP) cells of the islets has been implicated in the secretion of PPY. PPY has been reported to have profound effects on various physiological processes including modulation of gastric emptying and gastrointestinal motility. These effects slow down the digestive process and nutrient uptake and thereby prevent the postprandial elevation of blood glucose. PPY can suppress food intake by changing the expression of hypothalamic feeding-regulatory peptides. PP-overexpressing mice exhibited the thin phenotype with decreased food intake and gastric emptying rate.

In accordance with the foregoing, the present invention further provides a method for preventing or ameliorating the symptamology of any of the diseases or disorders described above in a subject in need thereof, which method comprises administering to said subject a therapeutically effective amount (See, "*Administration and Pharmaceutical Compositions*", infra) of a compound of Formula I or a pharmaceutically acceptable salt thereof. For any of the above uses, the required dosage will vary depending on the mode of administration, the particular condition to be treated and the effect desired.

Administration and Pharmaceutical Compositions

In general, compounds of the invention will be administered in therapeutically effective amounts via any of the usual and acceptable modes known in the art, either singly or in combination with one or more therapeutic agents. A therapeutically effective amount can vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, e.g. in divided doses up to four times a day or in retard form. Suitable unit dosage forms for oral administration comprise from ca. 1 to 50 mg active ingredient.

Compounds of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrollidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions can be sterilized and/or contain adjuvants, such as preserving, stabilizing, wetting or emulsifying agents, solution promoters, salts for regulating the osmotic pressure and/or buffers. In addition, they can also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations can also be used. Suitable formulations for topical application, e.g., to the skin and eyes, are preferably aqueous solutions, ointments, creams or gels well-known in the art. Such can contain solubilizers, stabilizers, tonicity enhancing agents, buffers and preservatives.

Compounds of the invention can be administered in therapeutically effective amounts in combination with one or more therapeutic agents (pharmaceutical combinations).

For example, synergistic effects can occur with other anti-obesity agents, anorectic agents, appetite suppressant and related agents. Diet and/or exercise can also have synergistic effects. Anti-obesity agents include, but are not limited to, apolipoprotein-B secretion/microsomal triglyceride transfer protein (apo-B/MTP) inhibitors, MCR-4 agonists, cholescystokinin-A (CCK-A) agonists, serotonin and norepinephrine reuptake inhibitors (for example, sibutramine), sympathomimetic agents, β3 adrenergic receptor agonists, dopamine agonists (for example, bromocriptine), melanocyte-stimulating hormone receptor analogs, cannabinoid 1 receptor antagonists [for example, compounds described in WO2006/047516), melanin concentrating hormone antagonists, leptons (the OB protein), leptin analogues, leptin receptor agonists, galanin antagonists, lipase inhibitors (such as tetrahydrolipstatin, i.e., Orlistat), anorectic agents (such as a bombesin agonist), Neuropeptide-Y antagonists, thyromimetic agents, dehydroepiandrosterone or an analogue thereof, glucocorticoid receptor agonists or antagonists, orexin receptor antagonists, urocortin binding protein antagonists, glucagon-like peptide-1 receptor agonists, ciliary neutrotrophic factors (such as Axokine™), human agouti-related proteins (AGRP), ghrelin receptor antagonists, histamine 3 receptor antagonists or reverse agonists, neuromedin U receptor agonists, noradrenergic anorectic agents (for example, phentermine, mazindol and the like) and appetite suppressants (for example, bupropion).

Where compounds of the invention are administered in conjunction with other therapies, dosages of the co-administered compounds will of course vary depending on the type of co-drug employed, on the specific drug employed, on the condition being treated and so forth.

A combined preparation or pharmaceutical composition can comprise a compound of the invention as defined above or a pharmaceutical acceptable salt thereof and at least one active ingredient selected from:

a) anti-diabetic agents such as insulin, insulin derivatives and mimetics; insulin secretagogues such as the sulfonylureas, e.g., Glipizide, glyburide and Amaryl; insulinotropic sulfonylurea receptor ligands such as meglitinides, e.g., nateglinide and repaglinide; insulin sensitizer such as protein tyrosine phosphatase-1B (PTP-1B) inhibitors such as PTP-112; GSK3 (glycogen synthase kinase-3) inhibitors such as SB-517955, SB-4195052, SB-216763, N,N-57-05441 and N,N-57-05445; RXR ligands such as GW-0791 and AGN- 194204; sodium-dependent glucose co-transporter inhibitors such as T-1095; glycogen phosphorylase A inhibitors such as BAY R3401; biguanides such as metformin; alpha-glucosidase inhibitors such as acarbose; GLP-1 (glucagon like peptide-1), GLP-1 analogs such as Exendin-4 and GLP-1 mimetics; DPPIV (dipeptidyl peptidase IV) inhibitors such as DPP728, LAF237 (vildagliptin—Example 1 of WO 00/34241), MK-0431, saxagliptin, GSK23A; an AGE breaker; a thiazolidone derivative (glitazone) such as pioglitazone, rosiglitazone, or (R)-1-{4-[5-methyl-2-(4-trifluoromethyl-phenyl)-oxazol-4-ylmethoxy]-benzenesulfonyl}-2,3-dihydro-1H-indole-2-carboxylic acid described in the patent application WO 03/043985, as compound 19 of Example 4, a non-glitazone type PPAR gamma agonist e.g. GI-262570; Diacylglycerol acetyltransferase (DGAT) inhibitors such as those disclosed in WO 2005044250, WO 2005013907, WO 2004094618 and WO 2004047755;

b) hypolipidemic agents such as 3-hydroxy-3-methyl-glutaryl coenzyme A (HMG-CoA) reductase inhibitors, e.g., lovastatin and related compounds such as those disclosed in U.S. Pat. No. 4,231,938, pitavastatin, simvastatin and related compounds such as those disclosed in U.S. Pat. Nos. 4,448,784 and 4,450,171, pravastatin and related compounds such as those disclosed in U.S. Pat. No. 4,346,227, cerivastatin, mevastatin and related compounds such as those disclosed in U.S. Pat. No. 3,983,140, velostatin, fluvastatin, dalvastatin, atorvastatin, rosuvastatin and related statin compounds disclosed in U.S. Pat. No. 5,753,675, rivastatin, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propanephosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0,142,146 A2, and quintoline and pyridine derivatives disclosed in U.S. Pat. Nos. 5,506,219 and 5,691,322. In addition, phosphinic acid compounds useful in inhibiting HMG CoA reductase suitable for use herein are disclosed in GB 2205837; squalene synthase inhibitors; FXR (farnesoid X receptor) and LXR (liver X receptor) ligands; cholestyramine; fibrates; nicotinic acid and aspirin;

c) an anti-obesity agent or appetite regulating agent such as a CB1 activity modulator, melanocortin receptor (MC4R) agonists, melanin-concentrating hormone receptor (MCHR) antagonists, growth hormone secretagogue receptor (GHSR) antagonists, galanin receptor modulators, orexin antagonists, CCK agonists, GLP-1 agonists, and other Pre-proglucagon-derived peptides; NPY1 or NPY5 antagonsist, NPY2 and NPY4 modulators, corticotropin releasing factor agonists, histamine receptor-3 (H3) modulators, aP2 inhibitors, PPAR gamma modulators, PPAR delta modulators, acetyl-CoA carboxylase (ACC) inhibitors, 11-β-HSD-1 inhibitors, adinopectin receptor modulators; beta 3 adrenergic agonists, such as AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, a thyroid receptor beta modulator, such as a thyroid receptor ligand as disclosed in WO 97/21993 (U. Cal SF), WO 99/00353 (KaroBio) and GB98/284425 (KaroBio), a SCD-1 inhibitor as disclosed in WO2005011655, a lipase inhibitor, such as orlistat or ATL-962 (Alizyme), serotonin receptor agonists, (e.g., BVT-933 (Biovitrum)), monoamine reuptake inhibitors or releasing agents, such as fenfluramine, dexfenfluramine, fluvoxamine, fluoxetine, paroxetine, sertraline, chlorphentermine, cloforex, clortermine, picilorex, sibutramine, dexamphetamine, phentermine, phenylpropanolamine or mazindol, anorectic agents such as topiramate (Johnson & Johnson), CNTF (ciliary neurotrophic factor)/Axokine® (Regeneron), BDNF (brain-derived neurotrophic factor), leptin and leptin receptor modulators, phentermine, leptin, bromocriptine, dexamphetamine, amphetamine, fenfluramine, dexfenfluramine, sibutramine, orlistat, dexfenfluramine, mazindol, phentermine, phendimetrazine, diethylpropion, fluoxetine, bupropion, topiramate, diethylpropion, benzphetamine, phenylpropanolamine or ecopipam, ephedrine, pseudoephedrine;

d) anti-hypertensive agents such as loop diuretics such as ethacrynic acid, furosemide and torsemide; diuretics such as thiazide derivatives, chlorithiazide, hydrochlorothiazide, amiloride; angiotensin converting enzyme (ACE) inhibitors such as benazepril, captopril, enalapril, fosinopril, lisinopril, moexipril, perinodopril, quintapril, ramipril and trandolapril; inhibitors of the Na-K-ATPase membrane pump such as digoxin; neutralendopeptidase (NEP) inhibitors e.g. thiorphan, terteo-thiorphan, SQ29072; ECE inhibitors e.g. SLV306; ACE/NEP inhibitors such as omapatrilat, sampatrilat and fasidotril; angiotensin II antagonists such as candesartan, eprosartan, irbesartan, losartan, telmisartan and valsartan, in particular valsartan; renin inhibitors such as aliskiren, terlakiren, ditekiren, RO 66-1132, RO-66-1168; beta-adrenergic receptor blockers such as acebutolol, atenolol, betaxolol, bisoprolol, metoprolol, nadolol, propranolol, sotalol and timolol; inotropic agents such as digoxin, dobutamine and milrinone; calcium channel blockers such as amlodipine, bepridil, diltiazem, felodipine, nicardipine, nimodipine, nifedipine, nisoldipine and verapamil; aldosterone receptor antagonists; aldosterone synthase inhibitors; and dual ET/AII antagonist such as those disclosed in WO 00/01389.

e) a HDL increasing compound;
f) Cholesterol absorption modulator such as Zetia® and KT6-971;
g) Apo-A1 analogues and mimetics;
h) thrombin inhibitors such as Ximelagatran;
i) aldosterone inhibitors such as anastrazole, fadrazole, eplerenone;
j) Inhibitors of platelet aggregation such as aspirin, clopidogrel bisulfate;
k) estrogen, testosterone, a selective estrogen receptor modulator, a selective androgen receptor modulator;
l) a chemotherapeutic agent such as aromatase inhibitors e.g. femara, anti-estrogens, topoisomerase I inhibitors, topoisomerase II inhibitors, microtubule active agents, alkylating agents, antineoplastic antimetabolites, platin compounds, compounds decreasing the protein kinase activity such as a PDGF receptor tyrosine kinase inhibitor preferably Imatinib ({N-{5-[4-(4-methyl-piperazino-methyl)-benzoylamido]-2-methylphenyl}-4-(3-pyridyl)-2-pyrimidine-amine}) described in the European patent application EP-A-0 564 409 as example 21 or 4-Methyl-N-[3-(4-methyl-imidazol-1-yl)-5-trifluoromethyl-phenyl]-3-(4-pyridin-3-yl-pyrimidin-2-ylamino)-benzamide described in the patent application WO 04/005281 as example 92; and
m) an agent interacting with a 5-HT$_3$ receptor and/or an agent interacting with 5-HT$_4$ receptor such as tegaserod described in the U.S. Pat. No. 5,510,353 as example 13, tegaserod hydrogen maleate, cisapride, cilansetron;

n) an agent for treating tobacco abuse, e.g., nicotine receptor partial agonists, bupropion hypochloride (also known under the tradename Zyban®) and nicotine replacement therapies;

o) an agent for treating erectile dysfunction, e.g., dopaminergic agents, such as apomorphine), ADD/ADHD agents (e.g., Ritalin®, Strattera®, Concerta® and Adderall®);

p) an agent for treating alcoholism, such as opioid antagonists (e.g., naltrexone (also known under the tradename ReVia®) and nalmefene), disulfuram (also known under the tradename Antabuse®), and acamprosate (also known under the tradename Campral®)). In addition, agents for reducing alcohol withdrawal symptoms may also be co-administered, such as benzodiazepines, beta-blockers, clonidine, carbamazepine, pregabalin, and gabapentin (Neurontin®);

q) other agents that are useful including anti-inflammatory agents (e.g., COX-2 inhibitors); antidepressants (e.g., fluoxetine hydrochloride (Prozac®)); cognitive improvement agents (e.g., donepezil hydrochloride (Aircept®) and other acetylcholinesterase inhibitors); neuroprotective agents (e.g., memantine); antipsychotic medications (e.g., ziprasidone (Geodon®), risperidone (Risperdal®), and olanzapine (Zyprexa®));

or, in each case a pharmaceutically acceptable salt thereof; and optionally a pharmaceutically acceptable carrier.

The invention also provides for a pharmaceutical combinations, e.g. a kit, comprising a) a first agent which is a compound of the invention as disclosed herein, in free form or in pharmaceutically acceptable salt form, and b) at least one co-agent. The kit can comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of Formula I and a co-agent, are both administered to a patient simultaneously in the form of a single entity or dosage. The term "non-fixed combination" means that the active ingredients, e.g. a compound of Formula I and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

Processes for Making Compounds of the Invention

The present invention also includes processes for the preparation of compounds of the invention. In the reactions described, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1991.

In the following schemes, several methods of preparing the compounds of the present invention are illustrative. One of skill in the art will appreciate that these methods are representative, and in no way inclusive of all methods for preparing the compounds of the present invention. The radicals in the schemes are as described in Formula I.

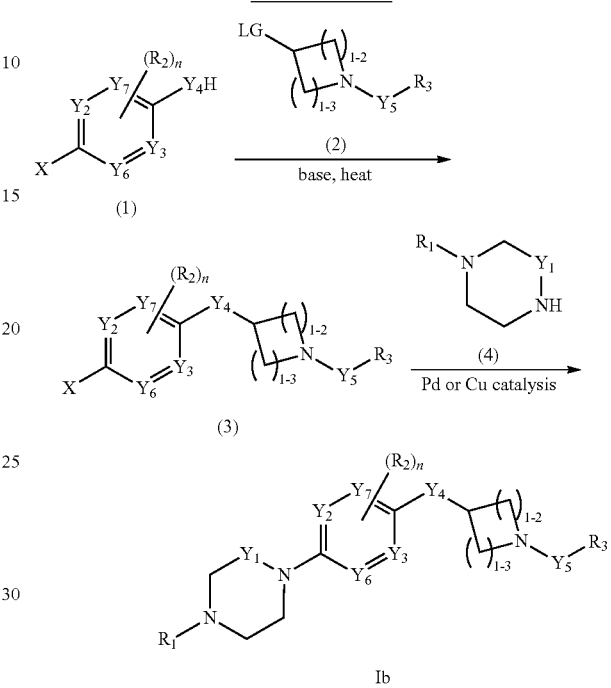

A compound of Formula Ib can be prepared as in reaction scheme I by reacting a compound of formula 1 (where X refers to a chloride, bromide, iodide, triflate, nonaflate and the like) with a compound of the formula 2 (where LG refers to a leaving group such as an aryl- or alkylsulfonate ester, halide or other appropriate group familiar to one skilled in the art) in a suitable solvent such as DMSO, DMF, tetrahydrofurane and the like in the presence of a suitable base such as KOtBu, $Cs_2CO_3$, NaH or the like at an elevated temperature such as 100° C. to generate an intermediate of the formula 3. Then, a compound of the formula 4 can be coupled with a compound of the formula 3 using the Pd or Cu methodology known in the art (for example, Shafir, A, Buchwald, S. F.; *J. Am. Chem. Soc.* 2006, 128, 8742 and references cited therein and Hartwig, J. F. *Handbook of Organopalladium Chemistry for Organic Synthesis*, Negishi, E., Ed., Wiley-Interscience: Weinheim, 2002). In this scheme, it is understood that the groups designated as $R_1$, $R_2$ and $R_3$ may be protected versions of the radicals defined in formula I which may be deprotected and manipulated to the final compound after completion of this scheme or in the middle of the scheme.

Reaction Scheme II

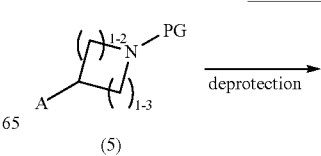

(5)

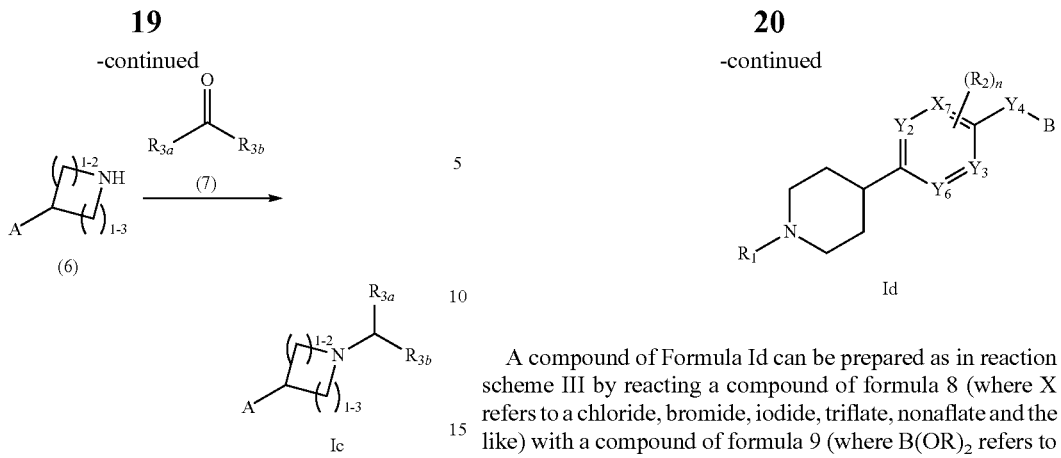

A compound of Formula Ic can be prepared as in reaction scheme II by deprotecting a compound of formula 5 (where PG refers to a protecting group such as Boc, Cbz, Fmoc, t-butyl, benzyl and the like) with methods known in the art (for example Wuts, P. G. M., Greene, T. W. *Greene's Protective Groups in Organic Synthesis*, Fourth Edition, Wiley-Interscience: Hoboken, 2007 and references cited therein) to generate an intermediate of the formula 6. Then, a compound of the formula 7 can be reductively aminated with a compound of the formula 6 using a suitable reducing agent such as sodium triacetoxyborohydride, sodium cyanoborohydride, sodium borohydride or the like in a solvent such as DMF, dichloroethane, tetrahydrofurane and the like in the presence or absence of a base such as triethylamine and the like to generate a compound of formula Ic. In this scheme, it is understood that the group designated as A may be a protected version of the radical defined in formula I which may be deprotected and manipulated to the final compound after completion of this scheme or in the middle of the scheme.

A compound of Formula Id can be prepared as in reaction scheme III by reacting a compound of formula 8 (where X refers to a chloride, bromide, iodide, triflate, nonaflate and the like) with a compound of formula 9 (where B(OR)$_2$ refers to a boronic acid or boronic ester such as boronic acid pinacol ester and the like) using the Pd methodology known in the art to generate an intermediate of the formula 10. Then, a compound of the formula 10 can be reduced to generate a piperidine intermediate of formula 11. Compound of formula 11 can further be functionalized to generate a compound of formula Id. In this scheme, it is understood that the group designated as B may be a protected version of the radical defined in formula I which may be deprotected and manipulated to the final compound after completion of this scheme or in the middle of the scheme.

Detailed descriptions of the synthesis of compounds of the Invention are given in the Examples, infra.

Additional Processes for Making Compounds of the Invention

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base. Alternatively, the salt forms of the compounds of the invention can be prepared using salts of the starting materials or intermediates.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Compounds of the invention in unoxidized form can be prepared from N-oxides of compounds of the invention by treating with a reducing agent (e.g., sulfur, sulfur dioxide, triphenyl phosphine, lithium borohydride, sodium borohydride, or the like) in a suitable inert organic solvent (e.g. acetonitrile, ethanol, aqueous dioxane, or the like) at 0 to 80° C.

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", 3$^{rd}$ edition, John Wiley and Sons, Inc., 1999.

Compounds of the present invention can be prepared conveniently, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Compounds of the invention can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds of the invention, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chromatography, or preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley And Sons, Inc., 1981.

In summary, the compounds of Formula I can be made by a process, which involves:

(a) that of reaction schemes I, II & III; and (b) optionally converting a compound of the invention into a pharmaceutically acceptable salt;

(c) optionally converting a salt form of a compound of the invention to a non-salt form;

(d) optionally converting an unoxidized form of a compound of the invention into a pharmaceutically acceptable N-oxide;

(e) optionally converting an N-oxide form of a compound of the invention to its unoxidized form;

(f) optionally resolving an individual isomer of a compound of the invention from a mixture of isomers;

(g) optionally converting a non-derivatized compound of the invention into a pharmaceutically acceptable prodrug derivative; and (h) optionally converting a prodrug derivative of a compound of the invention to its non-derivatized form.

Insofar as the production of the starting materials is not particularly described, the compounds are known or can be prepared analogously to methods known in the art or as disclosed in the Examples hereinafter.

One of skill in the art will appreciate that the above transformations are only representative of methods for preparation of the compounds of the present invention, and that other well known methods can similarly be used.

EXAMPLES

The present invention is further exemplified, but not limited, by the following Examples that illustrate the preparation of compounds of the invention and their intermediates.

Synthesis of Building Blocks

BB1

4-(1-Fluorocyclobutyl)benzaldehyde

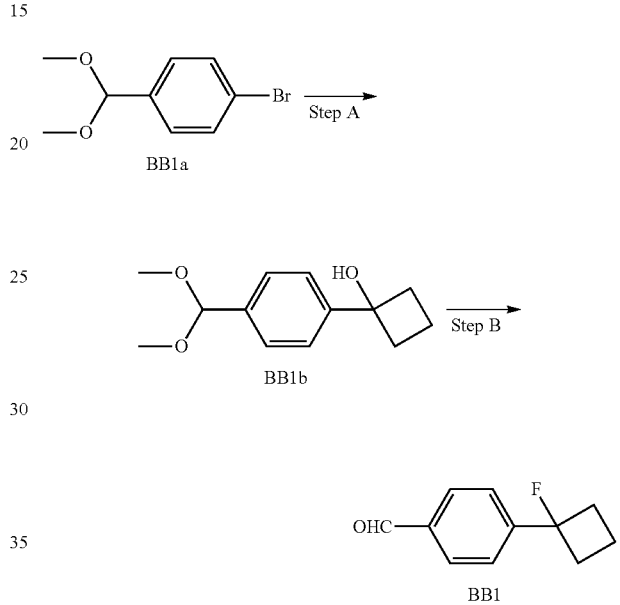

Step A: To a cold (−78° C.) solution of 1-bromo-4-(dimethoxymethyl)benzene BB1a (693 mg, 3 mmol) in anhydrous tetrahydrofuran (10 mL) is added n-BuLi (2.5 M in hexanes, 1.32 mL, 3.3 mmol) and the mixture is stirred for 45 min under nitrogen atmosphere. Oxetan-3-one (216 mg, 3 mmol) in anhydrous tetrahydrofuran (2 mL) is added and the cooling bath is removed. The reaction mixture is stirred for 2 h, saturated NH$_4$Cl (5 mL) is added and the mixture is stirred for another 15 min. Tetrahydrofuran is evaporated, water is added and the mixture is extracted with ethyl acetate (4×). The combined organic phase is dried (Na$_2$SO$_4$), filtered and concentrated. Purification by flash chromatography (hexanes/ethyl acetate gradient) affords 1-(4-(dimethoxymethyl)phenyl)cyclobutanol BB1b as white crystals: $^1$H-NMR (400 MHz, DMSO-d$_6$) δ=7.60 (m, 2H), 7.40 (m, 2H), 6.37 (s, 1H), 5.39 (s, 1H), 4.76 (d, J=6.8 Hz, 2H), 4.67 (d, J=6.8 Hz, 2H), 3.24 (s, 6H).

Step B: To a cold (−78° C.) solution of BB1b (112 mg, 0.5 mmol) in anhydrous dichloromethane is added DAST (79 μL, 0.6 mmol) and the mixture is stirred for 90 min at −78° C., then 30 min at 0° C. The reaction mixture is quenched with saturated NH$_4$Cl, diluted with water and extracted with dichloromethane (3×). The combined organic phase is dried (Na$_2$SO$_4$), concentrated and the crude material is purified by flash chromatography (hexanes/ethyl acetate gradient) to afford 4-(1-fluorocyclobutyl)benzaldehyde BB1 as white solid: $^1$H-NMR (400 MHz, CDCl$_3$) δ=10.06 (s, 1H), 7.97 (m, 2H), 7.78 (m, 2H), 5.16 (m, 2H), 4.86 (m, 2H).

BB2

5-(chloromethyl)-3-(2-fluoropropan-2-yl)-1,2,4-oxadiazole

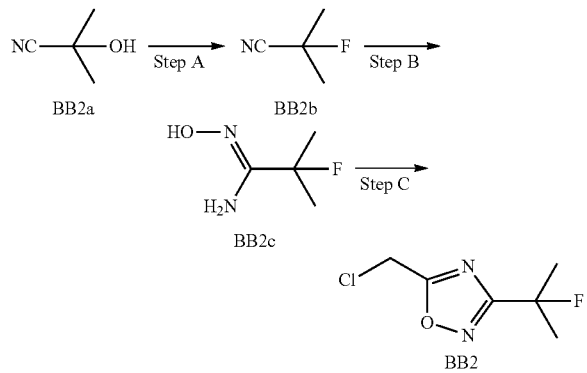

Step A: A solution of acetone cyanohydrin BB2a (457 μL, 5 mmol) in dichloromethane (20 mL) is cooled to −78° C. and Deoxo-Fluor (50% in toluene, 1.38 mL, 7.5 mmol) is added. The reaction mixture is allowed to warm to room temperature and stirred overnight. The mixture is quenched with aqueous sodium bicarbonate and the mixture is extracted with dichloromethane (7×). The combined organic phase is dried over sodium sulfate and concentrated in vacuo to afford 2-fluoro-2-methylpropanenitrile BB2b: $^1$H-NMR (400 MHz, CDCl$_3$) δ=1.76 (d, J=20.8 Hz). The compound is used without purification.

Step B: A solution of BB2b (100 mg, 1.1 mmol) in ethanol (0.5 mL) and hydroxylamine (50% in water, 184 μL, 3 mmol) is stirred at room temperature overnight. Water is removed and the residue is co-evaporated with toluene (3×) to afford (Z)-2-fluoro-N'-hydroxy-2-methylpropanimidamide BB2c. The product is used without purification.

Step C: A solution of BB2c (114 mg, 0.9 mmol) and chloroacetic anhydride (171 mg, 1 mmol) in acetic acid (0.5 mL) is heated to 120° C. overnight. The reaction mixture is cooled to room temperature, water is added and the mixture is extracted with dichlorometane (3×). The combined organic phase is washed with aqueous sodium carbonate (2×) and brine, dried over sodium sulfate and concentrated in vacuo to afford 5-(chloromethyl)-3-(2-fluoropropan-2-yl)-1,2,4-oxadiazole BB2: $^1$H-NMR (400 MHz, CDCl$_3$) δ=4.70 (s, 2H), 1.81 (d, J=21.6 Hz, 6H); $^{19}$F-NMR (376.46 MHz, CDCl$_3$) δ=−140.32.

BB3

5-(chloromethyl)-3-(1,1-difluoroethyl)-1,2,4-oxadiazole

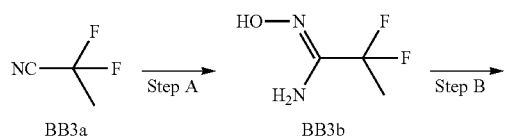
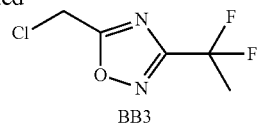

Step A: A solution of 2,2-difluoropropanenitrile BB3a (273 mg, 3 mmol) in ethanol (0.6 mL) is cooled to 0° C. and hydroxylamine (50% in water, 276 μL, 4.5 mmol) is added. The reaction mixture is stirred at room temperature overnight. Water is removed and the crude material is co-evaporated with toluene (3×) to afford (Z)-2,2-difluoro-N'-hydroxypropanimidamide BB3b: $^1$H-NMR (400 MHz, CDCl$_3$) δ=8.09 (bs, 1H), 4.81 (bs, 2H), 1.81 (t, J=18.9 Hz, 3H); MS calcd. for C$_3$H$_6$F$_2$N$_2$O ([M+H]$^+$): 125.0, found: 125.1. The product is used without purification.

Step B: A solution of BB3b (117 mg, 0.94 mmol) and chloroacetyl chloride (150 μL, 1.89 mmol) in toluene (5 mL) is heated to 110° C. overnight. The solvent is evaporated, the crude material dissolved in dichloromethane, washed with water (2×) sodium carbonate (2×) and brine. The organic phase is dried over sodium sulfate and concentrated in vacuo to give 5-(chloromethyl)-3-(1,1-difluoroethyl)-1,2,4-oxadiazole BB3 as an oil: $^1$H-NMR (400 MHz, CDCl$_3$) δ=4.75 (s, 2H), 2.10 (t, J=18.7 Hz, 3H); $^{19}$F-NMR (376.46 MHz, CDCl$_3$) δ=−91.57. The product is used without purification.

BB4

5-(chloromethyl)-1-methyl-3-(trifluoromethyl)-1H-pyrazole

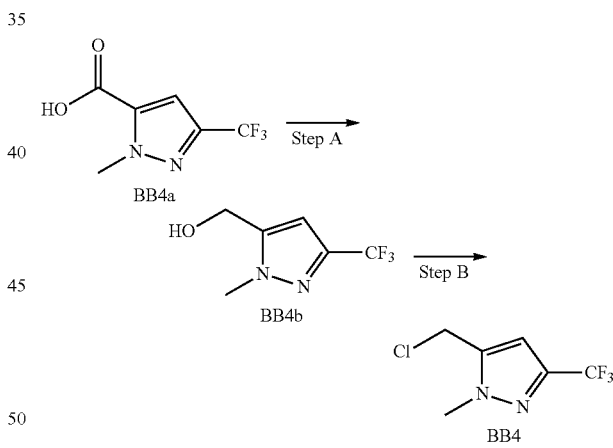

Step A: 1-Methyl-3-(trifluoromethyl)-1H-pyrazole-5-carboxylic acid BB4a (837 mg, 4.3 mmol) is dissolved in anhydrous tetrahydrofurane (10 mL), then LiAlH$_4$ (2.16 mL of 2.0 M in tetrahydrofurane, 4.3 mmol) is added dropwise and stirred at rt for 1 h. The mixture is quenched by dropwise addition of 1N HCl, then is made basic by addition of saturated NaHCO$_3$ and extracted with EtOAc (3×). The organic layers are combined, washed with brine, dried (MgSO$_4$), filtered and concentrated to provide (1-methyl-3-(trifluoromethyl)-1H-pyrazol-5-yl)methanol BB4b as a clear oil. $^1$H NMR (400 MHz, CDCl$_3$) δ=6.46 (s, 1H), 4.69 (d, J=5.6 Hz, 2H), 3.95 (s, 3H); MS calcd. for C$_6$H$_8$F$_3$N$_2$O ([M+H]$^+$): 181.0, found: 181.1.

Step B: Alcohol BB4b (696 mg, 3.86 mmol) is dissolved in dichloromethane (10 mL), then diisopropylethylamine (1.34 mL, 7.73 mmol) and methanesulfonyl chloride (330 mg, 4.25 mmol) are added and stirred at rt for 3 h. The mixture is concentrated and purified by flash column chromatography (silica gel, EtOAc/Hexane gradient) to provide 5-(chloromethyl)-1-methyl-3-(trifluoromethyl)-1H-pyrazole BB4 as a yellow oil: $^1$H-NMR (400 MHz, CDCl$_3$) δ=6.54 (s, 1H), 4.59 (s, 2H), 3.97 (s, 3H); MS calcd. for $C_6H_7ClF_3N_2$ ([M+H]$^+$): 199.0, found: 199.1.

Example A1

1-(5-(1-(4-isopropylbenzyl)azetidin-3-yloxy)pyridin-2-yl)-4-(methylsulfonyl)piperazine

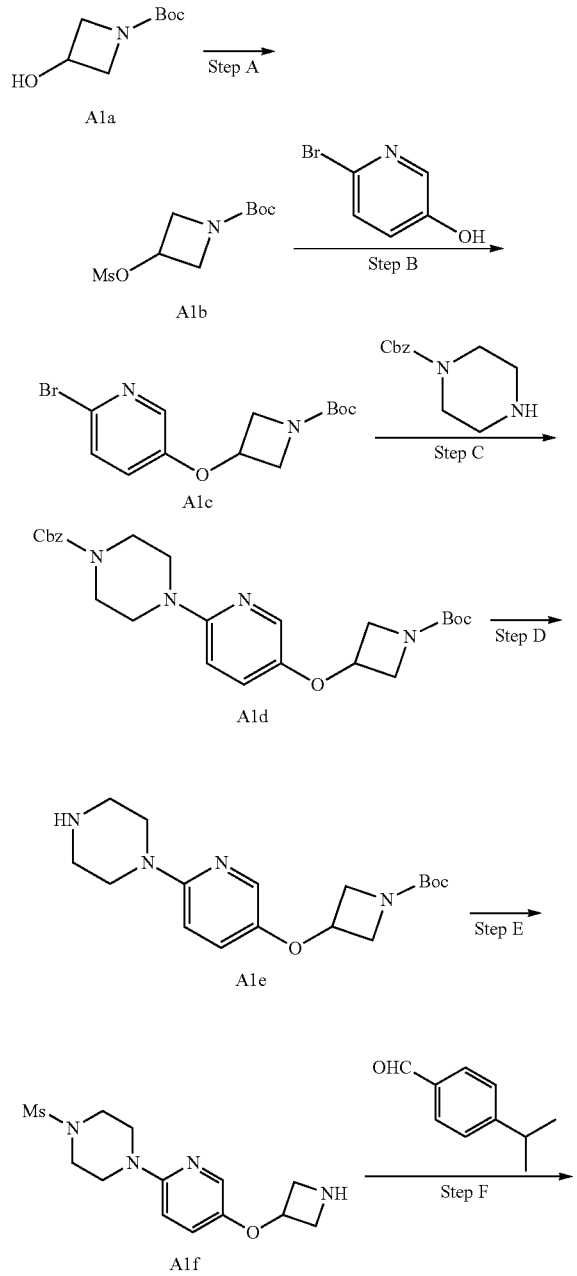

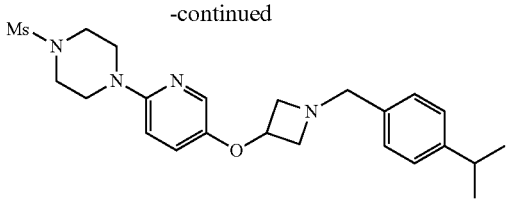

Example A1

Step A: A solution of tert-butyl 3-hydroxyazetidine-1-carboxylate A1a (2 g, 11.5 mmol) in dichloromethane (0.5M, 23 mL) is treated with ethyldiisopropylamine (3 mL, 17.5 mmol) and the mixture is cooled to 0° C. Methanesulfonyl chloride (0.99 mL, 12.7 mmol) is then added dropwise and the mixture is allowed to stir at room temperature for 6 hours. The mixture is diluted with dichloromethane, washed with 1M HCl, brine, dried over sodium sulfate and concentrated in vacuo to afford tert-butyl 3-(methylsulfonyloxy)azetidine-1-carboxylate A1b as oil that solidifies upon standing: $^1$H-NMR (400 MHz, CDCl$_3$) δ=5.25-5.19 (m, 1H), 4.30 (ddd, J=10.4, 6.4, 1.2 Hz, 2H), 4.12 (ddd, J=10.4, 4.0, 1.2 Hz, 2H), 3.09 (s, 3H), 1.46 (s, 9H); MS calcd. for $C_9H_{18}NO_5S$ ([M+H]$^+$): 252.1, found: 252.2. The product is used without purification.

Step B: A solution of 2-bromo-5-hydroxypyridine (1 g, 5.75 mmol) in dimethylsulfoxide (20 mL) is treated with potassium terbutoxide (839 mg, 7.48 mmol) and the mixture is stirred at room temperature for 20 minutes. A solution of Intermediate A1b (1.73 g, 6.88 mmol) in dimethylsulfoxide (10 mL) is then added dropwise and the mixture is stirred at 100° C. for 3 days. The mixture is cooled to room temperature, diluted with water and extracted with ethyl acetate (3×). The combined organic phases are then washed with brine, dried over sodium sulfate and concentrated in vacuo. The crude material is purified by flash chromatography (ethyl acetate/hexanes gradient) to afford tert-butyl 3-(6-bromopyridin-3-yloxy)azetidine-1-carboxylate A1c as a light yellow solid: $^1$H-NMR (400 MHz, CDCl$_3$) δ=7.92 (d, J=3.2 Hz, 1H), 7.41 (d, J=8.8 Hz, 1H), 7.00 (dd, J=8.4, 2.8 Hz, 1H), 4.94-4.88 (m, 1H), 4.33 (ddd, J=9.6, 6.4, 0.8 Hz, 2H), 4.02 (ddd, J=10.0, 4.0, 0.8 Hz, 2H), 1.47 (s, 9H); MS calcd. for $C_{13}H_{18}BrN_2O_3$ ([M+H]$^+$): 329.0, found: 329.1.

Step C: A microwave vial charged with Intermediate A1c (900 mg, 2.73 mmol), tris(dibenzylideneacetone)dipalladium (75 mg, 0.08 mmol), 9,9-dimethyl-4,5-bis(diphenylphosphino)xanthene (142 mg, 0.24 mmol), sodium terbutoxide (394 mg, 4.1 mmol) and benzyl piperazine-1-carboxylate (723 mg, 3.28 mmol) is sealed, evacuated, set under nitrogen and treated with toluene (7 mL). The resulting mixture is heated to 100° C. for 4 hours. The mixture is diluted with ethyl acetate and washed with water. The aqueous phase is then re-extracted with ethyl acetate. The combined organics are dried over sodium sulfate, concentrated in vacuo and the crude material is purified by flash chromatography (ethyl acetate/hexanes gradient) to afford benzyl 4-(5-(1-(tert-butoxycarbonyl)azetidin-3-yloxy)pyridin-2-yl)piperazine-1-carboxylate A1d as a light yellow solid: $^1$H-NMR (400 MHz, CDCl$_3$) δ=7.76 (d, J=3.2 Hz, 1H), 7.40-7.32 (m, 5H), 7.08 (dd, J=9.2, 3.2 Hz, 1H), 6.66 (d, J=8.8 Hz, 1H), 5.19 (s, 2H), 4.86-4.81 (m, 1H), 4.28 (dd, J=10.4, 6.4 Hz, 2H), 4.00 (dd, J=10.4, 4.0 Hz, 2H), 3.66-3.63 (m, 4H), 3.46-3.43 (m, 4H), 1.47 (s, 9H); MS calcd. for $C_{25}H_{33}N_4O_5$ ([M+H]$^+$): 469.2, found: 469.2.

Step D: To a solution of Intermediate A1d (1.03 g, 2.2 mmol) in methanol (20 mL) is added palladium on carbon (10%, 103 mg). The mixture is then saturated with hydrogen and subjected to hydrogenolysis (1 atm) for 4 hours. Additional palladium on carbon (10%, 103 mg) is added and the mixture is stirred under hydrogen atmosphere for additional 4 hours. The mixture is then filtered through Celite and washed with methanol. The solvent is evaporated to afford tert-butyl 346-(piperazin-1-yl)pyridin-3-yloxy)azetidine-1-carboxylate A1e as a thick oil that solidifies over time: $^1$H-NMR (400 MHz, CDCl$_3$) δ=9.82 (s, 1H), 7.61 (s, 1H), 7.15 (d, J=7.6 Hz, 1H), 6.77 (d, J=7.6 Hz, 1H), 4.82-4.75 (m, 1H), 4.21 (dd, J=9.6, 6.4 Hz, 2H), 3.90 (dd, J=9.6, 3.6 Hz, 2H), 3.82 (m, 4H), 3.32 (m, 4H), 1.37 (s, 9H); MS calcd. for C$_{17}$H$_{27}$N$_4$O$_3$ ([M+H]$^+$): 335.2, found: 335.2.

Step E: A solution of Intermediate A1e (115 mg, 0.34 mmol) in dichlorometane (2 mL) is treated with triethylamine (0.1 mL, 0.72 mmol) followed by a solution of methanesulfonyl chloride (29.3 µL, 0.38 mmol) in dichloromethane (0.1 mL). The mixture is then stirred overnight, treated with trifluoroacetic acid (1 mL) and stirred at room temperature for another 3 hours. The mixture is then loaded on a silica-bound tosic acid resin (0.66 mmol/g, 1.55 g, 1.02 mmol) and washed extensively with methanol/dichloromethane. The filtrate is then discarded and the desired compound is eluted with 2M ammonia in methanol. The solvent is concentrated in vacuo to afford 1-(5-(azetidin-3-yloxy)pyridin-2-yl)-4-(methylsulfonyl)piperazine A1f as a light yellow solid: $^1$H-NMR (400 MHz, CDCl$_3$) δ=7.79 (d, J=3.2 Hz, 1H), 7.09 (dd, J=8.8, 2.8 Hz, 1H), 6.69 (d, J=8.8 Hz, 1H), 4.96 (quint, J=6.0 Hz, 1H), 3.95-3.91 (m, 2H), 3.84-3.80 (m, 2H), 3.59-3.56 (m, 4H), 3.37-3.34 (m, 4H), 2.83 (s, 3H); MS calcd. for C$_{13}$H$_{21}$N$_4$O$_3$S ([M+H]$^+$): 313.1, found: 313.0.

Step F: To a solution of Intermediate A1f (10 mg, 0.032 mmol) in dichloroethane (0.5 mL) is added 4-isopropylbenzaldehyde (7.3 µL, 0.048 mmol) followed by sodium triacetoxyborohydride (7.5 mg, 0.035 mmol) and acetic acid (2 µL, 0.035 mmol). The mixture is then stirred at room temperature overnight, silica-bound tosyl hydrazine (0.93 mmol/g, 103 mg, 0.096 mmol) is added and the mixture is subjected to microwave irradiation (100° C., 5 minutes). The mixture is filtered and the solvent is evaporated in vacuo. The crude material is purified by flash chromatography (dichloromethane/methanol gradient) to afford the title compound (Example A1): $^1$H-NMR (400 MHz, CDCl$_3$) δ=7.72 (d, J=2.8 Hz, 1H), 7.14-7.09 (m, 5H), 6.99 (dd, J=9.2, 2.8 Hz, 1H), 6.57 (d, J=9.2 Hz, 1H), 4.67 (quint, J=5.6 Hz, 1H), 3.74-3.70 (m, 2H), 3.59 (s, 2H), 3.48-3.45 (m, 4H), 3.27-3.24 (m, 4H), 3.10-3.06 (m, 2H), 2.82 (quint, J=7.2 Hz, 1H), 2.73 (s, 3H), 1.17 (d, J=6.8 Hz, 6H); MS calcd. for C$_{23}$H$_{33}$N$_4$O$_3$S ([M+H]$^+$): 445.2, found: 445.2.

Example A2

Benzyl 4-(5-(1-(4-isopropylbenzyl)azetidin-3-yloxy) pyridin-2-yl)-3-oxopiperazine-1-carboxylate

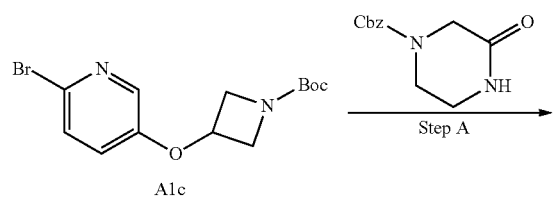

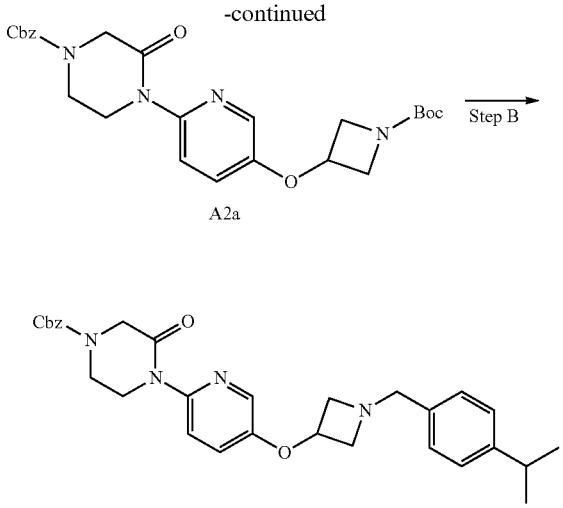

Step A: A microwave vial charged with Intermediate A1c (200 mg, 0.61 mmol), tris(dibenzylideneacetone)dipalladium (17 mg, 0.19 mmol), 9,9-dimethyl-4,5-bis(diphenylphosphino)xanthene (32 mg, 0.055 mmol), cesium carbonate (594 mg, 1.82 mmol) and benzyl 3-oxopiperazine-1-carboxylate (157 mg, 0.67 mmol) is sealed, evacuated, set under nitrogen and treated with dioxane (3.3 mL). The resulting mixture is heated to 120° C. for 4 hours. The mixture is diluted with ethyl acetate and washed with water. The aqueous phase is then re-extracted with ethyl acetate. The combined organics are dried over sodium sulfate, concentrated in vacuo and the crude material is purified by flash chromatography (ethyl acetate/hexanes gradient) to afford benzyl 4-(5-(1-(tert-butoxycarbonyl)azetidin-3-yloxy)pyridin-2-yl)-3-oxopiperazine-1-carboxylate A2a as a light yellow oil: $^1$H-NMR (400 MHz, CDCl$_3$) δ=7.96 (d, J=2.8 Hz, 1H), 7.89-7.82 (m, 1H), 7.41-7.35 (m, 5H), 7.13 (dd, J=8.8, 3.2 Hz, 1H), 5.21 (s, 2H), 4.95-4.89 (m, 1H), 4.36 (s, 2H), 4.34-4.31 (m, 2H), 4.10-4.07 (m, 2H), 4.05-4.01 (m, 2H), 4.86-4.83 (m, 2H), 1.47 (s, 9H); MS calcd. for C$_{25}$H$_{31}$N$_4$O$_6$ ([M+H]$^+$): 483.2, found: 483.3.

Step B: A solution of Intermediate A2a (51 mg, 0.106 mmol) in dichloromethane (0.3 mL) is treated with trifluoroacetic acid (0.3 mL) and the mixture is stirred at room temperature for 5 hours. The solvent is evaporated, the crude is diluted with dichloromethane and it is passed through a silica-bound carbonate resin. The resin is then washed extensively with dichloromethane/methanol. The solvent is evaporated and the crude is dissolved in tetrahydrofuran, treated with 4-isopropylbenzaldehyde (16 µL, 0.106 mmol) and macroporous triacetoxyborohydride (2.31 mmol/g, 76.2 mg, 0.176 mmol) and the mixture is stirred at room temperature overnight. The mixture is then filtered and the solvent is evaporated in vacuo. The crude material is purified by flash chromatography (ethyl acetate/hexanes gradient) to afford the title compound (Example A2): $^1$H-NMR (400 MHz, CDCl$_3$) δ=7.98 (d, J=2.4 Hz, 1H), 7.83-7.74 (m, 1H), 7.41-7.35 (m, 5H), 7.24-7.19 (m, 4H), 7.13 (dd, J=9.2, 3.2 Hz, 1H), 5.20 (s, 2H), 4.85 (quint, J=5.6 Hz, 1H), 4.35 (s, 2H), 4.08-4.05 (m, 2H), 3.85-3.80 (m, 4H), 3.68 (s, 1H), 3.21-3.17 (m, 2H), 3.91 (septet, J=6.8 Hz, 1H), 1.26 (d, J=7.2 Hz, 6H); MS calcd. for $C_{30}H_{35}N_4O_4$ ([M+H]$^+$): 515.3, found: 515.2.

Example A3

4-(methylsulfonyl)-1-(5-(1-(4-(trifluoromethyl)benzyl)azetidin-3-yloxy)pyridin-2-yl)piperazin-2-one

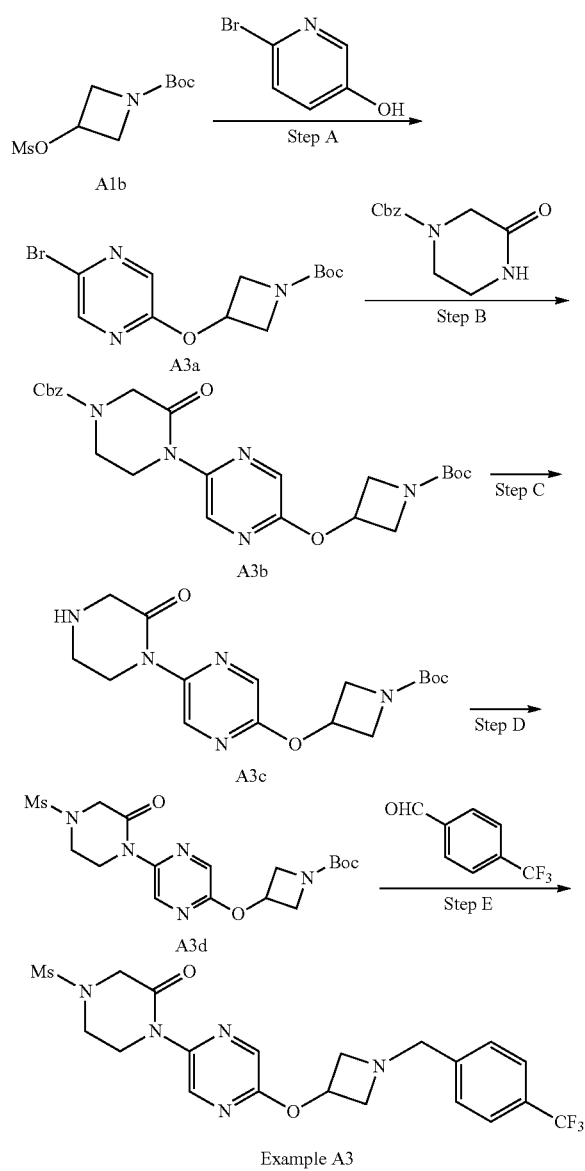

Example A3

Step A: A solution of 5-bromopyrazin-2-ol (2 g, 11.4 mmol) in dimethylsulfoxide (40 mL) is treated with potassium terbutoxide (1.67 g, 14.9 mmol) and the mixture is stirred at room temperature for 20 minutes. A solution of Intermediate A1b (3.45 g, 13.7 mmol) in dimethylsulfoxide (20 mL) is then added dropwise and the mixture is stirred at 100° C. for 3 days. The mixture is cooled to room temperature, diluted with water and extracted with ethyl acetate (3×). The combined organic phases are then washed with brine, dried over sodium sulfate and concentrated in vacuo. The crude material is purified by flash chromatography (ethyl acetate/hexanes gradient) to afford tert-butyl 3-(5-bromopyrazin-2-yloxy)azetidine-1-carboxylate A3a as a white solid: $^1$H-NMR (400 MHz, CDCl$_3$) δ=8.09 (d, J=1.2 Hz, 1H), 8.01 (d, J=1.6 Hz, 1H), 5.23-5.17 (m, 1H), 4.25 (ddd, J=10.0, 6.8, 0.8 Hz, 2H), 3.93-3.89 (m, 2H), 1.38 (s, 9H); MS calcd. for $C_{12}H_{17}BrN_3O_3$ ([M+H]$^+$): 330.0, found: 330.0.

Step B: A microwave vial charged with Intermediate A3a (323 mg, 0.98 mmol), tris(dibenzylideneacetone)dipalladium (26.9 mg, 0.03 mmol), 9,9-dimethyl-4,5-bis(diphenylphosphino)xanthene (50.9 mg, 0.088 mmol), cesium carbonate (956 mg, 2.93 mmol) and benzyl 3-oxopiperazine-1-carboxylate (252 mg, 1.07 mmol) is sealed, evacuated, set under nitrogen and treated with dioxane (5.4 mL). The resulting mixture is heated to 120° C. for 4 hours. The mixture is diluted with ethyl acetate and washed with water. The aqueous phase is then re-extracted with ethyl acetate. The combined organics are dried over sodium sulfate, concentrated in vacuo and the crude material is purified by flash chromatography (ethyl acetate/hexanes gradient) to afford benzyl 4-(5-(1-(tert-butoxycarbonyl)azetidin-3-yloxy)pyrazin-2-yl)-3-oxopiperazine-1-carboxylate A3b as a light orange solid: $^1$H-NMR (400 MHz, CDCl$_3$) δ=8.72 (br s, 1H), 8.09 (s, 1H), 7.41-7.34 (m, 5H), 5.36-5.30 (m, 1H), 5.21 (s, 2H), 4.38 (s, 2H), 4.36-4.33 (m, 2H), 4.04-3.98 (m, 4H), 3.89-3.86 (m, 2H), 1.47 (s, 9H); MS calcd. for $C_{24}H_{30}N_5O_6$ ([M+H]$^+$): 484.2, found: 484.0.

Step C: To a solution of Intermediate A3b (615 g, 1.27 mmol) in methanol (26 mL) is added palladium on carbon (10%, 62 mg). The mixture is then saturated with hydrogen and subjected to hydrogenolysis (1 atm) for 4 hours. Additional palladium on carbon (10%, 62 mg) is added and the mixture is stirred under hydrogen atmosphere for additional 4 hours. The mixture is then filtered through Celite and washed with methanol. The solvent is evaporated to afford tert-butyl 3-(5-(2-oxopiperazin-1-yl)pyrazin-2-yloxy)azetidine-1-carboxylate A3c as a thick oil: $^1$H-NMR (400 MHz, CDCl$_3$) δ=8.72 (d, J=1.6 Hz, 1H), 8.10 (d, J=1.6 Hz, 1H), 5.36-5.31 (m, 1H), 4.36 (ddd, J=10.0, 6.4, 1.2 Hz, 2H), 4.01 (dd, J=10.0, 4.4 Hz, 2H), 3.93 (t, J=5.6 Hz, 2H), 3.75 (s, 2H), 3.26 (t, J, 5.6 Hz, 2H), 1.47 (s, 9H); MS calcd. for $C_{16}H_{24}N_5O_4$ ([M+H]$^+$): 350.2, found: 350.2.

Step D: A solution of Intermediate A3c (349 mg, 1 mmol) in dichlorometane (8 mL) is treated with triethylamine (0.29 mL, 2.08 mmol) followed by a solution of methanesulfonyl chloride (85.1 µL, 1.1 mmol) in dichloromethane (0.2 mL). The mixture is then stirred overnight, the precipitate is filtered to afford tert-butyl 3-(5-(4-(methylsulfonyl)-2-oxopiperazin-1-yl)pyrazin-2-yloxy)azetidine-1-carboxylate A3d as a white solid. The mother liquors are diluted with dichloromethane and washed with saturated sodium carbonate. The aqueous phase is re-extracted with dichloromethane, the combined organic phases are dried over sodium sulfate and concentrated in vacuo to afford additional A3d as a light yellow solid: $^1$H-NMR (400 MHz, CDCl$_3$) δ=8.71 (d, J=1.6 Hz, 1H), 8.11 (d, J=1.2 Hz, 1H), 5.37-5.31 (m, 1H), 4.36 (ddd, J=10.0, 6.4, 0.8 Hz, 2H), 4.16 (s, 2H), 4.13-4.10 (m, 2H), 4.01 (dd, J=10.4, 4.0 Hz, 2H), 3.71-3.68 (m, 2H), 2.96 (s, 3H), 1.47 (s, 9H); MS calcd. for $C_{17}H_{26}N_5O_6S$ ([M+H]$^+$): 428.2, found: 428.2. The compound is used without purification.

Step E: A solution of Intermediate A3d (59 mg, 0.14 mmol) in dichloromethane (2 mL) is treated with trifluoroacetic acid (0.9 mL) and stirred at room temperature for 4 hours. The solvent is evaporated and the crude material is co-evaporated several times with chloroform, toluene and methanol. One third of the crude material is then treated with triethylamine (22 µL, 0.164 mmol), 4-trifluoromethyl benzaldehyde (17 µL, 0.124 mmol), macroporous triacetoxyborohydride (2.31 mmol/g, 88 mg, 0.205 mmol), dimethylformamide (2 ml), and stirred overnight. The solution is then filtered, concentrated, and purified via flash chromatography (ethyl acetate/hexanes gradient) to afford the title compound (Example A3): $^1$H NMR (400 MHz, CDCl$_3$) δ=8.65 (d, J=1.6 Hz, 1H), 8.07 (d, J=1.6 Hz, 1H), 7.62 (d, J=8.0 Hz, 2H), 7.47 (d, J=8.0 Hz, 2H), 5.34 (quint, J=5.6 Hz, 1H), 4.12-4.06 (m, 6H), 3.95 (br s, 2H), 3.68-3.65 (m, 2H), 3.51-3.44 (m, 2H), 2.93 (s, 3H); $^{19}$F NMR (376.46 MHz, CDCl$_3$) δ=−62.61; MS calcd. for C$_{20}$H$_{23}$F$_3$N$_5$O$_4$S ([M+H]$^+$): 486.1, found: 486.1.

Example A4

4-(methylsulfonyl)-1-(5-(1-(4-(trifluoromethoxy)benzyl)azetidin-3-yloxy)pyrazin-2-yl)piperazin-2-one

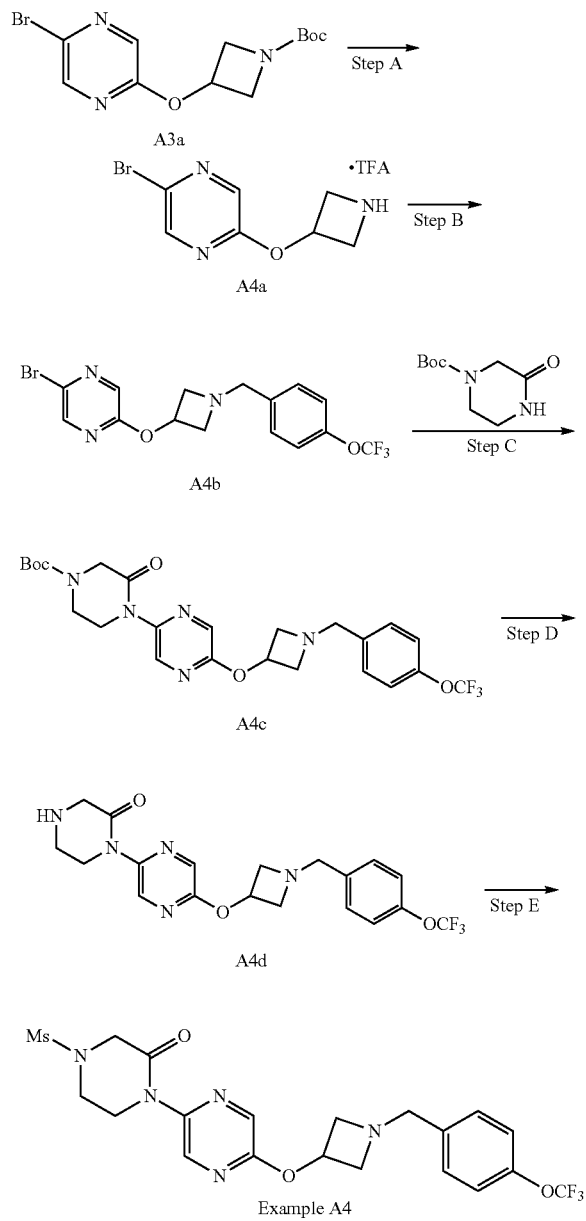

Step A: A suspension of Intermediate A3a (3 g, 9.1 mmol) in dichloromethane (15 mL) is cooled to 0° C. and treated with trifluoroacetic acid (5 mL). The mixture is stirred at 0° C. for 20 min, then warmed to room temperature and stirred for 7 hours. The solvent is removed and the crude is co-evaporated with toluene (1×) and methanol (1×) to afford 2-(azetidin-3-yloxy)-5-bromopyrazine trifluoroacetate salt A4a: MS calcd. for C$_7$H$_9$BrN$_3$O ([M+H]$^+$): 230.0, found: 230.0. The compound is used without purification.

Step B: A solution of Intermediate A4a in 1,2-dichloroethane (40 mL) is cooled to 0° C. and treated with ethyldiisopropylamine (4.76 mL, 27.3 mmol). The bath is removed and the mixture is treated with 4-trifluoromethoxybenzaldehyde (1.95 mL, 13.6 mmol) and sodium triacetoxyborohydride (4.06 g, 18.2 mmol). The mixture is stirred for 2 hours, diluted with aqueous sodium bicarbonate and extracted with dichloromethane (3×). The combined organic phase is washed with water and brine, dried over sodium sulfate, concentrated in vacuo and the crude material is purified by flash chromatography (ethyl acetate/hexanes gradient) to afford 2-bromo-5-(1-(4-(trifluoromethoxy)benzyl)azetidin-3-yloxy)pyrazine A4b as a white solid: MS calcd. for C$_{15}$H$_{14}$BrF$_3$N$_3$O$_2$ ([M+H]$^+$): 404.0, found: 404.0.

Step C: A mixture of Intermediate A4b (2.84 g, 7.03 mmol), tris(dibenzylideneacetone)dipalladium (322 mg, 0.35 mmol), 9,9-dimethyl-4,5-bis(diphenylphosphino)xanthene (407 mg, 0.70 mmol), cesium carbonate (6.87 g, 21.1 mmol) and tert-butyl 3-oxopiperazine-1-carboxylate (1.69 g, 8.43 mmol) is evacuated, set under nitrogen and treated with dioxane (35 mL). The resulting mixture is heated to 120° C. for 3 hours. The mixture is filtered over Celite and concentrated in vacuo. The crude material is purified by flash chromatography (ethyl acetate/hexanes gradient) to afford tert-butyl 3-oxo-4-(5-(1-(4-(trifluoromethoxy)benzyl)azetidin-3-yloxy)pyrazin-2-yl)piperazine-1-carboxylate A4c: MS calcd. for C$_{24}$H$_{29}$F$_3$N$_5$O$_5$ ([M+H]$^+$): 524.2, found: 524.0.

Step D: A solution of Intermediate A4c (2.16 mg, 4.13 mmol) in dichloromethane (20 mL) is treated with trifluoroacetic acid (10 mL) and stirred at room temperature for 15 minutes. The solvent is evaporated. The crude material is dissolved with dichloromethane, treated with aqueous sodium bicarbonate to pH 8-9 and the phase is separated. The aqueous layer is extracted with dichloromethane (2×). the combined organic phase is dried over sodium sulfate and concentrated in vacuo to afford 1-(5-(1-(4-(trifluoromethoxy)benzyl)azetidin-3-yloxy)pyrazin-2-yl)piperazin-2-one A4d: MS calcd. for C$_{19}$H$_{21}$F$_3$N$_5$O$_3$ ([M+H]$^+$): 424.1, found: 4242.1. The product is used without purification.

Step E: A solution of Intermediate A4d in dichlorometane (40 mL) is treated with ethyldiisopropylamine (1.1 mL, 6.2 mmol) followed by methanesulfonyl chloride (0.5 mL, 6.2 mmol). The mixture is then stirred for 1 hour, then quenched with water and extracted with dichloromethane (3×). The combined organic phase is washed with brine, dried over sodium sulfate and concentrated in vacuo. The crude material is purified by flash chromatography (ethyl acetate/hexanes gradient) to afford the title compound (Example A4): $^1$H-NMR (400 MHz, CDCl$_3$) δ=8.63 (d, J=1.2 Hz, 1H), 8.04 (d, J=1.2 Hz, 1H), 7.32 (d, J=8.4 Hz, 2H), 7.16 (d, J=8.4 Hz, 2H), 5.28 (quint, J=5.6 Hz, 1H), 4.12 (s, 2H), 4.08-4.06 (m, 2H), 3.84-3.80 (m, 2H), 3.70 (s, 2H), 3.67-3.65 (m, 2H), 3.22-3.19 (m, 2H), 2.92 (s, 3H); $^{19}$F-NMR (376.46 MHz, CDCl3) δ=−57.87; MS calcd. for C$_{20}$H$_{23}$F$_3$N$_5$O$_5$S ([M+H]$^+$): 502.1, found: 502.1.

Example A5

4-(3,5-Difluoro-4-(1-(4-(trifluoromethyl)benzyl)azetidin-3-yloxy)phenyl)-1-(methylsulfonyl)piperidineine

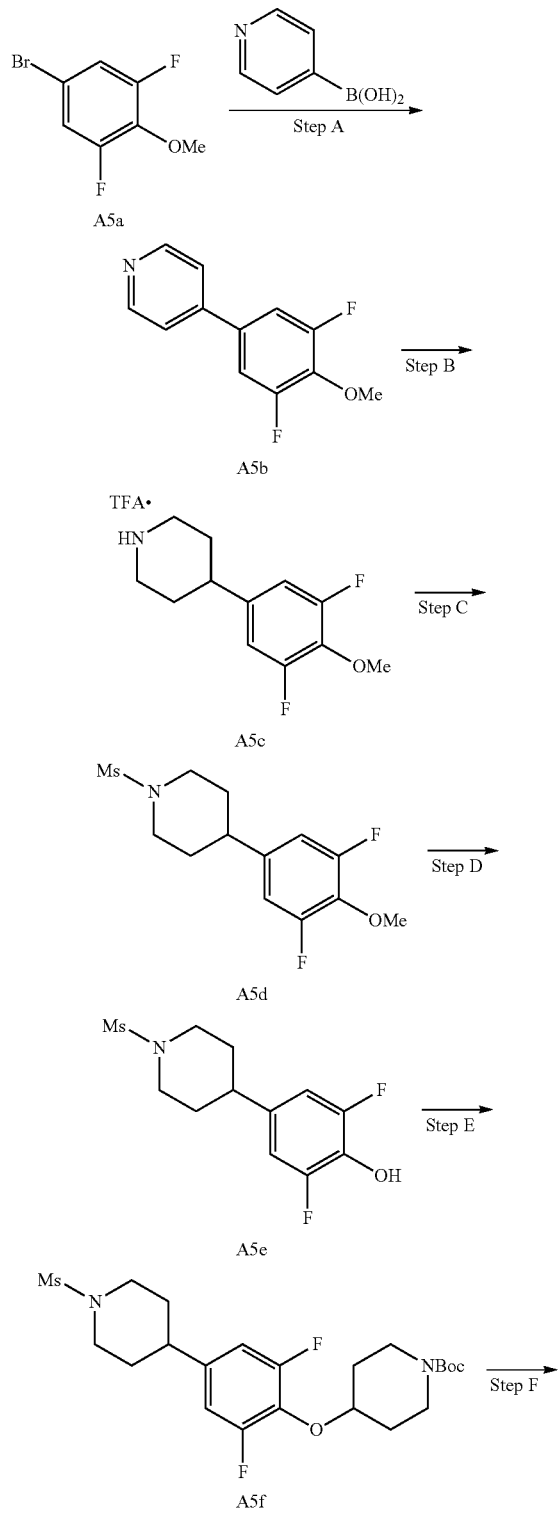

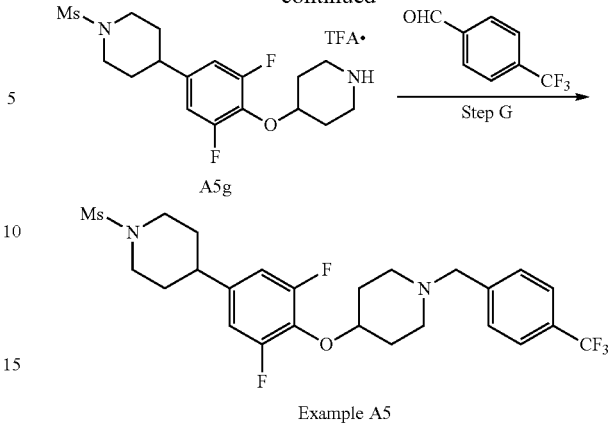

Example A5

Step A: In a microwave vial, a mixture of pyridin-4-ylboronic acid (160 mg, 1.3 mmol), 5-bromo-1,3-difluoro-2-methoxybenzene A5a (223 mg, 1 mmol) and Pd(PPh$_3$)$_4$ (58 mg, 0.05 mmol) is dissolved/suspended in dimethylformamide (3 mL). To the mixture are added cesium carbonate (978 mg, 3 mmol) and water (3 mL). The vial is sealed and subjected to microwave irradiation (150° C., 15 min). The mixture is filtered through a syringe filter and washed with ethyl acetate. Water is added and the mixture extracted with ethyl acetate (4×). The organic phase is dried over sodium sulfate and concentrated. The crude material is purified by flash chromatography (ethyl acetate/hexanes gradient) to afford 4-(3,5-difluoro-4-methoxyphenyl)pyridine A5b as a white solid: $^1$H-NMR (400 MHz, CDCl$_3$) δ 8.69 (d, J=6 Hz, 2H), 7.44 (d, J=6 Hz, 2H), 7.22 (d, J=9.6 Hz, 2H), 4.09 (s, 3H); MS calcd. for C$_{12}$H$_{10}$F$_2$NO ([M+H]$^+$): 222.1, found: 222.1.

Step B: To a solution of Intermediate A5b (10 g, 45.2 mmol) in acetic acid (500 ml) and trifluoroacetic acid (10 ml) is added platinum oxide (2 g, 8.8 mmol) and the mixture is stirred under an atmosphere of hydrogen for 7 hours. The catalyst is filtered through celite, washed with acetic acid, and concentrated under reduced pressure. The remaining contents are co-evaporated with ethanol/toluene to afford 4-(3,5-difluoro-4-methoxyphenyl)piperidine A5c as a white powder: $^1$H-NMR (400 MHz, CDCl$_3$) δ=6.80-6.73 (m, 2H), 3.97 (s, 3H), 3.53-3.50 (m, 2H), 3.04-2.95 (m, 2H), 2.72-2.68 (quint, J=8.0 Hz, 1H), 2.04-2.00 (m, 4H); $^{19}$F-NMR (376.46 MHz, CDCl$_3$) δ=−127.70; MS calcd. for C$_{12}$H$_{16}$F$_2$NO ([M+H]$^+$): 228.1, found: 228.1.

Step C: To a solution of Intermediate A5c (13 g, 38.1 mmol) in dichloromethane (120 ml) is added triethylamine (16 ml, 115 mmol). The flask is cooled to 0° C. and methanesulfonyl chloride (3.6 ml, 46 mmol) is added and stirred for 15 minutes after which time the flask is warmed to 23° C. and stirred for an additional 15 minutes. Saturated aqueous sodium bicarbonate (40 ml) is added and the organic layer is separated. The organic layer is washed with water, 0.1 M HCl, water, saturated aqueous sodium bicarbonate and dried over magnesium sulfate. The solvent is evaporated and the crude material is recrystallized from toluene to afford 4-(3,5-difluoro-4-methoxyphenyl)-1-(methylsulfonyl)piperidine A5d as a white powder: $^1$H-NMR (400 MHz, CDCl$_3$) δ=6.77-6.71 (m, 2H), 3.97-3.91 (m, 5H), 2.81 (s, 3H), 2.78-2.71 (m, 2H), 2.57-2.49 (m, 1H), 1.95-1.91 (m, 2H), 1.80-1.70 (m, 2H); $^{19}$F-NMR (376.46 MHz, CDCl$_3$) δ=−128.28; MS calcd. for C$_{13}$H$_{18}$F$_2$NO$_3$S ([M+H]$^+$): 306.1, found: 306.1.

Step D: To a solution of Intermediate A5d (10.3 g, 33.7 mmol) in dichloromethane (150 ml) at 0° C. is added a solution of boron tribromide (3.9 ml, 40.44 mmol) in dichloromethane (20 ml) and the mixture is stirred for 15 minutes. After warming to room temperature and stirring for 1 hour, additional boron tribromide (0.5 ml, 5 mmol) is added and the mixture is stirred for 15 minutes. The reaction is quenched with methanol and the mixture is concentrated in vacuo. Ethyl acetate is added and the organic layer is washed with water, saturated aqueous sodium bicarbonate and brine, dried over magnesium sulfate and concentrated in vacuo to afford 2,6-difluoro-4-(1-(methylsulfonyl)piperidin-4-yl)phenol A5e as a white solid: $^1$H-NMR (400 MHz, D$_6$-DMSO) δ=9.93 (s, 1H), 7.00-6.93 (m, 2H), 3.65-3.62 (m, 2H), 2.89 (s, 3H), 2.79-2.73 (m, 2H), 2.59-2.52 (m, 1H), 1.84-1.81 (m, 2H), 1.66-1.56 (m, 2H); $^{19}$F-NMR (376.46 MHz, D$_6$-DMSO) δ=−132.39; MS calcd. for C$_{12}$H$_{16}$F$_2$NO$_3$S ([M+H]$^+$): 292.1, found: 292.1.

Step E: A solution of Intermediate A5e (2.04 g, 7.0 mmol) in dimethylsulfoxide (40 mL) is treated with potassium tert-butoxide (1.26 g, 11.2 mmol) and the mixture is stirred at room temperature for 20 minutes. Solid tert-butyl 4-(methylsulfonyloxy)piperidine-1-carboxylate (2.93 g, 10.5 mmol) is then added and the mixture is stirred at 100° C. for 15 h. The mixture is cooled to room temperature, diluted with water, stirred for 1 h, the precipitate filtered, washed with water and dried. The crude material is purified by flash chromatography (ethyl acetate/hexanes gradient) to afford tert-butyl 4-(2,6-difluoro-4-(1-(methylsulfonyl)piperidin-4-yl)phenoxy)piperidine-1-carboxylate A5f as a white solid: $^1$H-NMR (400 MHz, CDCl$_3$) δ=6.75 (m, 2H), 4.30 (m, 1H), 3.94 (m, 2H), 3.76 (ddd, J=13.4, 7.1, 3.8 Hz, 2H), 3.27 (ddd, J=13.6, 7.8, 3.9 Hz, 2H), 2.82 (s, 3H), 2.75 (m, 2H), 2.54 (tt, J=14.2, 3.6 Hz, 1H), 1.84-1.94 (m, 4H), 1.70-1.80 (m, 4H), 1.46 (s, 9H); $^{19}$F-NMR (376.46 MHz, CDCl$_3$) δ=−126.55; MS calcd. for C$_{22}$H$_{32}$F$_2$N$_2$NaO$_5$S ([M+Na]$^+$): 497.2, found: 497.1.

Step F: A solution of Intermediate A5f (2.04 g, 4.30 mmol) in dichloromethane (40 mL) is treated with trifluoroacetic acid (20 mL) and stirred at room temperature for 15 hours. The solvent is evaporated, the remaining contents are co-evaporated with dichloromethane twice and recrystallized from ethylacetate-hexanes to afford 4-(3,5-difluoro-4-(piperidin-4-yloxy)phenyl)-1-(methylsulfonyl)piperidine trifluoroacetate A5g as a white crystalline compound. MS calcd. for C$_{17}$H$_{25}$F$_2$N$_2$O$_3$S ([M+H]$^+$): 375.2, found: 375.1.

Step G: A solution of Intermediate A5g (47 mg, 0.132 mmol) and 4-(trifluoromethyl)benzaldehyde (20 μL) in dichloromethane (2 mL) is treated with sodium triacetoxyborohydride (83 mg, 0.39 mmol). The mixture is then stirred at room temperature for 16 hours, treated with aqueous solution of sodium bicarbonate, stirred for 15 minutes, extracted with dichloromethane (×3) and dried over sodium sulfate. The crude material is purified by flash chromatography (ethyl acetate/hexanes gradient) to afford the title compound (Example A5) as a white solid. $^1$H-NMR (400 MHz, DMSO-d$_6$) δ=7.68 (m, 2H), 7.54 (m, 2H), 7.09 (m, 2H), 4.11 (m, 1H), 3.65 (m, 2H), 3.56 (s, 2H), 2.89 (s, 3H), 2.76 (m, 2H), 2.56-2.70 (m, 3H), 2.19 (m, 2H), 1.86 (m, 4H), 1.58-1.73 (m, 4H); MS calcd. for C$_{25}$H$_{30}$F$_5$N$_2$O$_3$S ([M+H]$^+$): 533.2, found: 533.2.

Example A6

2-(4-(methylsulfonyl)piperazin-1-yl)-5-(1-(4-(trifluoromethyl)benzyl)azetidin-3-yloxy)pyrazine

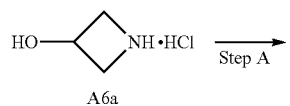

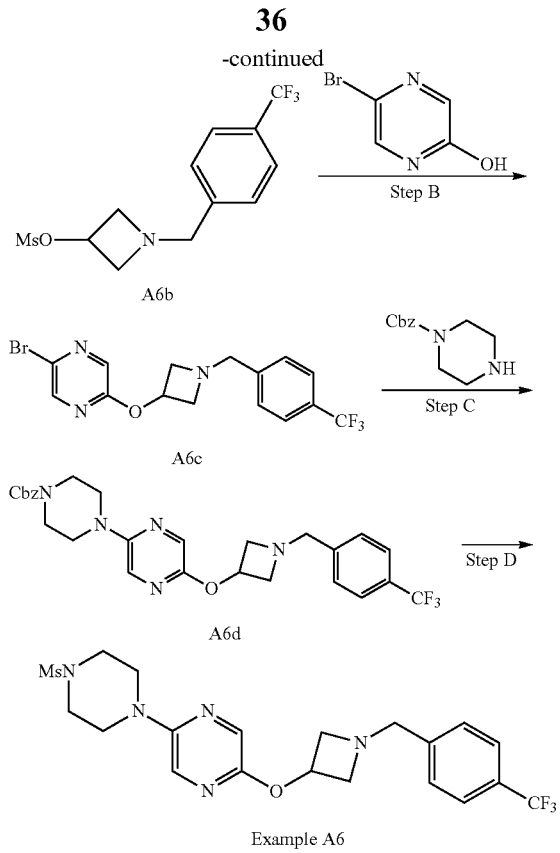

Step A: A solution of 3-hydroxyazetidine hydrochloride A6a (1.4 g, 14.8 mmol) and 4-trifluoromethylbenzaldehyde (1.98 mL, 14.8 mmol) in dichloroethane (50 mL) is treated with ethyldiisopropylamine (2.56 mL, 14.8 mmol) and heated to 80° C. for 1 hour. The mixture is then cooled to room temperature and sodium triacetoxyborohydride (6.2 g, 29.6 mmol) is added and the mixture is stirred at room temperature for 16 hours. The reaction is treated with saturated sodium hydrogencarbonate solution e (50 mL), and extracted with dichloromethane (3×20 mL). The organics are isolated and dried over magnesium sulfate, filtered, and concentrated in vacuo. The residue is dissolved in dichloromethane (100 mL), cooled to 0° C. and treated with ethyldiisopropylamine (3.3 mL, 19.2 mmol) and methanesulfonyl chloride (1.5 mL, 19.2 mmol). The mixture is stirred at room temperature for 1 hour, diluted with saturated sodium bicarbonate (50 mL) and separated. The organic phase is dried over magnesium sulfate, filtered, concentrated and the crude material is purified by flash chromatography (dichloromethane/methanol gradient) to afford 1-(4-(trifluoromethyl)benzyl)azetidin-3-yl methanesulfonate A6b: $^1$H-NMR (CDCl$_3$, 400 MHz) δ 7.51 (d, J=8.0 Hz, 2H), 7.32 (d, J=8.0 Hz, 2H), 5.04 (m, 1H), 3.69 (m, 2H), 3.67 (s, 2H), 3.22 (m, 2H), 2.95 (s, 3H); MS calcd. for C$_{12}$H$_{15}$F$_3$NO$_3$S ([M+H]$^+$): 310.1, found: 310.1.

Step B: A 20 mL vial charged with Intermediate A6b (530 mg, 1.71 mmol), 5-bromopyrazin-2-ol (298 mg, 1.71 mmol), cesiumcarbonate (1.1 g, 3.42 mmol) and acetonitrile (10 mL) is heated to 80° C. for 12 hours. The reaction is then filtered, concentrated in vacuo and the crude material is purified by flash chromatography (ethyl acetate/hexane gradient) to afford 2-bromo-5-(1-(4-(trifluoromethyl)benzyl)azetidin-3-yloxy)pyrazine A6c as a colorless oil: $^1$H-NMR (CDCl$_3$, 400 MHz) δ 8.15 (d, J=1.2 Hz, 1H), 8.05 (d, J=1.2 Hz, 1H), 7.60 (d, J=8.0 Hz, 2H), 7.43 (d, J=8.0 Hz, 2H), 5.24 (m, 1H), 3.83

(m, 2H), 3.77 (s, 2H), 3.21 (m, 2H); MS calcd. for $C_{15}H_{14}BrF_3N_3O$ ([M+H]$^+$): 388.0, found: 388.0.

Step C: A 20 mL vial charged with Intermediate A6c (228 mg, 0.59 mmol), tris(dibenzylideneacetone)dipalladium (11 mg, 0.012 mmol), 9,9-dimethyl-4,5-bis(diphenylphosphino) xanthene (20 mg, 0.035 mmol) and benzyl piperazine-1-carboxylate (136 µL, 0.704 mmol) is treated with dry toluene (20 mL), purged with nitrogen for 15 minutes, treated with sodium terbutoxide (85 mg, 0.88 mmol) and heated to 100° C. for 12 hours. The reaction is then cooled to room temperature, diluted with water and ethyl acetate. The organics are separated, washed with saturated aqueous sodium hydrogencarbonate solution, dried over magnesium sulfate, filtered, evaporated and the crude material is purified by flash chromatography (dichloromethane/methanol gradient) to afford benzyl 4-(5-(1-(4-(trifluoromethyl)benzyl)azetidin-3-yloxy) pyrazin-2-yl)piperazine-1-carboxylate A6d: MS calcd. for $C_{27}H_{29}F_3N_5O_3$ ([M+H]$^+$): 528.2, found: 528.2.

Step D: To a solution of Intermediate A6d (253 mg, 0.48 mmol) in methanol (10 mL) is added palladium on carbon (5%, 50 mg). The mixture is then saturated with hydrogen and subjected to hydrogenolysis (1 atm) overnight. The mixture is then filtered through Celite and washed with methanol. The solvent is evaporated and the residue is dissolved in dichloromethane, treated with ethyldiisopropylamine (106 µL, 0.62 mmol) and cooled to 0° C. (ice/water bath). The reaction is then treated with methanesulfonyl chloride (30 µL, 0.37 mmol) and stirred for 2 hours. The reaction is concentrated and purified on a reversed phase HPLC (water/acetonitrile gradient) to provide the title compound (Example A6): $^1$H-NMR (400 MHz, CDCl$_3$) δ 7.81 (d, J=1.2 Hz, 1H), 7.52 (m, 3H), 7.38 (d, J=8.0 Hz, 2H), 5.12 (m, 1H), 3.85 (m, 2H), 3.76 (s, 2H), 3.47 (m, 4H), 3.29 (m, 4H), 3.20 (m, 2H), 2.75 (s, 3H); MS calcd. for $C_{20}H_{25}F_3N_5O_3S$ ([M+H]$^+$): 472.2, found: 472.2.

Example A7

4-(3,5-difluoro-4-(1-(4-(trifluoromethyl)benzyl)azetidin-3-yloxy)phenyl)-1-(methylsulfonyl)piperidineine

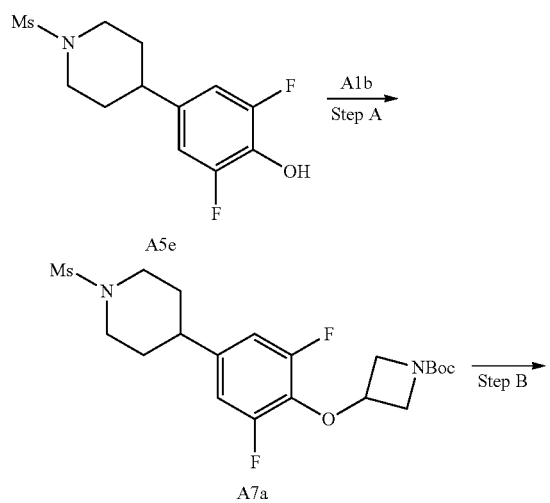

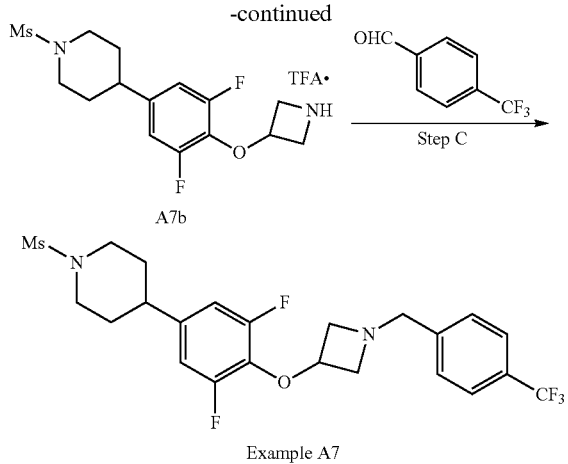

Example A7

Step A: A solution of Intermediate A5e (3.19 g, 11.0 mmol) in dimethylsulfoxide (44 mL) is treated with potassium terbutoxide (1.6 g, 14.3 mmol) and the mixture is stirred at room temperature for 20 minutes. A solution of Intermediate A1b (3.30 g, 13.2 mmol) in dimethylsulfoxide (22 mL) is then added dropwise and the mixture is stirred at 100° C. for 3 days. The mixture is cooled to room temperature, diluted with water and extracted with ethyl acetate (3×). The combined organic phases are then washed with brine, dried over sodium sulfate and concentrated in vacuo. The crude material is purified by flash chromatography (ethyl acetate/hexanes gradient) to afford tert-butyl 3-(2,6-difluoro-4-(1-(methylsulfonyl)piperidin-4-yl)phenoxy)azetidine-1-carboxylate A7a as a white solid: $^1$H-NMR (400 MHz, CDCl$_3$) δ=6.78-6.73 (m, 2H), 4.91-4.861 (m, 1H), 4.21-4.17 (m, 2H), 4.11-4.08 (m, 2H), 3.95-3.91 (m, 2H), 2.81 (s, 3H), 2.78-2.71 (m, 2H), 2.58-2.51 (m, 1H), 1.98-1.91 (m, 2H), 1.79-1.69 (m, 2H), 1.44 (s, 9H); $^{19}$F-NMR (376.46 MHz, CDCl$_3$) δ=−127.66; MS calcd. for $C_{20}H_{28}F_2N_2O_5S$ ([M+H]$^+$): 447.1, found: 447.1.

Step B: A solution of Intermediate A7a (125 mg, 0.280 mmol) in dichloromethane (2 ml) is treated with trifluoroacetic acid (1 ml) and stirred at room temperature for 1.5 hours. The solvent is evaporated and the remaining contents are co-evaporated with toluene and methanol to afford 4-(4-(azetidin-3-yloxy)-3,5-difluorophenyl)-1-(methylsulfonyl)piperidine A7b as a yellow gum. MS calcd. for $C_{15}H_{21}F_2N_2O_3S$ ([M+H]$^+$): 347.1, found: 347.1. The compound is used without purification.

Step C: A solution of Intermediate A7b (33 mg, 0.072 mmol) in dimethylformamide (1.5 mL) is treated with 4-(trifluoromethyl)benzaldehyde (19 µL, 0.142 mmol), triethylamine (40 µL, 0.285 mmol) and macroporous sodium triacetoxyborohydride (2.31 mmol/g, 102 mg, 0.237 mmol). The mixture is then stirred at room temperature for 16 hours, filtered through an HPLC filter and the solvent is evaporated in vacuo. The crude material is purified by flash chromatography (ethyl acetate/hexanes gradient) to afford the title compound (Example A7) as a white solid. $^1$H-NMR (400 MHz, CDCl$_3$) δ=7.56 (d, J=8.4 Hz, 2H), 7.40 (d, J=8.0 Hz, 2H), 6.76-6.70 (m, 2H), 4.77 (quint, J=5.6 Hz, 1H), 3.94-3.90 (m, 2H), 3.74-3.70 (m, 4H), 3.27-3.23 (m, 2H), 2.81 (s, 3H), 2.77-2.70 (m, 2H), 2.56-2.49 (m, 1H), 1.93-1.90 (m, 2H), 1.78-1.68 (m, 2H); $^{19}$F-NMR (376.46 MHz, CDCl$_3$) δ=−62.64, −127.60; MS calcd. for $C_{23}H_{26}F_5N_2O_3S$ ([M+H]$^+$): 505.1, found: 505.1.

By repeating the procedure described in the above Examples A1-A7, using appropriate starting materials, the following compounds of Formula I, as identified in Table 1, are obtained:

TABLE 1

| Example # | Structure | NMR and/or ESMS |
|---|---|---|
| A8 | Ms-piperazine-pyridine-O-azetidine-CH2-C6H4-OCF3 | $^1$H-NMR (400 MHz, CDCl$_3$) δ = 7.80 (d, J = 2.8 Hz, 1H), 7.33 (d, J = 8.0 Hz, 2H), 7.19 (d, J = 8.0 Hz, 2H), 7.09 (dd, J = 8.8, 2.8 Hz, 1H), 6.66 (d, J = 8.8 Hz, 1H), 4.77 (quint, J = 6.0 Hz, 1H), 3.82-3.78 (m, 2H), 3.71 (s, 2H), 3.59-3.55 (m, 4H), 3.37-3.34 (m, 4H), 3.20-3.16 (m, 2H), 2.83 (s, 3H); $^{19}$F-NMR (376.5 MHz, CDCl$_3$) δ = −58.88; MS calcd. for C$_{21}$H$_{26}$F$_3$N$_4$O$_4$S ([M + H]$^+$): 487.2, found: 487.2. |
| A9 | Ms-piperazine-pyridine-O-azetidine-CH2-C6H4-CF3 | $^1$H-NMR (400 MHz, CDCl$_3$) δ = 7.71 (d, J = 2.8 Hz, 1H), 7.51 (d, J = 8.0 Hz, 2H), 7.34 (d, J = 8.0 Hz, 2H), 7.00 (dd, J = 9.2, 3.2 Hz, 1H), 6.57 (d, J = 9.2 Hz, 1H), 4.69 (quint, J = 6.0 Hz, 1H), 3.74-3.67 (m, 2H), 3.68 (s, 2H), 3.49-3.46 (m, 4H), 3.27-3.25 (m, 4H), 3.13-3.09 (m, 2H), 2.74 (s, 3H); $^{19}$F-NMR (376.5 MHz, CDCl$_3$) δ = −62.44; MS calcd. for C$_{21}$H$_{26}$F$_3$N$_4$O$_3$S ([M + H]$^+$): 471.2, found: 471.2. |
| A10 | Cbz-piperazine-pyrazine-O-azetidine-CH2-C6H4-iPr | $^1$H-NMR (400 MHz, CDCl$_3$) δ = 7.88 (d, J = 1.6 Hz, 1H), 7.59 (d, J = 1.6 Hz, 1H), 7.40-7.33 (m, 5H), 7.24-7.18 (m, 4H), 5.18 (s, 2H), 5.16 (quint, J = 6.0 Hz, 1H), 3.84-3.79 (m, 2H), 3.68 (s, 2H), 3.68-3.64 (m, 4H), 3.43-3.38 (m, 4H), 3.19-3.15 (m, 2H), 3.91 (septet, J = 7.2 Hz, 1H), 1.26 (d, J = 6.8 Hz, 6H); MS calcd. for C$_{29}$H$_{36}$N$_5$O$_3$ ([M + H]$^+$): 502.3, found: 502.3. |
| A11 | Ms-piperazine-pyrazine-O-azetidine-CH2-C6H4-iPr | $^1$H-NMR (400 MHz, CDCl$_3$) δ = 7.80 (d, J = 1.2 Hz, 1H), 7.53 (d, J = 1.6 Hz, 1H), 7.12 (q, J = 8.0 Hz, 4H), 5.08 (quint, J = 5.6 Hz, 1H), 3.74-3.70 (m, 2H), 3.59 (s, 2H), 3.47-3.44 (m, 4H), 3.30-3.27 (m, 4H), 3.10-3.06 (m, 2H), 3.82 (septet, J = 6.8 Hz, 1H), 2.75 (s, 3H), 1.17 (d, J = 6.8 Hz, 6H); MS calcd. for C$_{22}$H$_{32}$N$_5$O$_3$S ([M + H]$^+$): 446.2, found: 446.2. |
| A12 | Ms-piperazine-pyridine-O-azetidine-CH2-C6H4-OMe | $^1$H-NMR (400 MHz, CDCl$_3$) δ = 7.77 (d, J = 3.2 Hz, 1H), 7.19 (d, J = 8.4 Hz, 2H), 7.06 (dd, J = 9.2, 3.2 Hz, 1H), 6.65 (d, J = 8.4 Hz, 2H), 6.63 (d, J = 8.8 Hz, 1H), 4.73 (quint, J = 6.0 Hz, 1H), 3.79 (s, 3H), 3.76-3.72 (m, 2H), 3.61 (s, 2H), 3.53 (t, J = 4.8 Hz, 4H), 3.32 (t, J = 5.2 Hz, 4H), 3.14-3.10 (m, 2H), 2.80 (s, 3H); MS calcd. for C$_{21}$H$_{29}$N$_4$O$_4$S ([M + H]$^+$): 433.1, found: 433.1. |

TABLE 1-continued

| Example # | Structure | NMR and/or ESMS |
|---|---|---|
| A13 | Ms–N–piperazine–pyridine–O–azetidine–N–CH2–C6H4–OCHF2 | $^1$H-NMR (400 MHz, CDCl$_3$) δ = 7.78 (d, J = 3.2 Hz, 1H), 7.27 (d, J = 8.4 Hz, 2H), 7.08-7.05 (m, 3H), 6.65 (t, J = 10.4 Hz, 1H), 4.74 (quint, J = 6.0 Hz, 1H), 3.78-3.74 (m, 2H), 3.66 (s, 2H), 3.54 (t, J = 4.8 Hz, 4H), 3.32 (t, J = 5.2 Hz, 4H), 3.16-3.12 (m, 2H), 2.80 (s, 3H); $^{19}$F-NMR (376.46 MHz, CDCl3) δ = −80.67; MS calcd. for C$_{21}$H$_{27}$F$_2$N$_4$O$_3$S ([M + H]$^+$): 453.1, found: 453.1. |
| A14 | Ms–N–piperazine–pyridine–O–azetidine–N–CH2–C6H4–Me | $^1$H-NMR (400 MHz, CDCl$_3$) δ = 7.77 (d, J = 3.2 Hz, 1H), 7.15 (q, J = 6.0 Hz, 4H), 7.05 (dd, J = 9.2, 3.2 Hz, 1H), 6.63 (d, J = 8.8 Hz, 1H), 4.73 (quint, J = 6.0 Hz, 1H), 3.78-3.74 (m, 2H), 3.64 (s, 2H), 3.53 (t, J = 4.8 Hz, 4H), 3.32 (t, J = 5.2 Hz, 4H), 3.15-3.11 (m, 2H), 2.80 (s, 3H), 2.33 (s, 3H); MS calcd. for C$_{21}$H$_{29}$N$_4$O$_3$S ([M + H]$^+$): 417.1, found: 417.1. |
| A15 | Ms–N–piperazine–pyridine–O–azetidine–N–CH2–C6H4–Cl | $^1$H-NMR (400 MHz, CDCl$_3$) δ = 7.77 (d, J = 3.2 Hz, 1H), 7.28 (d, J = 8.4 Hz, 2H), 7.21 (d, J = 8.4 Hz, 2H), 7.06 (dd, J = 9.2, 3.2 Hz, 1H), 6.63 (d, J = 8.8 Hz, 1H), 4.73 (quint, J = 6.0 Hz, 1H), 3.77-3.74 (m, 2H), 3.64 (s, 3H), 3.54 (t, J = 4.8 Hz, 4H), 3.33 (t, J = 5.2 Hz, 4H), 3.15-3.12 (m, 2H), 2.80 (s, 3H); MS calcd. for C$_{20}$H$_{26}$ClN$_4$O$_3$S ([M + H]$^+$): 437.1, found: 437.1. |
| A16 | Ms–N–piperazine–pyridine–O–azetidine–N–CH2–C6H4–CF3 (meta) | $^1$H-NMR (400 MHz, CDCl$_3$) δ = 7.78 (d, J = 3.2 Hz, 1H), 7.55-7.41 (m, 4H), 7.06 (dd, J = 9.2, 3.2 Hz, 1H), 6.64 (d, J = 8.8 Hz, 1H), 4.75 (quint, J = 6.0 Hz, 1H), 3.81-3.74 (m, 2H), 3.74 (s, 2H), 3.53 (t, J = 4.8 Hz, 4H), 3.32 (t, J = 5.2 Hz, 4H), 3.19-3.15 (m, 2H), 2.80 (s, 3H); $^{19}$F-NMR (376.46 MHz, CDCl3) δ = −62.54; MS calcd. for C$_{21}$H$_{26}$F$_3$N$_4$O$_3$S ([M + H]$^+$): 471.1, found: 471.1. |
| A17 | Ms–N–(3-oxopiperazine)–pyridine–O–azetidine–N–CH2–C6H4–CF3 | $^1$H-NMR (400 MHz, CDCl$_3$) δ = 7.96 (d, J = 3.2 Hz, 1H), 7.75 (d, J = 8.8 Hz, 1H), 7.58 (d, J = 8.0 Hz, 2H), 7.41 (d, J = 8.0 Hz, 2H), 7.12 (dd, J = 8.8, 2.8 Hz, 1H), 4.83 (quint, J = 5.6 Hz, 1H), 4.13-4.09 (m, 4H), 3.84-3.80 (m, 2H), 3.75 (s, 2H), 3.65-3.63 (m, 2H), 3.22-3.18 (m, 2H), 2.91 (s, 3H); MS calcd. for C$_{21}$H$_{24}$F$_3$N$_4$O$_4$S ([M + H]$^+$): 485.1, found: 485.1. |

TABLE 1-continued

| Example # | Structure | NMR and/or ESMS |
|---|---|---|
| A18 | 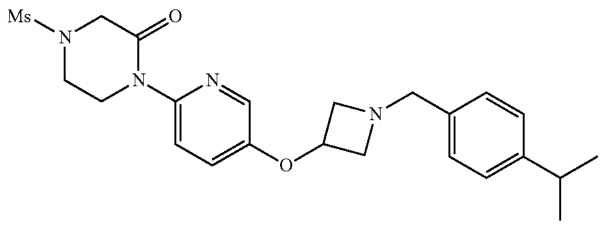 [SMILES: CC(C)c1ccc(CN2CC(Oc3ccc(N4CCN(S(C)(=O)=O)CC4=O)nc3)C2)cc1] | $^1$H-NMR (400 MHz, CDCl$_3$) δ = 7.96 (d, J = 2.8 Hz, 1H), 7.74 (d, J = 9.2 Hz, 1H), 7.22-7.17 (m, 4H), 7.12 (dd, J = 8.8, 2.8 Hz, 1H), 4.83 (quint, J = 5.6 Hz, 1H), 4.12-4.09 (m, 4H), 3.82-3.80 (m, 2H), 3.67-3.63 (m, 4H), 2.95 (s, 1H), 2.92-2.87 (m. 5H), 1.23 (d, J = 7.2 Hz, 6H); MS calcd. for C$_{23}$H$_{31}$N$_4$O$_4$S ([M + H]$^+$): 459.2, found: 459.2. |
| A19 | 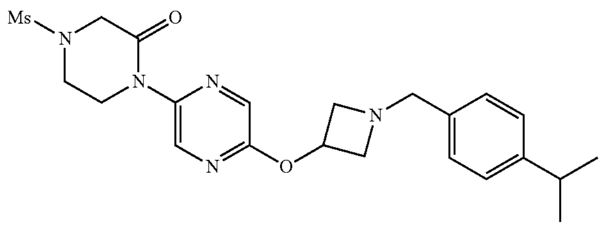 [SMILES: CC(C)c1ccc(CN2CC(Oc3cnc(N4CCN(S(C)(=O)=O)CC4=O)cn3)C2)cc1] | $^1$H-NMR (400 MHz, CDCl$_3$) d = 8.63 (d, J = 1.2 Hz, 1H), 8.04 (d, J = 1.6 Hz, 1H), 7.22-7.17 (m, 4H), 5.26 (quint, J = 5.6 Hz, 1H), 4.12 (s, 2H), 4.08-4.06 (m, 2H), 3.85-3.81 (m, 2H), 3.68-3.64 (m, 4H), 3.23-3.20 (m, 2H), 2.92 (s, 3H), 2.88 (septet, J = 6.8 Hz, 1H), 1.23 (d, J = 6.8 Hz, 6H); MS calcd. for C$_{22}$H$_{30}$N$_5$O$_4$S ([M + H]$^+$): 460.1, found: 460.1. |
| A20 | 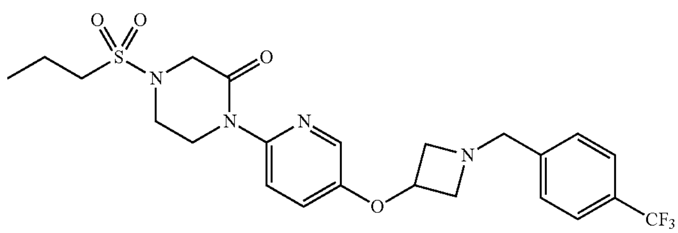 [SMILES: CCCS(=O)(=O)N1CCN(c2ccc(OC3CN(Cc4ccc(C(F)(F)F)cc4)C3)cn2)C(=O)C1] | $^1$H-NMR (400 MHz, CDCl$_3$) δ = 7.97 (d, J = 3.2 Hz, 1H), 7.74 (d, J = 9.2 Hz, 1H), 7.58 (d, J = 8.0 Hz, 2H), 7.41 (d, J = 8.0 Hz, 2H), 7.12 (dd, J = 8.8, 2.8 Hz, 1H), 4.84 (quint, J = 6.0 Hz, 1H), 4.12 (s, 2H), 4.10-4.07 (m, 2H), 3.84-3.80 (m, 2H), 3.75 (s, 2H), 3.69-3.66 (m, 2H), 3.22-3.18 (m, 2H), 3.01-2.97 (m, 2H), 1.93-1.83 (m, 2H), 1.08 (t, J = 7.6 Hz, 3H); $^{19}$F-NMR (376.46 MHz, CDCl$_3$) δ = −62.45; MS calcd. for C$_{23}$H$_{28}$F$_3$N$_4$O$_4$S ([M + H]$^+$): 513.1, found: 513.1. |
| A21 | 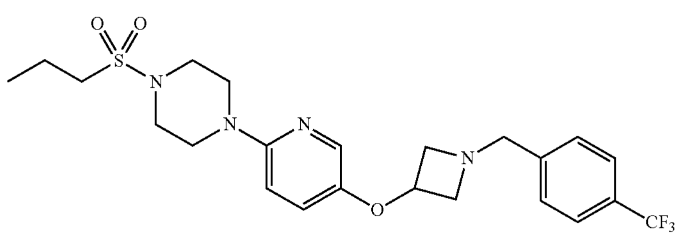 [SMILES: CCCS(=O)(=O)N1CCN(c2ccc(OC3CN(Cc4ccc(C(F)(F)F)cc4)C3)cn2)CC1] | $^1$H-NMR (400 MHz, CDCl$_3$) δ = 7.78 (d, J = 2.8 Hz, 1H), 7.68 (d, J = 8.0 Hz, 2H), 7.55 (d, J = 8.0 Hz, 2H), 7.05 (dd, J = 9.2, 3.2 Hz, 1H), 6.62 (d, J = 9.2 Hz, 1H), 5.02 (quint, J = 5.6 Hz, 1H), 4.46 (br s, 2H), 4.26 (br s, 2H), 3.72 (br s, 2H), 3.54-3.51 (m, 4H), 3.38-3.35 (m, 4H), 2.92-2.88 (m, 2H), 1.92-1.82 (m, 2H), 1.06 (t, J = 7.6 Hz, 3H); $^{19}$F-NMR (376.46 MHz, CDCl$_3$) δ = −62.90; MS calcd. for C$_{23}$H$_{30}$F$_3$N$_4$O$_3$S ([M + H]$^+$): 499.1, found: 499.1. |
| A22 | 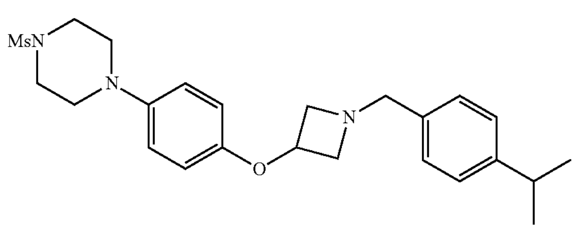 | $^1$H NMR (400 MHz, CDCl$_3$) δ = 7.21-7.16 (m, 4H), 6.87-6.84 (m, 2H), 6.73-6.70 (m, 2H), 4.74 (quint, J = 6.0 Hz, 1H), 3.81-3.78 (m, 2H), 3.65 (br s, 2H), 3.38-3.36 (m, 4H), 3.16-3.11 (m, 6H), 2.88 (septet, J = 6.8 Hz, 1H), 2.82 (s, 3H), 1.23 (d, J = 6.8 Hz, 6H); MS calcd. for C$_{24}$H$_{34}$F$_5$N$_3$O$_3$S ([M + H]$^+$): 444.2, found: 444.2. |

TABLE 1-continued

| Example # | Structure | NMR and/or ESMS |
|---|---|---|
| A23 | 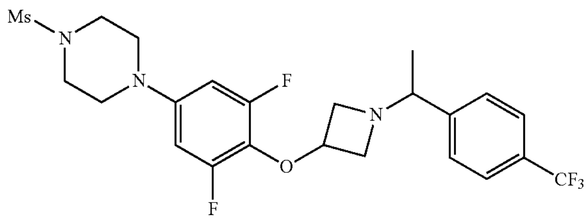 [SMILES: CC(c1ccc(C(F)(F)F)cc1)N1CC(Oc2c(F)cc(N3CCN(S(C)(=O)=O)CC3)cc2F)C1] | $^1$H NMR (400 MHz, CDCl$_3$) δ = 7.56 (d, J = 8.0 Hz, 2H), 7.42 (d, J = 8.0 Hz, 2H), 6.75-6.69 (m, 2H), 4.73 (quint, J = 6.0 Hz, 1H), 3.94-3.91 (m, 2H), 3.81-3.74 (m, 4H), 3.47-3.41 (m, 2H), 3.25-3.22 (m, 1H), 3.06-3.03 (m, 1H), 2.81 (s, 3H), 2.76-2.70 (m, 2H), 2.56-2.48 (m, 1H), 1.93-1.90 (m, 2H), 1.78-1.67 (m, 2H), 1.24 (d, J = 6.8 Hz, 3H); $^{19}$F NMR (376.46 MHz, CDCl$_3$) δ = −62.39, −127.59; MS calcd. for C$_{24}$H$_{28}$F$_5$N$_2$O$_3$S ([M + H]$^+$): 519.1, found: 519.1. |
| A24 | 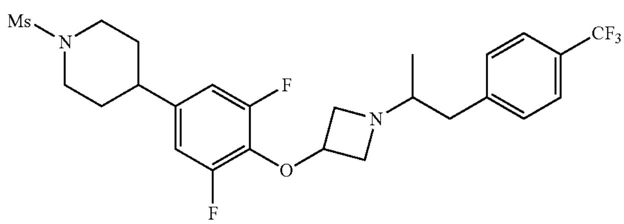 [SMILES: CC(Cc1ccc(C(F)(F)F)cc1)N1CC(Oc2c(F)cc(C3CCN(S(C)(=O)=O)CC3)cc2F)C1] | $^1$H NMR (400 MHz, CDCl$_3$) δ = 7.53 (d, J = 8.0 Hz, 2H), 7.27 (d, J = 8.0 Hz, 2H), 6.78-6.71 (m, 2H), 4.72 (quint, J = 6.0 Hz, 1H), 3.95-3.92 (m, 2H), 3.77-3.71 (m, 4H), 3.22-3.16 (m, 2H), 2.87-2.81 (m, 4H), 2.77-2.71 (m, 2H), 2.57-2.50 (m, 2H), 2.43-2.38 (m, 1H), 1.94-1.91 (m, 2H), 1.79-1.72 (m, 2H), 0.86 (d, J = 6.0 Hz, 3H); $^{19}$F NMR (376.46 MHz, CDCl$_3$) δ = −62.32, −127.58; MS calcd. for C$_{25}$H$_{30}$F$_5$N$_2$O$_3$S ([M + H]$^+$): 533.1, found: 533.1. |
| A25 | 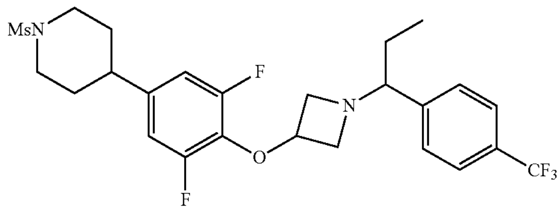 | $^1$H NMR (400 MHz, DMSO-d$_6$) δ = 7.68 (m, 2H), 7.49 (m, 2H), 7.09 (m, 2H), 4.69 (m, 1H), 3.64 (m, 3H), 3.30 (m, 2H), 3.12 (m, 1H), 2.95 (m, 1H), 2.88 (s, 3H), 2.75 (m, 2H), 2.61 (m, 1H), 1.83 (m, 2H), 1.37-1.75 (m, 4H), 0.61 (t, J = 7.4 Hz, 3H); MS calcd. for C$_{25}$H$_{30}$F$_5$N$_2$O$_3$S ([M + H]$^+$): 533.2, found: 533.2. |
| A26 | 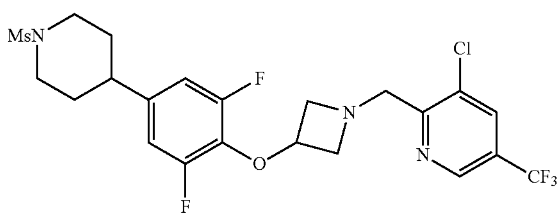 | $^1$H NMR (400 MHz, DMSO-d$_6$) δ = 8.09 (m, 1H), 8.44 (m, 1H), 7.10 (m, 2H), 4.73 (quint, J = 5.7 Hz, 1H), 3.93 (s, 2H), 3.70 (m, 2H), 3.64 (m, 2H), 3.32 (m, 2H), 2.89 (s, 3H), 2.76 (m, 2H), 2.62 (m, 1H), 1.84 (m, 2H), 1.64 (m, 2H); MS calcd. for C$_{22}$H$_{24}$ClF$_5$N$_3$O$_3$S ([M + H]$^+$): 540.1, found: 540.0. |
| A27 | 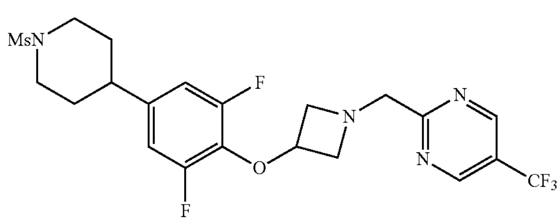 | $^1$H NMR (400 MHz, DMSO-d$_6$) δ = 9.23 (s, 2H), 7.11 (m, 2H), 4.76 (quint, J = 5.6 Hz, 1H), 3.96 (s, 2H), 3.75 (m, 2H), 3.65 (m, 2H), 3.35 (m, 2H), 2.89 (s, 3H), 2.76 (m, 2H), 2.62 (m, 1H), 1.83 (m, 2H), 1.64 (m, 2H); MS calcd. for C$_{21}$H$_{24}$F$_5$N$_4$O$_3$S ([M + H]$^+$): 507.1, found: 507.1. |

TABLE 1-continued

| Example # | Structure | NMR and/or ESMS |
|---|---|---|
| A28 | 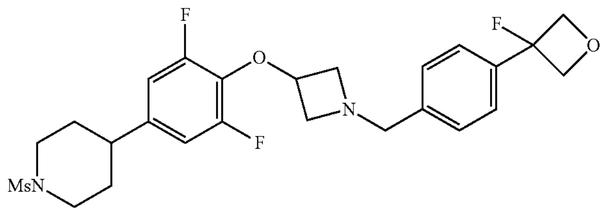 | $^1$H NMR (400 MHz, CDCl$_3$) δ = 7.50 (m, 2H), 7.36 (m, 2H), 6.73 (m, 2H), 5.10 (ddd, J = 21.2, 7.9, 1.1 Hz, 2H), 4.87 (ddd, J = 21.3, 7.9, 1.1 Hz, 2H), 4.77 (quint, J = 5.9 Hz, 1H), 3.93 (m, 2H), 3.72 (m, 4H), 3.25 (m, 2H), 2.82 (s, 3H), 2.74 (m, 2H), 2.53 (m, 1H), 1.92 (m, 2H), 1.74 (m, 2H); MS calcd. for C$_{25}$H$_{30}$F$_3$N$_2$O$_4$S ([M + H]$^+$): 511.2, found: 511.1. |
| A29 | Obtained by LiOH hydrolysis of OAc precursor | $^1$H NMR (400 MHz, DMSO-d$_6$) δ = 7.66 (m, 2H), 7.51 (m, 2H), 7.09 (m, 2H), 4.71 (m, 2H), 3.70 (t, J = 7.0 Hz, 1H), 3.64 (m, 2H), 3.53 (m, 1H), 3.35-3.45 (m, 3H), 3.23 (m, 1H), 3.00 (m, 1H), 2.89 (s, 3H), 2.76 (m, 2H), 2.61 (tt, J = 12.1, 3.4 Hz, 1H), 1.83 (m, 2H), 1.63 (m, 2H); MS calcd. for C$_{24}$H$_{27}$F$_5$N$_2$O$_4$S ([M + H]$^+$): 535.2, found: 535.1. |
| A30 | 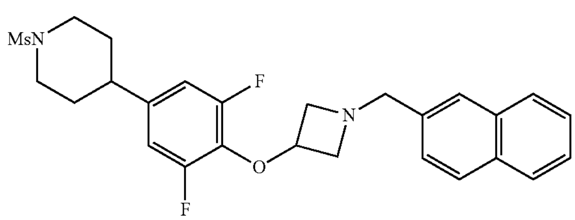 | $^1$H NMR (400 MHz, CDCl$_3$) δ = 7.82-7.79 (m, 3H), 7.73 (s, 1H), 7.48-7.41 (m, 3H), 6.76-6.70 (m, 2H), 4.80 (quint, J = 6.0 Hz, 1H), 3.95-3.90 (m, 2H), 3.85 (s, 2H), 3.77-3.73 (m, 2H), 3.31-3.27 (m, 2H), 2.81 (s, 3H), 2.74 (dt, J = 12.4, 2.8 Hz, 2H), 2.52 (tt, J = 12.4, 3.6 Hz, 1H), 1.95-1.89 (m, 2H), 1.73 (ddd, J = 25.6, 12.4, 4.0 Hz, 2H); $^{19}$F NMR (376.46 MHz, CDCl$_3$) δ = −127.56; MS calcd. for C$_{26}$H$_{29}$F$_2$N$_2$O$_3$S ([M + H]$^+$): 487.2, found: 487.2. |
| A31 | 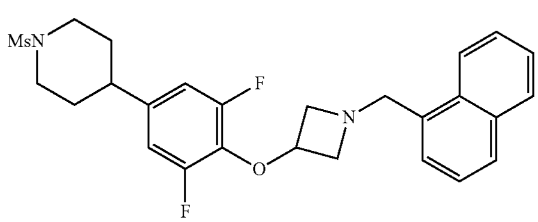 | $^1$H NMR (400 MHz, CDCl$_3$) δ = 8.14 (d, J = 8.4 Hz, 1H), 7.86-7.83 (m, 1H), 7.77 (dd, J = 7.2, 1.6 Hz, 1H), 7.55-7.39 (m, 4H), 6.76-6.69 (m, 2H), 4.80 (quint, J = 6.0 Hz, 1H), 4.13 (s, 2H), 3.95-3.90 (m, 2H), 3.79-3.75 (m, 2H), 3.34-3.30 (m, 2H), 2.81 (s, 3H), 2.74 (dt, J = 12.4, 2.4 Hz, 2H), 2.52 (tt, J = 12.4, 3.6 Hz, 1H), 1.95-1.89 (m, 2H), 1.73 (ddd, J = 25.6, 12.4, 4.0 Hz, 2H); $^{19}$F NMR (376.46 MHz, CDCl$_3$) δ = −127.58; MS calcd. for C$_{26}$H$_{29}$F$_2$N$_2$O$_3$S ([M + H]$^+$): 487.2, found: 487.2. |

TABLE 1-continued

| Example # | Structure | NMR and/or ESMS |
|---|---|---|
| A32 | 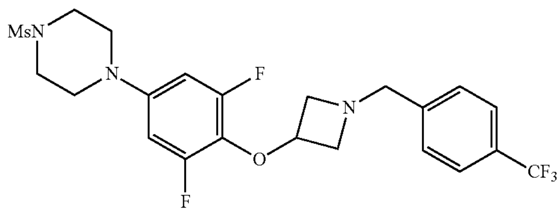 | $^1$H-NMR (400 MHz, CDCl$_3$) δ = 7.57 (d, J = 8.0 Hz, 2H), 7.40 (d, J = 8.0 Hz, 2H), 6.48-6.39 (m, 2H), 4.69 (quint, J = 6.0 Hz, 1H), 3.73 (s, 2H), 3.72-3.68 (m, 2H), 3.37-3.34 (m, 4H), 3.25-3.19 (m, 6H), 2.83 (s, 3H); $^{19}$F-NMR (376.46 MHz, CDCl$_3$) δ = −62.42, −126.66; MS calcd. for C$_{22}$H$_{25}$F$_5$N$_3$O$_3$S ([M + H]$^+$): 505.2, found: 505.1. |
| A33 | 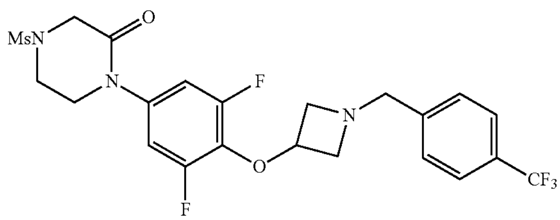 | $^1$H-NMR (400 MHz, CDCl$_3$) δ = 7.52 (d, J = 8.0 Hz, 2H), 7.35 (d, J = 8.0 Hz, 2H), 6.89-6.82 (m, 2H), 4.74 (quint, J = 6.0 Hz, 1H), 4.00 (s, 2H), 3.73-3.66 (m, 6H), 3.60-3.57 (m, 2H), 3.31-3.24 (m, 2H), 2.89 (s, 3H); $^{19}$F-NMR (376.46 MHz, CDCl$_3$) δ = −62.67, −126.29; MS calcd. for C$_{22}$H$_{23}$F$_5$N$_3$O$_4$S ([M + H]$^+$): 520.1, found: 520.1. |
| A34 | 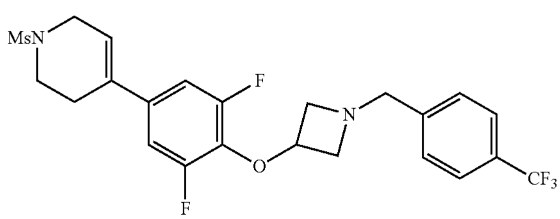 | $^1$H-NMR (400 MHz, CDCl$_3$) δ = 7.57 (d, J = 8.0 Hz, 2H), 7.41 (d, J = 8.0 Hz, 2H), 6.94-6.86 (m, 2H), 6.06-6.02 (m, 1H), 4.81 (quint, J = 6.0 Hz, 1H), 3.96-3.94 (m, 2H), 3.75-3.72 (m, 4H), 3.50 (t, J = 6.0 Hz, 2H), 3.28-3.25 (m, 2H), 2.96 (s, 3H), 2.58-2.53 (m, 2H); $^{19}$F-NMR (376.46 MHz, CDCl$_3$) δ = −62.43, −127.83; MS calcd. for C$_{23}$H$_{24}$F$_5$N$_3$O$_3$S ([M + H]$^+$): 503.1, found: 503.1. |
| A35 | 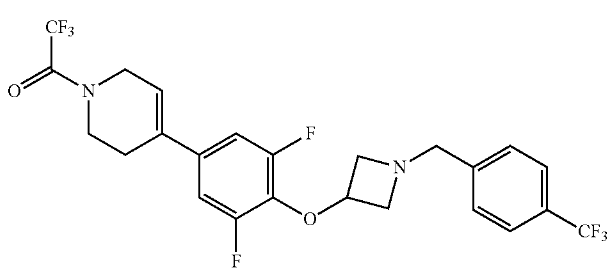 [SMILES: O=C(N1CC=C(c2cc(F)c(OC3CN(Cc4ccc(C(F)(F)F)cc4)C3)c(F)c2)CC1)C(F)(F)F] | $^1$H-NMR (400 MHz, CDCl$_3$) δ = 7.57 (d, J = 8.0 Hz, 2H), 7.41 (d, J = 8.0 Hz, 2H), 6.94-6.86 (m, 2H), 6.06-6.03 (m, 0.65H), 6.0-5.96 (m, 0.35H), 4.82 (quint, J = 6.0 Hz, 1H), 4.30-4.25 (m, 2H), 3.88 (t, J = 6.0 Hz, 0.7H), 3.81 (t, J = 6.0 Hz, 1.3H), 3.76-3.71 (m, 4H), 3.28-3.24 (m, 2H), 2.58-2.52 (m, 2H); $^{19}$F-NMR (376.46 MHz, CDCl$_3$) δ = −62.43, −69.31, −127.71; MS calcd. for C$_{24}$H$_{21}$F$_8$N$_2$O$_2$ ([M + H]$^+$): 521.1, found: 521.1. |

TABLE 1-continued

| Example # | Structure | NMR and/or ESMS |
|---|---|---|
| A36 | 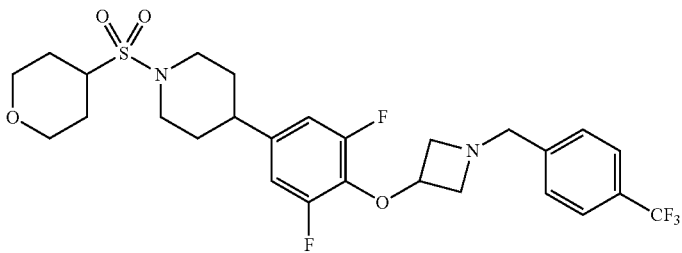 [SMILES: O=S(=O)(C1CCOCC1)N1CCC(c2cc(F)c(OC3CN(Cc4ccc(C(F)(F)F)cc4)C3)c(F)c2)CC1] | $^1$H-NMR (400 MHz, CDCl$_3$) δ = 7.57 (d, J = 8.0 Hz, 2H), 7.40 (d, J = 8.0 Hz, 2H), 6.77-6.70 (m, 2H), 4.77 (quint, J = 6.0 Hz, 1H), 4.11-4.07 (m, 2H), 3.97-3.91 (m, 2H), 3.74 (s, 2H), 3.74-3.70 (m, 2H), 3.38 (ddd, 23.4, 12.2, 2.0 Hz, 2H), 3.21-3.23 (m, 2H), 3.14 (tt, J = 12.0, 3.6 Hz, 1H), 2.97 (dt, J = 12.8, 2.2 Hz, 2H), 2.56 (tt, J = 12.2, 3.4 Hz, 1H), 1.99-1.83 (m, 6H), 1.67 (ddd, J = 25.4, 12.4, 4.0 Hz, 2H); $^{19}$F-NMR (376.46 MHz, CDCl$_3$) δ = −62.43, −127.68; MS calcd. for [M + H]$^+$ C$_{27}$H$_{32}$F$_5$N$_2$O$_4$S: 574.2, found: 574.2. |
| A37 | 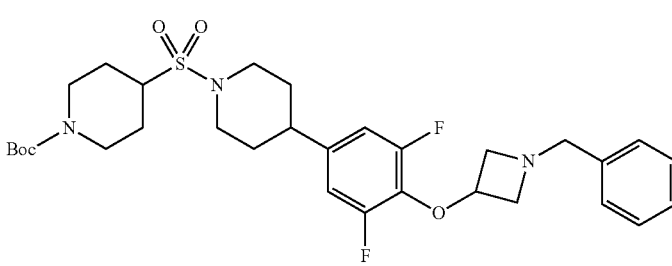 | $^1$H-NMR (400 MHz, CDCl$_3$) δ = 7.67 (d, J = 8.0 Hz, 2H), 7.40 (d, J = 8.0 Hz, 2H), 6.77-6.69 (m, 2H), 4.77 (quint, J = 5.9 Hz, 1H), 4.25 (br s, 2H), 3.96-3.90 (m, 2H), 3.74 (s, 2H), 3.74-3.70 (m, 2H), 3.27-3.23 (m, 2H), 3.04 (tt, J = 12.0, 3.6 Hz, 1H), 2.96 (dt, J = 12.9, 2.2 Hz, 2H), 2.76-2.66 (m, 2H), 2.56 (tt, J = 12.1, 3.4 Hz, 1H), 2.07-2.01 (m, 2H), 1.90-1.83 (m, 2H), 1.75-1.60 (m, 4H) 1.46 (s, 9H); $^{19}$F-NMR (376.46 MHz, CDCl$_3$) δ = −62.42, −127.68; MS calcd. for [M + H]$^+$ C$_{32}$H$_{40}$F$_5$N$_3$O$_5$S: 674.3, found: 674.3. |
| A38 | 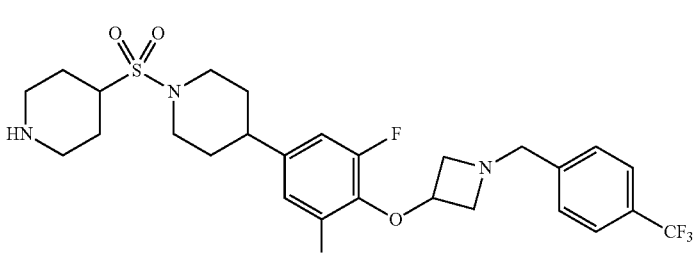 | $^1$H-NMR (400 MHz, CDCl$_3$) δ = 7.57 (d, J = 8.0 Hz, 2H), 7.41 (d, J = 8.1 Hz, 2H), 6.76 (m, 2H), 4.77 (quint, J = 5.7 Hz, 1H), 3.95-3.88 (m, 2H), 3.77-3.71 (m, 5H), 3.51-3.45 (m, 1H), 3.43-3.34 (m, 1H), 3.29-3.24 (m, 2H), 3.12-3.04 (m, 1H), 3.04-2.95 (m, 2H), 2.81-2.70 (m, 2H), 2.62-2.52 (m, 1H), 2.20-2.13 (m, 2H), 2.0 (m, 1H), 1.89-1.82 (m, 5H); $^{19}$F NMR (376.46 MHz, CDCl$_3$) δ = −62.44, −127.75; MS calcd. for [M + H]$^+$ C$_{27}$H$_{32}$F$_5$N$_3$O$_3$S: 574.2, found: 574.2. |

TABLE 1-continued

| Example # | Structure | NMR and/or ESMS |
|---|---|---|
| A39 | [Structure: Boc-pyrrolidine-3-sulfonyl-piperidine-4-(3,5-difluoro-4-(azetidin-3-yloxy)phenyl), azetidine N-CH2-(4-trifluoromethylphenyl)] | $^1$H-NMR (400 MHz, CDCl$_3$) δ = 7.57 (d, J = 8.0 Hz, 2H), 7.41 (d, J = 8.0 Hz, 2H), 6.77–6.69 (m, 2H), 4.77 (quint, J = 5.9 Hz, 1H), 3.99-3.91 (d, J = 12.1 Hz, 2H), 3.74 (s, 2H), 3.73-3.64 (m, 2H), 3.43-3.33 (m, 1H), 3.27-3.23 (m, 2H), 2.92 (dt, J = 12.5, 2.2 Hz, 2H), 2.60-2.50 (m, 1H), 2.43-2.21 (m, 2H), 1.92-1.84 (m, 2H), 1.75-1.63 (m, 2H), 1.62-1.56 (m, 4H), 1.46 (s, 9H) ; $^{19}$F NMR (376.46 MHz, CDCl$_3$) δ = −62.43, −127.62; MS calcd. For [M + H]$^+$ C$_{31}$H$_{38}$F$_5$N$_3$O$_5$S: 660.3, found: 660.3. |
| A40 | [Structure: pyrrolidine-3-sulfonyl-piperidine-4-(3,5-difluoro-4-(azetidin-3-yloxy)phenyl), azetidine N-CH2-(4-trifluoromethylphenyl)] | $^1$H-NMR (400 MHz, CDCl$_3$) δ = 7.59 (d, J = 8.0 Hz, 2H), 7.44 (d, J = 7.8 Hz, 2H), 6.78-6.71 (m, 2H), 4.79 (quint, J = 7.7 Hz, 1H), 3.98-3.90 (m, 2H), 3.85-3.78 (m, 4H), 3.77-3.73 (m, 1H), 3.73-3.68 (m, 1H), 3.51-3.45 (m, 2H), 3.36-3.29 (m, 2H), 3.05-2.90 (m, 2H), 2.62-2.53 (m, 1H), 2.36-2.20 (m, 3H), 1.93-1.83 (m, 5H); $^{19}$F NMR (376.46 MHz, CDCl$_3$) δ = −62.49, −127.59; MS calcd. For [M + H]$^+$ C$_{26}$H$_{30}$F$_5$N$_3$O$_3$S: 560.2, found: 560.2. |
| A41 | [Structure: HO-CH2CH2CH2-sulfonyl-piperidine-4-(3,5-difluoro-4-(azetidin-3-yloxy)phenyl), azetidine N-CH2-(4-trifluoromethylphenyl)] | $^1$H-NMR (400 MHz, CDCl$_3$) δ = 7.59 (d, J = 7.6 Hz, 2H), 7.46 (d, J = 7.4 Hz, 2H), 6.74 (d, J = 7.6 Hz, 2H), 4.84-4.77 (m, 1H), 3.96-3.84 (m, 6H), 3.82-3.76 (m, 3H), 3.40-3.32 (m, 2H), 3.08 (t, J = 7.2, 2H), 2.85 (t, J = 11.5, 2H), 2.58-2.48 (m, 1H), 2.10-2.04 (m, 2H), 1.93-1.84 (m, 2H), 1.76-1.64 (m, 2H); $^{19}$F NMR (376.46 MHz, CDCl$_3$) δ = −62.51, −127 −63; MS calcd. For [M + H]$^+$ C$_{25}$H$_{29}$F$_5$N$_2$O$_4$S: 549.2, found: 549.2. |
| A42 | [Structure: Ms-N-piperazine-pyrimidin-2-yl, pyrimidine-5-O-azetidin-3-yl, azetidine N-CH2-(4-trifluoromethylphenyl)] | $^1$H-NMR (400 MHz, CDCl$_3$) δ = 7.98 (s, 2H), 7.58 (d, J = 8.0 Hz, 2H), 7.40 (d, J = 8.0 Hz, 2H), 4.72 (quint, J = 6.0 Hz, 1H), 3.87-3.84 (m, 2H), 3.79-3.76 (m, 2H), 3.74 (s, 2H), 3.27 (t, J = 5.2 Hz, 4H), 3.20-3.16 (m, 4H), 2.79 (s, 3H); $^{19}$F-NMR (376.46 MHz, CDCl$_3$) δ = −62.45; MS calcd. For C$_{20}$H$_{25}$F$_5$N$_5$O$_3$S ([M + H]$^+$): 472.2, found: 472.1. |

TABLE 1-continued

| Example # | Structure | NMR and/or ESMS |
|---|---|---|
| A43 | 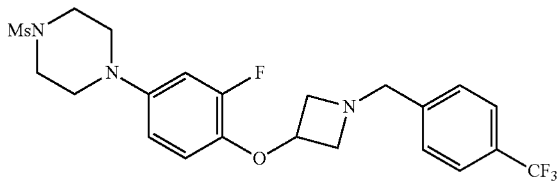 | $^1$H-NMR (400 MHz, CDCl$_3$) δ = 7.57 (d, J = 8.0 Hz, 2H), 7.40 (d, J = 8.0 Hz, 2H), 7.73-7.66 (m, 2H), 7.58-7.55 (m, 1H), 4.76 (quint, J = 6.0 Hz, 1H), 3.80 (t, J = 6.4 Hz, 2H), 3.75 (s, 2H), 3.38-3.35 (m, 4H), 3.22-3.15 (m, 6H), 2.82 (s, 3H); $^{19}$F-NMR (376.46 MHz, CDCl$_3$) δ = −62.43, −131.55; MS calcd. For C$_{22}$H$_{26}$F$_4$N$_3$O$_3$S ([M + H]$^+$): 488.2, found: 488.2. |
| A44 | 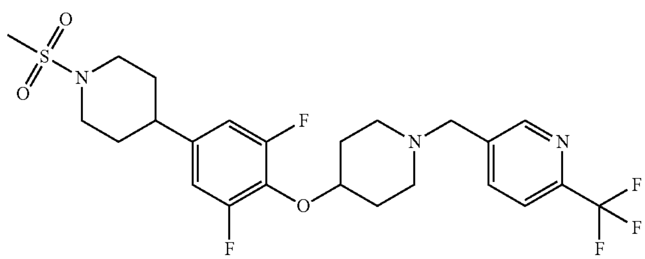 [SMILES: CS(=O)(=O)N1CCC(c2cc(F)c(OC3CCN(Cc4ccc(C(F)(F)F)nc4)CC3)c(F)c2)CC1] | $^1$H-NMR (400 MHz, CDCl$_3$) δ = 8.66 (s, 1H), 7.87 (d, J = 7.2 Hz, 1H), 7.66 (d, J = 8.0 Hz, 1H), 6.73 (m, 2H), 4.20 (m, 1H), 3.93 (m, 2H), 3.60 (s, 2H), 2.81 (s, 3H), 2.74 (m, 2H), 2.53 (m, 1H), 2.30 (m, 2H), 1.89 (m, 6H), 1.73 (m, 2H); MS calcd. for C$_{24}$H$_{29}$F$_5$N$_3$O$_3$S ([M + H]$^+$): 534.2, found: 534.2. |
| A45 | 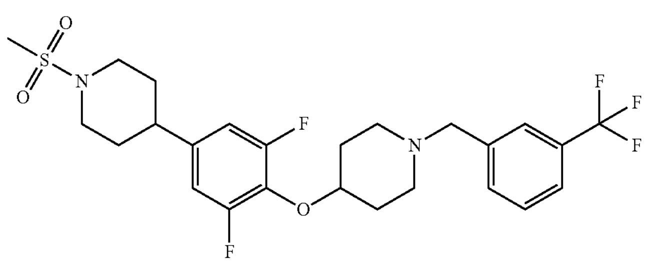 [SMILES: CS(=O)(=O)N1CCC(c2cc(F)c(OC3CCN(Cc4cccc(C(F)(F)F)c4)CC3)c(F)c2)CC1] | $^1$H-NMR (400 MHz, CDCl$_3$) δ = 7.59 (s, 1H), 7.51 (m, 2H), 7.42 (m, 1H), 6.74 (m, 2H), 4.19 (m, 1H), 3.93 (d, J = 11.6 Hz, 2H), 3.56 (s, 2H), 2.81 (s, 3H), 2.74 (m, 2H), 2.53 (m, 1H), 2.26 (m, 2H), 1.92 (m, 6H), 1.75 (m, 2H); MS calcd. for C$_{25}$H$_{30}$F$_5$N$_2$O$_3$S ([M + H]$^+$): 533.2, found: 533.2. |

Example B1

5-((4-(2,6-Difluoro-4-(1-(methylsulfonyl)piperidin-4-yl)phenoxy)piperidin-1-yl)methyl)-3-(trifluoromethyl)-1,2,4-oxadiazole

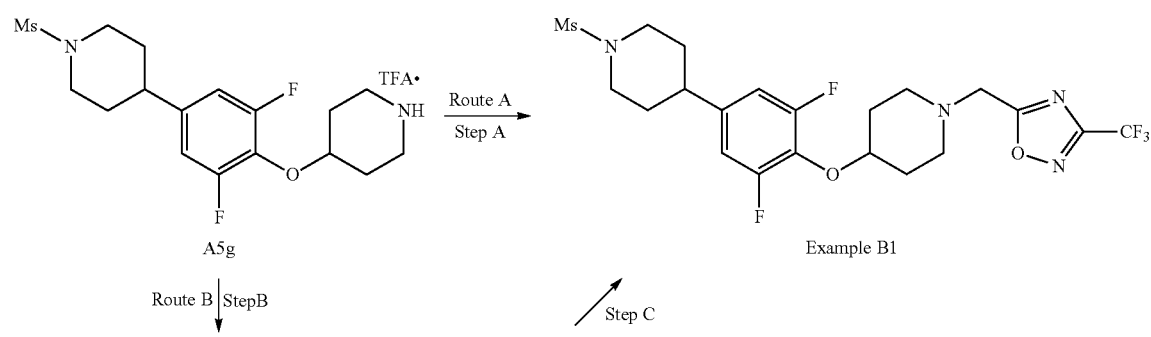

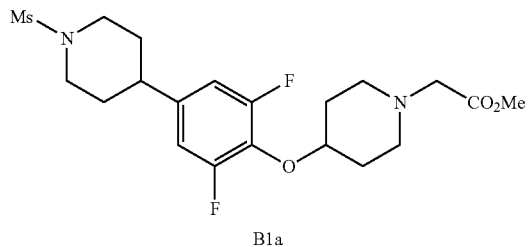

B1a

Route A. Step A: To a solution of A5g (977 mg, 2 mmol) in N-methylpyrrolidone (7 mL) is added 5-(chloromethyl)-3-(trifluoromethyl)-1,2,4-oxadiazole (410 mg, 2.2 mmol, obtained following literature procedure: Go, Atsushi; Usui, Yoshihiro; Ikeda, Kaoru; Endo, Keiji (1985), JP 60149573 A) in N-methylpyrrolidone (3 mL) and diisopropylethylamine (1.04 mL, 6 mmol). The reaction mixture is heated to 60° C. for 3 hours, cooled down and diluted with water. The mixture is extracted with ethyl acetate (3×), washed with brine, dried over sodium sulfate and concentrated in vacuo. Purification of the crude material by flash chromatography (hexanes/ethyl acetate gradient) affords the title compound (Example B1) as a white solid: $^1$H-NMR (400 MHz, DMSO-$d_6$) δ=7.09 (m, 2H), 4.11 (m, 1H), 4.07 (s, 2H), 3.65 (m, 2H), 2.89 (s, 3H), 2.78 (m, 4H), 2.62 (m, 1H), 2.41 (m, 2H), 1.86 (m, 4H), 1.65 (m, 4H); MS calcd. For $C_{21}H_{26}F_5N_4O_4S$ ([M+H]$^+$): 525.2, found: 525.1.

Route B. Step B: A solution of A5g (567 mg, 1 mmol) in N-methylpyrrolidone (3 mL) is treated with triethylamine (696 μL, 5 mmol) and stirred for 10 minutes. Methyl 2-bromoacetate (85 μL, 0.9 mmol) is added and the mixture is stirred at room temperature for 30 minutes. Water is added and the product is extracted with ethyl acetate (3×), dried over sodium sulfate and concentrated in vacuo. Purification of the crude material by flash chromatography (hexanes/ethyl acetate gradient) affords methyl 2-(4-(2,6-difluoro-4-(1-(methylsulfonyl)piperidin-4-yl)phenoxy)piperidin-1-yl)acetate B1a as a white solid: $^1$H-NMR (400 MHz, DMSO-$d_6$) δ=7.09 (m, 2H), 4.06 (m, 1H), 3.65 (m, 2H), 3.60 (s, 3H), 3.23 (s, 2H), 2.89 (s, 3H), 2.75 (m, 4H), 2.62 (m, 1H), 2.34 (m, 2H), 1.85 (m, 4H), 1.59-1.69 (m, 4H); MS calcd. For $C_{20}H_{29}F_2N_2O_5S$ ([M+H]$^+$): 447.2, found: 447.2.

Step C: To a solution of trifluoro-N'-hydroxyacetimidamide (26 mg. 0.2 mmol, obtained using procedure described by Brown, Henry C.; Wetzel, Charles R. J. Org. Chem. (1965), 30(11), 3734-8) in anhydrous dioxane (2 mL) is added sodium hydride (60% in mineral oil, 8 mg, 0.2 mmol) and stirred at 60° C. for 1 hour. The resulting slurry is treated with a solution of Intermediate B1a (45 mg, 0.1 mmol) in dioxane (0.7 mL) and activated molecular sieves (4 A, 100 mg) and the mixture is stirred at 100° C. overnight. An aqueous solution of sodium bicarbonate is added. The mixture is extracted with dichlomethane (3×), dried over sodium sulfate and concentrated in vacuo. The crude material is purified by flash chromatography (hexanes/ethyl acetate gradient) to afford the title compound (Example B1) as a white solid. $^1$H-NMR (400 MHz, DMSO-$d_6$) δ=7.09 (m, 2H), 4.11 (m, 1H), 4.07 (s, 2H), 3.65 (m, 2H), 2.89 (s, 3H), 2.78 (m, 4H), 2.62 (m, 1H), 2.41 (m, 2H), 1.86 (m, 4H), 1.65 (m, 4H); MS calcd. For $C_{21}H_{26}F_5N_4O_4S$ ([M+H]$^+$): 525.2, found: 525.1.

Example B2

5-((4-(2,6-difluoro-4-(1-(methylsulfonyl)piperidin-4-yl)phenoxy)piperidin-1-yl)methyl)-3-(2-fluoropropan-2-yl)-1,2,4-oxadiazole

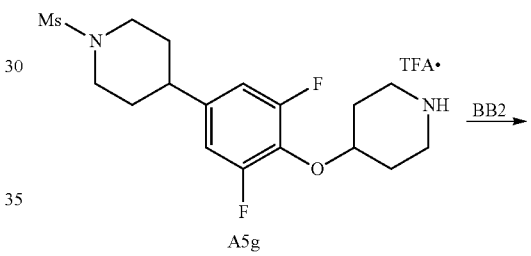

A5g

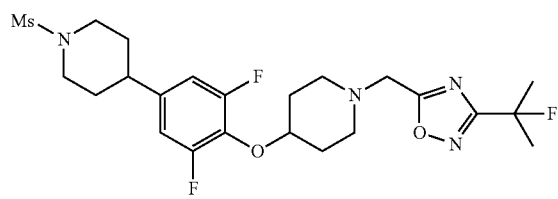

Example B2

To a solution of A5g (98 mg, 0.2 mmol) in N-methylpyrrolidone (1 mL) is added BB2 (398 mg, 2.2 mmol) in N-methylpyrrolidone (1 mL) and diisopropylethylamine (0.104 mL, 0.6 mmol). The reaction mixture is heated to 40° C. for 2 hours and to 60° C. for 1 hour. The mixture is cooled to room temperature, diluted with water and extracted with ethyl acetate (3×). The combined organic phase is washed with brine, dried over sodium sulfate and concentrated in vacuo. Purification of the crude material by flash chromatography (hexanes/ethyl acetate gradient) affords the title compound (Example B2) as a white solid: $^1$H NMR (400 MHz, CDCl$_3$) δ=6.74 (m, 2H), 4.21 (m, 1H), 3.93 (m, 2H), 3.90 (s, 2H), 2.87 (m, 2H), 2.82 (s, 3H), 2.74 (m, 2H), 2.46-2.57 (m, 3H), 1.88-2.02 (m, 6H), 1.81 (d, J=21.6 Hz, 6H), 1.75 (m, 2H);

$^{19}$F-NMR (376.46 MHz, CDCl$_3$) δ=−126.44, −140.17; MS calcd. For C$_{23}$H$_{32}$F$_3$N$_4$O$_4$S ([M+H]$^+$): 517.2, found: 517.2.

Example B3

5-((4-(2,6-difluoro-4-(1-(methylsulfonyl)piperidin-4-yl)phenoxy)piperidin-1-yl)methyl)-3-(1,1-difluoroethyl)-1,2,4-oxadiazole

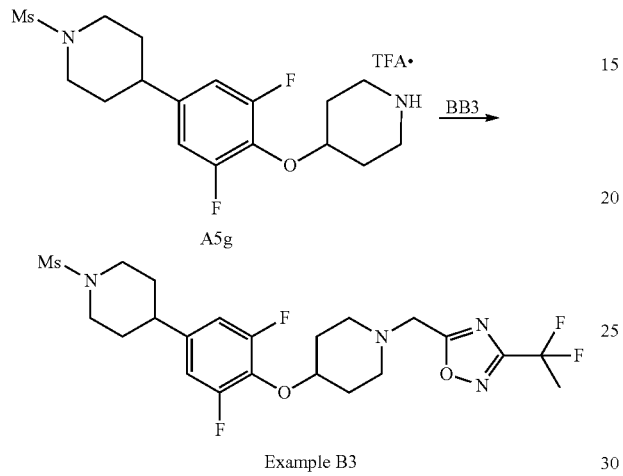

Example B3

To a solution of A5g (968 mg, 2 mmol) in N-methylpyrrolidone (7 mL) is added BB3 (398 mg, 2.2 mmol) in N-methylpyrrolidone (3 mL) and diisopropylethylamine (1.02 mL, 6 mmol). The reaction mixture is heated to 60° C. for 1 hour. Additional BB3 (72 mg, 0.39 mmol) in N-methylpyrrolidone (0.2 mL) is added and the mixture is stirred at 60° C. for 30 minutes. The mixture is cooled to room temperature, diluted with water and extracted with ethyl acetate (3×). The combined organic phase is washed with brine, dried over sodium sulfate and concentrated in vacuo. Purification of the crude material by flash chromatography (hexanes/ethyl acetate gradient) affords the title compound (Example B3) as a white solid: $^1$H NMR (400 MHz, CDCl$_3$) δ=6.74 (m, 2H), 4.21 (m, 1H), 3.94 (m, 4H), 2.88 (m, 2H), 2.82 (s, 3H), 2.74 (m, 2H), 2.48-2.57 (m, 3H), 2.08 (t, J=18.6 Hz, 3H), 1.88-2.02 (m, 6H), 1.75 (m, 2H); $^{19}$F-NMR (376.46 MHz, CDCl$_3$) δ=−91.45, −126.47; MS calcd. For C$_{22}$H$_{29}$F$_4$N$_4$O$_4$S ([M+H]$^+$): 521.2, found: 521.2.

Example B4

5-((4-(5-(4-(Methylsulfonyl)piperazin-1-yl)pyrazin-2-yloxy)piperidin-1-yl)methyl)-3-(trifluoromethyl)-1,2,4-oxadiazole

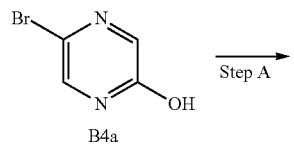

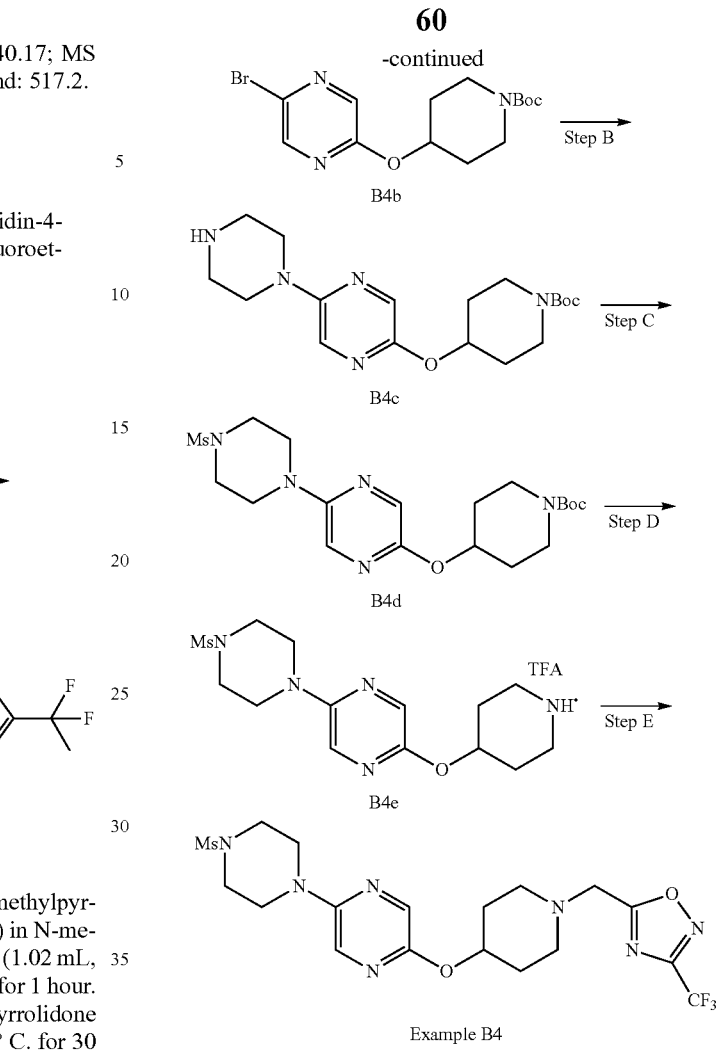

Example B4

Step A: A mixture of 5-bromopyrazin-2-ol B4a (525 mg, 3 mmol), tert-butyl 4-(methylsulfonyloxy)piperidine-1-carboxylate (1.117 g, 4 mmol), 18-crown-6 (79 mg, 0.3 mmol), K$_2$CO$_3$ (829 mg, 6 mmol) in butan-2-one (19 mL) is subjected to microwave irradiation at 130° C. for 15 min. The solids are filtered off, washed with ethyl acetate and purified by flash chromatography (hexanes/ethyl acetate gradient) to afford tert-butyl 4-(5-bromopyrazin-2-yloxy)piperidine-1-carboxylate B4b as a white solid: MS calcd. For C$_{14}$H$_{21}$BrN$_3$O$_3$ ([M+H]$^+$): 358.1, found: 358.1.

Step B: A mixture of Intermediate B4b (179 mg, 0.5 mmol), piperazine (112 mg, 1.3 mmol), Pd (Oac)$_2$ (2.2 mg, 0.01 mmol), BINAP (10 mg, 0.015 mmol) in toluene (2 mL) is purged with argon and heated at 80° C. for 2 h. Water is added and the mixture is extracted with ethyl acetate (3×), dried (Na$_2$SO$_4$) and concentrated to give tert-butyl 4-(5-(piperazin-1-yl)pyrazin-2-yloxy)piperidine-1-carboxylate B4c: MS calcd. For C$_{18}$H$_{30}$N$_5$O$_3$ ([M+H]$^+$): 364.2, found: 364.2. The product is used without purification.

Step C: The mesylation of Intermediate B4c is achieved using the procedure described in Example A4, Step E to afford tert-butyl 4-(5-(4-(methylsulfonyl)piperazin-1-yl)pyrazin-2-yloxy)piperidine-1-carboxylate B4d: $^1$H-NMR (400 MHz, DMSO-d$_6$) δ=7.85 (d, J=1.4 Hz, 1H), 7.63 (d, J=1.4 Hz, 1H), 5.03 (m, 1H), 3.76 (m, 2H), 3.53 (m, 4H), 3.37 (m, 4H), 3.27 (m, 2H), 2.82 (s, 3H), 1.94 (m, 2H), 1.70 (m, 2H), 1.47 (s, 9H); MS calcd. For C$_{19}$H$_{31}$N$_5$O$_5$S ([M+H]$^+$): 442.2, found: 442.2.

Step D: Deprotection of Intermediate B4d is performed as demonstrated in Example A5, Step F to give 2-(4-(methylsulfonyl)piperazin-1-yl)-5-(piperidin-4-yloxy)pyrazine trifluoroacetate salt B4e: MS calcd. For $C_{14}H_{24}N_5O_3S$ ([M+H]$^+$): 342.2, found: 342.1.

Step E: The title compound (Example D1) is obtained using procedure depicted in Example B1, Step A: $^1$H-NMR (400 MHz, DMSO-d$_6$) δ=7.85 (d, J=1.4 Hz, 1H), 7.62 (d, J=1.4 Hz, 1H), 4.92 (m, 1H), 3.99 (s, 2H), 3.53 (m, 4H), 3.36 (m, 4H), 2.87 (m, 2H), 2.82 (s, 3H), 2.57 (m, 2H), 2.06 (m, 2H), 1.87 (m, 2H); $^{19}$F-NMR (376.46 MHz, CDCl$_3$) δ=−65.94; MS calcd. For $C_{18}H_{25}F_3N_7O_4S$ ([M+H]$^+$): 492.2, found: 492.1.

By repeating the procedure described in the above Examples B1-B4, using appropriate starting materials, the following compounds of Formula I, as identified in Table 2, are obtained:

TABLE 2

| Example # | Structure | NMR and/or ESMS |
|---|---|---|
| B5 | [structure] | $^1$H NMR (400 MHz, CDCl$_3$) δ = 6.79 (t, J = 52.5 Hz, 1H), 6.74 (m, 2H), 4.22 (m, 1H), 3.94 (m, 4H), 2.88 (m, 2H), 2.81 (s, 3H), 2.74 (m, 2H), 2.49-2.58 (m, 3H), 1.88-2.02 (m, 6H), 1.74 (m, 2H); $^{19}$F-NMR (376.46 MHz, CDCl$_3$) δ = −120.12, −126.48; MS calcd. For $C_{21}H_{27}F_4N_4O_4S$ ([M + H]+): 507.2, found: 507.2. |
| B6 | [structure] | $^1$H NMR (400 MHz, CDCl$_3$) δ = 6.93 (m, 2H), 6.86 (m, 1H), 4.31 (m, 1H), 3.98 (s, 2H), 3.93 (m, 2H), 2.87 (m, 2H), 2.82 (s, 3H), 2.75 (m, 2H), 2.50-2.58 (m, 3H), 1.88-2.05 (m, 6H), 1.77 (m, 2H); $^{19}$F-NMR (376.46 MHz, CDCl$_3$) δ = −65.95, −131.91; MS calcd. For $C_{21}H_{27}F_4N_4O_4S$ ([M + H]+): 507.2, found: 507.2. |
| B7 | [structure] | $^1$H NMR (400 MHz, CDCl$_3$) δ = 7.07 (t, J = 8.6 Hz, 1H), 6.65 (dd, J = 8.6, 2.5 Hz, 1H), 6.59 (dd, J = 12.6, 2.5 Hz, 1H), 4.31 (m, 1H), 3.98 (s, 2H), 3.93 (m, 2H), 2.74-2.91 (m, 8H), 2.57 (m, 2H), 2.02 (m, 2H), 1.76-1.94 (m, 6H); $^{19}$F-NMR (376.46 MHz, CDCl$_3$) δ = −65.94, −117.24; MS calcd. For $C_{21}H_{27}F_4N_4O_4S$ ([M + H]+): 507.2, found: 507.2. |
| B8 | [structure] | $^1$H NMR (400 MHz, DMSO-d$_6$) δ = 7.11 (m, 2H), 4.72 (quint, J = 5.6 Hz, 1H), 3.73 (s, 2H), 3.66 (m, 4H), 3.28 (m, 2H), 2.89 (s, 3H), 2.76 (m, 2H), 2.62 (m, 1H), 1.84 (m, 2H), 1.64 (m, 2H), 1.37 (s, 9H); MS calcd. For $C_{22}H_{31}F_2N_4O_4S$ ([M + H]$^+$): 485.2, found: 485.1. |
| B9 | [structure] | $^1$H NMR (400 MHz, DMSO-d$_6$) δ = 7.11 (m, 2H), 4.74 (quint, J = 5.6 Hz, 1H), 3.95 (s, 2H), 3.71 (m, 2H), 3.65 (m, 2H), 3.34 (m, 2H), 3.05 (sept, J = 6.9 Hz, 1H), 2.89 (s, 3H), 2.76 (m, 2H), 2.62 (m, 1H), 1.84 (m, 2H), 1.64 (m, 2H), 1.25 (d, J = 6.9 Hz, 6H); MS calcd. For $C_{21}H_{29}F_2N_4O_4S$ ([M + H]$^+$): 471.2, found: 471.1. |

TABLE 2-continued

| Example # | Structure | NMR and/or ESMS |
|---|---|---|
| B10 | (structure) | $^1$H NMR (400 MHz, DMSO-$d_6$) δ = 7.11 (m, 2H), 4.73 (quint, J = 5.6 Hz, 1H), 3.90 (s, 2H), 3.67 (m, 4H), 3.31 (m, 2H), 2.89 (s, 3H), 2.76 (m, 2H), 2.62 (m, 1H), 2.11 (m, 1H), 1.84 (m, 2H), 1.64 (m, 2H), 1.05 (m, 2H), 0.88 (m, 2H); MS calcd. For $C_{21}H_{27}F_2N_4O_4S$ ([M + H]$^+$): 469.2, found: 469.1. |
| B11 | (structure) | $^1$H NMR (400 MHz, DMSO-$d_6$) δ = 7.11 (m, 2H), 4.74 (quint, J = 5.6 Hz, 1H), 3.72 (s, 2H), 3.65 (m, 4H), 3.22-3.29 (m, 3H), 2.89 (s, 3H), 2.76 (m, 2H), 2.62 (m, 1H), 1.84 (m, 2H), 1.64 (m, 2H), 1.30 (d, J = 7.0 Hz, 6H); MS calcd. for $C_{21}H_{29}F_2N_4O_4S$ ([M + H]$^+$): 471.2, found: 471.2. |
| B12 | (structure) | $^1$H NMR (400 MHz, CDCl$_3$) δ = 6.75 (m, 2H), 4.80 (quint, J = 5.6 Hz, 1H), 4.05 (s, 2H), 3.93 (m, 4H), 3.48 (m, 2H), 2.81 (s, 3H), 2.74 (dt, J = 2.4, 12 Hz, 2H), 2.53 (m, 1H), 1.93 (m, 2H), 1.77 (m, 2H); MS calcd. for $C_{19}H_{22}F_5N_4O_4S$ ([M + H]$^+$): 497.1, found: 497.1. |
| B13 | (structure) | $^1$H NMR (400 MHz, CDCl$_3$) δ = 6.74 (m, 2H), 4.79 (quint, J = 5.6 Hz, 1H), 4.00 (s, 2H), 3.94 (m, 4H), 3.47 (m, 2H), 2.81 (s, 3H), 2.74 (dt, J = 2.4, 12 Hz, 2H), 2.53 (m, 1H), 2.07 (t, J = 18.8 Hz, 3H), 1.93 (m, 2H), 1.75 (m, 2H); MS calcd. for $C_{20}H_{25}F_4N_4O_4S$ ([M + H]$^+$): 493.2, found: 493.1. |
| B14 | (structure) | $^1$H NMR (400 MHz, CDCl$_3$) δ = 6.74 (m, 2H), 6.38 (s, 1H), 4.19 (m, 1H), 3.95 (s, 3H), 3.93 (m, 2H), 3.51 (s, 2H), 2.81 (s, 3H), 2.74 (m, 4H), 2.54 (m, 1H), 2.27 (m, 2H), 1.90 (m, 6H), 1.73 (m, 2H); MS calcd. for $C_{23}H_{30}F_5N_4O_3S$ ([M + H]$^+$): 536.2, found: 536.2. |
| B15 | (structure) | $^1$H NMR (400 MHz, CDCl$_3$) δ = 6.74 (m, 2H), 6.38 (s, 1H), 4.74 (m, 1H), 3.92 (m, 2H), 3.90 (s, 3H), 3.69 (m, 4H), 3.25 (m, 2H), 2.81 (s, 3H), 2.74 (dt, J = 2.4, 12 Hz, 2H), 2.53 (m, 1H), 1.92 (m, 2H), 1.80 (m, 3H); MS calcd. for $C_{21}H_{26}F_5N_4O_3S$ ([M + H]$^+$): 509.2, found: 509.2. |

TABLE 2-continued

| Example # | Structure | NMR and/or ESMS |
|---|---|---|
| B16 | 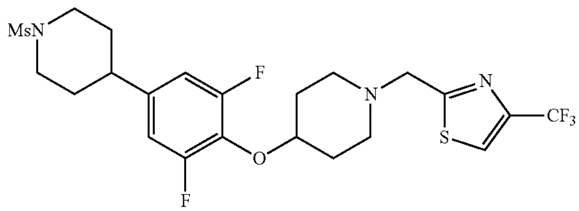 | $^1$H NMR (400 MHz, CDCl$_3$) δ = 7.71 (s, 1H), 6.74 (m, 2H), 4.21 (m, 1H), 3.93 (m, 2H), 3.86 (s, 2H), 2.90 (m, 2H), 2.81 (s, 3H), 2.74 (dt, J = 2.4, 12 Hz, 2H), 2.50 (m, 3H), 1.94 (m, 6H), 1.76 (m, 2H); MS calcd. for C$_{22}$H$_{27}$F$_5$N$_3$O$_3$S$_2$ ([M + H]$^+$): 540.1, found: 540.1. |
| B17 | 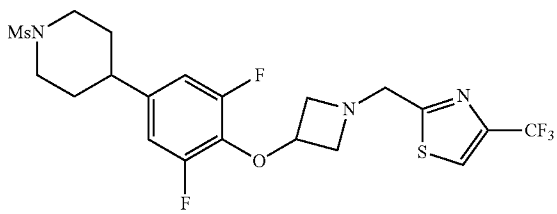 | $^1$H NMR (400 MHz, CDCl$_3$) δ = 7.70 (s, 1H), 6.74 (m, 2H), 4.82 (m, 1H), 4.03 (s, 3H), 3.93 (m, 2H), 3.87 (m, 2H), 3.43 (m, 2H), 2.81 (s, 3H), 2.74 (dt, J = 2.4, 12 Hz, 2H), 2.54 (m, 1H), 1.91 (m, 2H), 1.73 (m, 2H); MS calcd. for C$_{20}$H$_{23}$F$_5$N$_3$O$_3$S$_2$ ([M + H]$^+$): 512.2, found: 512.2. |
| B18 | 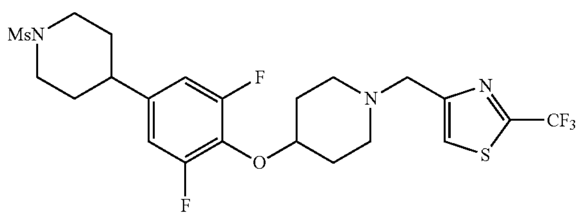 | $^1$H NMR (400 MHz, CDCl$_3$) δ = 7.46 (s, 1H), 6.73 (m, 2H), 4.19 (m, 1H), 3.93 (m, 2H), 3.77 (s, 2H), 2.83 (m, 2H), 2.82 (s, 3H), 2.74 (dt, J = 2.4, 12 Hz, 2H), 2.53 (m, 1H), 2.37 (m, 2H), 1.94 (m, 6H), 1.76 (m, 2H); MS calcd. for C$_{22}$H$_{27}$F$_5$N$_3$O$_3$S$_2$ ([M + H]$^+$): 540.1, found: 540.1. |
| B19 | 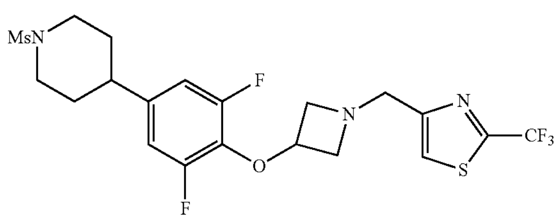 | $^1$H NMR (400 MHz, CDCl$_3$) δ = 7.39 (s, 1H), 6.74 (m, 2H), 4.79 (m, 1H), 3.92 (m, 4H), 3.81 (m, 2H), 3.36 (m, 2H), 2.81 (s, 3H), 2.74 (dt, J = 2.4, 12 Hz, 2H), 2.53 (m, 1H), 1.92 (m, 2H), 1.73 (m, 2H); MS calcd. for C$_{20}$H$_{23}$F$_5$N$_3$O$_3$S$_2$ ([M + H]$^+$): 512.2, found: 512.2. |
| B20 | 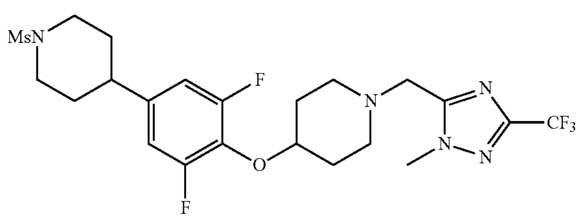 | $^1$H NMR (400 MHz, CDCl$_3$) δ = 6.74 (m, 2H), 4.18 (m, 1H), 4.02 (s, 3H), 3.92 (m, 2H), 3.72 (s, 2H), 2.81 (s, 3H), 2.72 (m, 4H), 2.53 (m, 1H), 2.33 (m, 2H), 1.92 (m, 6H), 1.74 (m, 2H); MS calcd. for C$_{22}$H$_{29}$F$_5$N$_5$O$_3$S ([M + H]$^+$): 538.2, found: 538.2. |
| B21 | 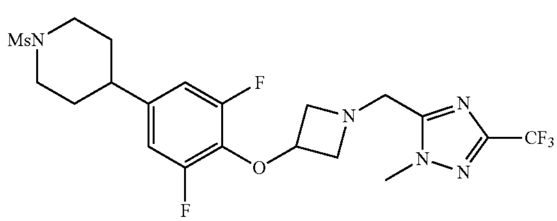 | $^1$H NMR (400 MHz, CDCl$_3$) δ = 6.74 (m, 2H), 6.38 (s, 1H), 4.76 (m, 1H), 3.98 (s, 3H), 3.91 (m, 2H), 3.86 (s, 2H), 3.72 (m, 2H), 3.38 (m, 2H), 2.80 (s, 3H), 2.73 (dt, J = 2.4, 12 Hz, 2H), 2.53 (m, 1H), 1.91 (m, 2H), 1.70 (m, 3H); MS calcd. for C$_{20}$H$_{25}$F$_5$N$_5$O$_3$S ([M + H]$^+$): 510.1, found: 510.1. |

TABLE 2-continued

| Example # | Structure | NMR and/or ESMS |
|---|---|---|
| B22 | 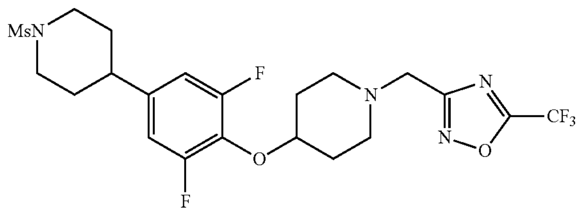 | $^1$H NMR (400 MHz, CDCl$_3$) δ = 6.73 (m, 2H), 4.22 (m, 1H), 3.92 (m, 2H), 3.83 (s, 2H), 2.84 (m, 2H), 2.81 (s, 3H), 2.72 (m, 2H), 2.50 (m, 3H), 1.93 (m, 6H), 1.76 (m, 2H); MS calcd. for C$_{21}$H$_{26}$F$_5$N$_4$O$_4$S ([M + H]$^+$): 525.2, found: 525.2. |
| B23 | 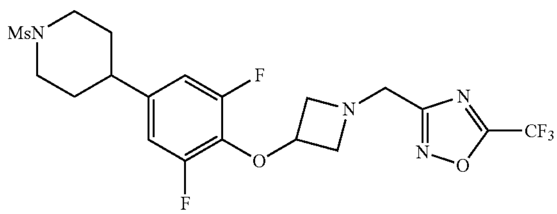 | $^1$H NMR (400 MHz, CDCl$_3$) δ = 6.74 (m, 2H), 4.78 (quint, J = 5.6 Hz, 1H), 3.91 (s, 5H), 3.44 (m, 2H), 2.81 (s, 3H), 2.74 (dt, J = 2.4, 12 Hz, 2H), 2.53 (m, 1H), 1.92 (m, 2H), 1.74 (m, 3H); MS calcd. for C$_{19}$H$_{22}$F$_5$N$_4$O$_4$S ([M + H]$^+$): 497.1, found: 497.1. |
| B24 | 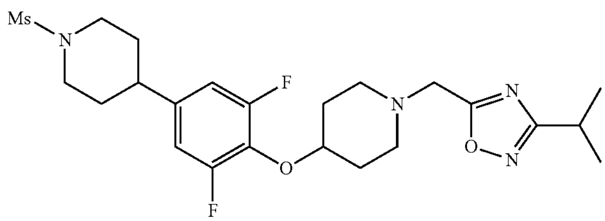 [SMILES: CC(C)c1noc(CN2CCC(Oc3c(F)cc(C4CCN(S(C)(=O)=O)CC4)cc3F)CC2)n1] | $^1$H NMR (400 MHz, CDCl$_3$) δ = 6.73 (m, 2H), 4.20 (m, 1H), 3.93 (m, 2H), 3.84 (s, 2H), 3.11 (sept, J = 7.0 Hz, 1H), 2.86 (m, 2H), 2.82 (s, 3H), 2.74 (m, 2H), 2.44-2.57 (m, 3H), 1.87-2.02 (m, 6H), 1.75 (m, 2H), 1.35 (d, J = 7.0 Hz, 6H); MS calcd. for C$_{23}$H$_{33}$F$_2$N$_4$O$_4$S ([M + H]$^+$): 499.2, found: 499.1. |
| B25 | 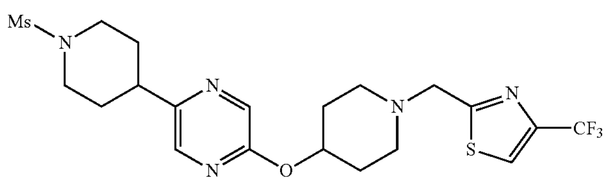 [SMILES: CS(=O)(=O)N1CCC(c2cnc(OC3CCN(Cc4nc(C(F)(F)F)cs4)CC3)cn2)CC1] | $^1$H NMR (400 MHz, CDCl$_3$) δ = 7.86 (d, J = 1.4 Hz, 1H), 7.72 (m, 1H), 7.63 (d, J = 1.4 Hz, 1H), 4.95 (m, 1H), 3.88 (s, 2H), 3.53 (m, 4H), 3.37 (m, 4H), 2.89 (m, 2H), 2.82 (s, 3H), 2.53 (m, 2H), 2.05 (m, 2H), 1.85 (m, 2H); $^{19}$F-NMR (376.46 MHz, CDCl$_3$) δ = −64.00; MS calcd. for C$_{19}$H$_{26}$F$_3$N$_6$O$_3$S$_2$ ([M + H]$^+$): 507.1, found: 507.1. |
| B26 | 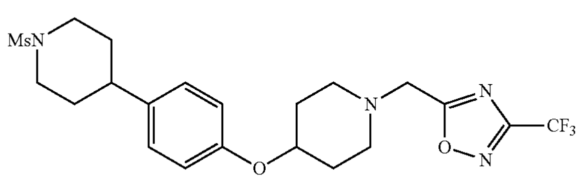 | $^1$H NMR (400 MHz, CDCl$_3$) δ = 7.10 (dd, J = 2.0, 6.8 Hz, 2H), 6.84 (dd, J = 2.0, 6.8 Hz, 2H), 4.33 (m, 1H), 3.98 (s, 2H), 3.92 (m, 2H), 2.83 (m, 2H), 2.81 (s, 3H), 2.75 (m, 2H), 2.56 (m, 3H), 2.00 (m, 2H), 1.93 (m, 4H), 1.79 (m, 2H); MS calcd. for C$_{21}$H$_{28}$F$_3$N$_4$O$_4$S ([M + H]$^+$): 489.2, found: 489.2. |
| B27 | 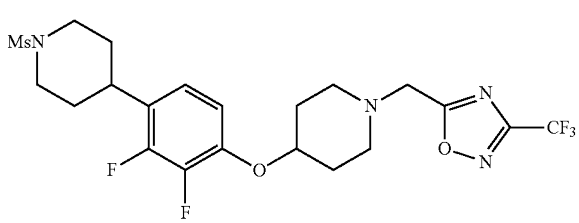 | $^1$H NMR (400 MHz, CDCl$_3$) δ = 6.81 (m, 1H), 6.73 (m, 1H), 4.35 (m, 1H), 3.98 (s, 2H), 3.94 (m, 2H), 2.84 (m, 3H), 2.82 (s, 3H), 2.79 (m, 2H), 2.57 (m, 2H), 2.00 (m, 2H), 1.95 (m, 4H), 1.80 (m, 2H); MS calcd. for C$_{21}$H$_{26}$F$_5$N$_4$O$_4$S ([M + H]$^+$): 525.2, found: 525.2. |

TABLE 2-continued

| Example # | Structure | NMR and/or ESMS |
|---|---|---|
| B28 | 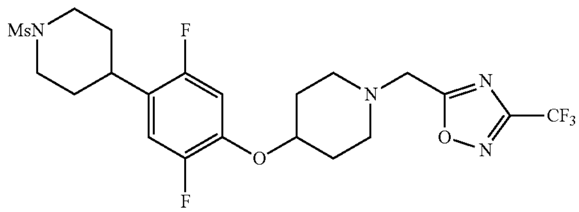 | $^1$H NMR (400 MHz, CDCl$_3$) δ = 6.90 (m, 1H), 6.68 (m, 1H), 4.30 (m, 1H), 3.98 (s, 2H), 3.93 (m, 2H), 2.84 (m, 3H), 2.81 (s, 3H), 2.79 (m, 2H), 2.58 (m, 2H), 1.99 (m, 2H), 1.95 (m, 4H), 1.80 (m, 2H); MS calcd. for C$_{21}$H$_{26}$F$_5$N$_4$O$_4$S ([M + H]$^+$): 525.2, found: 525.2. |
| B29 | 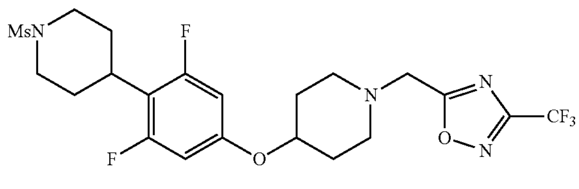 | $^1$H NMR (400 MHz, CDCl$_3$) δ = 6.40 (m, 2H), 4.28 (m, 1H), 3.98 (s, 2H), 3.91 (m, 2H), 2.96 (m, 1H), 2.81 (m, 5H), 2.73 (m, 2H), 2.58 (m, 2H), 2.18 (m, 2H), 2.00 (m, 2H), 1.89 (m, 2H), 1.76 (m, 2H); MS calcd. for C$_{21}$H$_{26}$F$_5$N$_4$O$_4$S ([M + H]$^+$): 525.2, found: 525.2. |
| B30 | 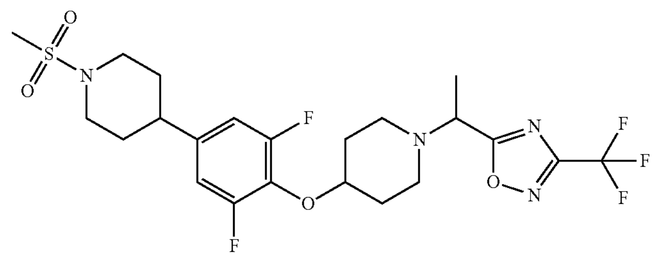 [SMILES: CC(c1nc(C(F)(F)F)no1)N1CCC(Oc2c(F)cc(C3CCN(S(C)(=O)=O)CC3)cc2F)CC1] | $^1$H NMR (400 MHz, CDCl$_3$) δ = 6.72 (m, 2H), 4.18 (m, 1H), 3.94 (m, 2H), 3.66 (m, 1H), 2.81 (s, 3H), 2.72 (m, 2H), 2.52 (m, 2H), 2.24 (m, 1H), 2.00 (m, 2H), 1.93 (m, 4H), 1.73 (m, 2H), 1.59 (d, J = 7.2 Hz, 3H); MS calcd. for C$_{22}$H$_{28}$F$_5$N$_4$O$_4$S ([M + H]$^+$): 539.2, found: 539.2. |

Example C1

4-(3,5-Difluoro-4-(1-(4-(trifluoromethyl)benzyl) pyrrolidin-3-yloxy)phenyl)-1-(methylsulfonyl)piperidine

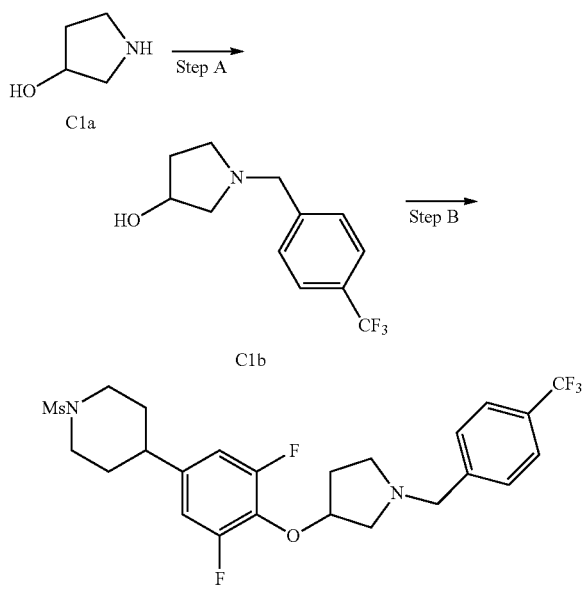

Step A: A solution of (R,S)-pyrrolidin-3-ol C1a (87 mg, 1 mmol) and 4-(trifluoromethyl)benzaldehyde (134 µL) in dichloromethane (10 mL) is treated with sodium triacetoxyborohydride (424 mg, 2 mmol). The mixture is then stirred at room temperature for 16 hours, treated with aqueous solution of sodium bicarbonate and stirred for 15 minutes. The mixture is extracted with dichloromethane (3×), dried over sodium sulfate and concentrated in vacuo. The crude material is purified by flash chromatography (hexanes/ethyl acetate gradient) to afford 1-(4-(trifluoromethyl)benzyl)pyrrolidin-3-ol C1b: $^1$H-NMR (400 MHz, DMSO-d$_6$) δ=7.57 (m, 2H), 7.45 (m, 2H), 4.35 (m, 1H), 3.68 (s, 2H), 2.87 (td, J=8.6, 5.0 Hz, 1H), 2.67 (m, 1H), 2.54 (dd, J=10.0, 5.1 Hz, 1H), 2.31 (td, J=8.9, 6.2 Hz, 1H), 2.20 (m, 1H), 1.76 (m, 1H); MS calcd. for C$_{12}$H$_{15}$F$_3$NOS ([M+H]$^+$): 246.1, found: 246.1.

Step B: To a solution of triphenylphosphine (39 mg, 0.15 mmol) in tetrahydrofurane (0.5 mL) is added diisopropyl azidocarboxylate (108 µL, 0.105 mmol). The reaction mixture is cooled to 0° C. and solution of Intermediates A5e (29 mg, 0.1 mmol) and Intermediate C1b (32 mg, 0.13 mmol) in tetrahydrofurane (0.5 mL) is added. The bath is removed and the mixture is stirred at room temperature overnight. The mixture is concentrated and the crude material is purified by flash chromatography (hexanes/ethyl acetate gradient) to afford the title compound (Example C1) as a white solid: $^1$H-NMR (400 MHz, DMSO-d$_6$) δ=7.57 (m, 2H), 7.48 (m, 2H), 6.73 (m, 2H), 4.82 (m, 1H), 3.93 (m, 2H), 3.78 (d, J=13.5 Hz, 1H), 3.71 (d, J=13.5 Hz, 1H), 2.81-2.89 (m, 6H), 2.74 (m, 2H), 2.49-2.60 (m, 2H), 2.07-2.22 (m, 2H), 1.93 (m, 2H), 1.74 (m, 2H); MS calcd. for C$_{24}$H$_{28}$F$_5$N$_2$O$_3$S ([M+H]$^+$): 519.2, found: 519.2.

By repeating the procedure described in the above Example C1 using appropriate starting materials, the following compounds, of table 3, are obtained. The Mitsunobu coupling (Step B), Example C3 is carried out in toluene at 95° C.

TABLE 3
| Example # | Structure | NMR and/or ESMS |
|---|---|---|
| C2 | 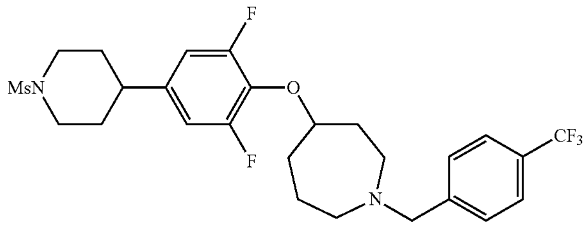 | $^1$H NMR (400 MHz, CDCl$_3$) δ = 7.56 (m, 2H), 7.46 (m, 2H), 6.73 (m, 2H), 4.39 (m, 1H), 3.93 (m, 2H), 3.67 (s, 2H), 2.71-2.82 (m, 6H), 2.66 (m, 2H), 2.53 (m, 2H), 1.83-2.12 (m, 8H), 1.75 (m, 2H); MS calcd. for C$_{26}$H$_{32}$F$_5$N$_2$O$_3$S ([M + H]$^+$): 547.2, found: 547.2. |
| C3 | 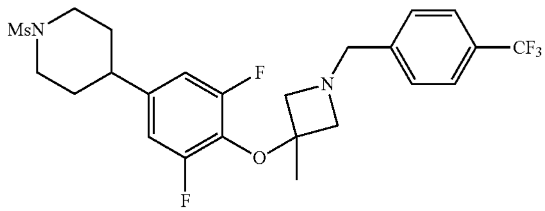 | $^1$H NMR (400 MHz, DMSO-d$_6$) δ = 7.66 (m, 2H), 7.48 (m, 2H), 7.12 (m, 2H), 3.65 (m, 4H), 3.32 (m, 2H), 3.17 (m, 2H), 2.89 (s, 3H), 2.77 (m, 2H), 2.64 (m, 1H), 1.86 (m, 2H), 1.65 (m, 2H), 1.49 (s, 3H); MS calcd. for C$_{24}$H$_{28}$F$_5$N$_2$O$_4$S ([M + H]$^+$): 519.2, found: 519.1. |
Example D1
5-((4-(2,6-difluoro-4-(4-fluoro-1-(methylsulfonyl)piperidin-4-yl)phenoxy)piperidin-1-yl)methyl)-3-(trifluoromethyl)-1,2,4-oxadiazole
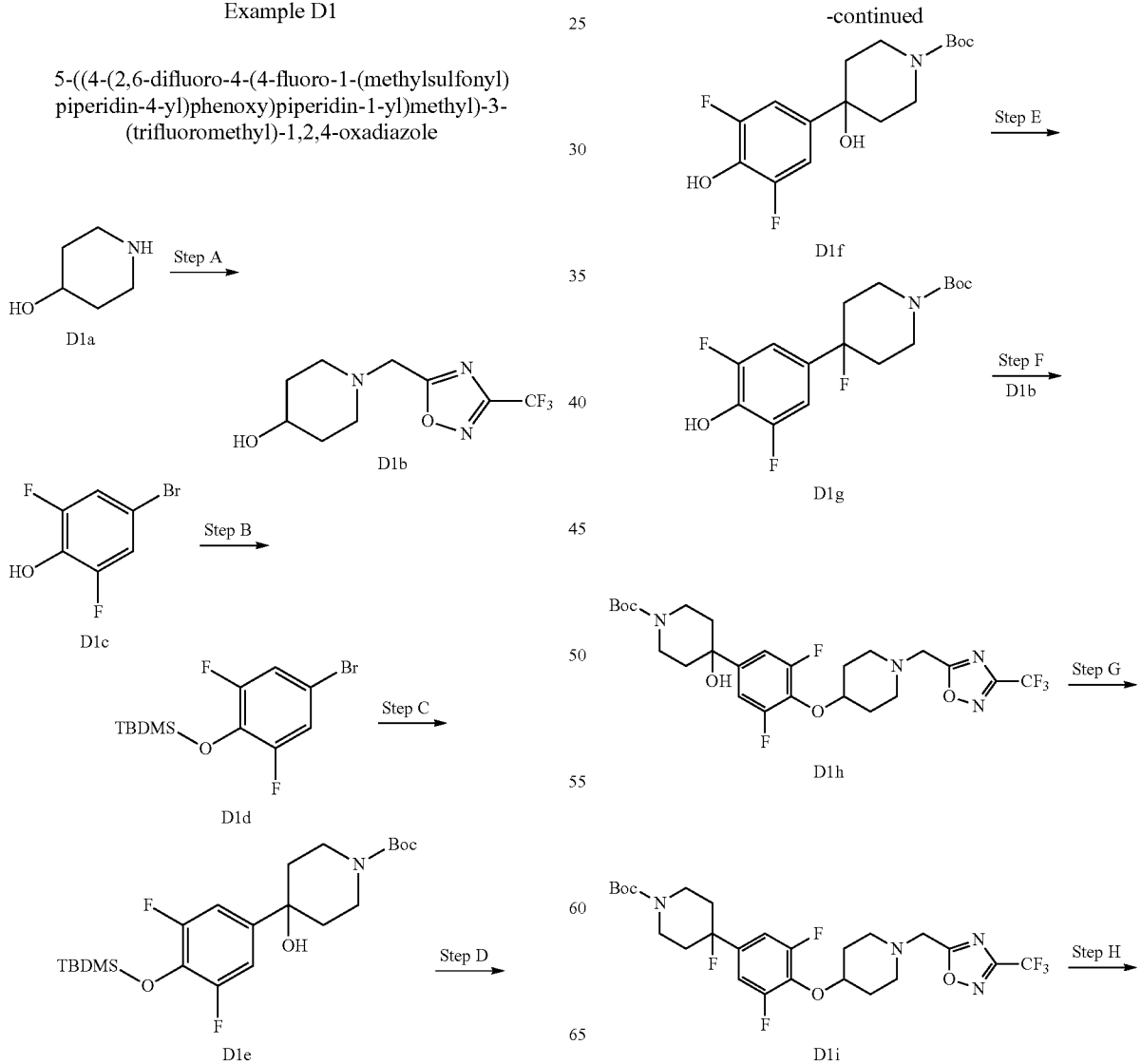

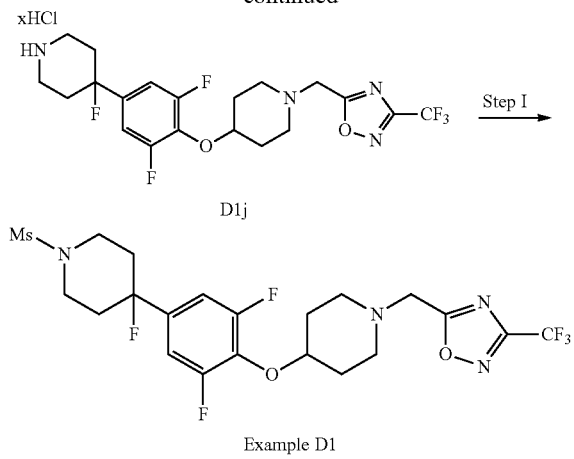

D1j

Example D1

Step A: A solution of 4-hydroxypiperidine D1a (50 mg, 0.5 mmol) in dichloromethane (15 mL) is treated with 5-(chloromethyl)-3-(trifluoromethyl)-1,2,4-oxadiazole (70 mg, 0.4 mmol, obtained following literature procedure: Go, Atsushi; Usui, Yoshihiro; Ikeda, Kaoru; Endo, Keiji (1985), JP 60149573 A) and diisopropylethylamine (0.11 mL, 1.2 mmol). The mixture is stirred overnight at room temperature, washed with water and saturated aqueous NaHCO$_3$, dried over Na$_2$SO$_4$ and concentration in vacuo to afford 1-(3-(Trifluoromethyl)-1,2,4-oxadiazol-5-yl)methyl)piperidin-4-ol D1b as an oil: $^1$H-NMR (400 MHz, CDCl$_3$) δ=5.25-5.19 (m, 1H), 4.30 (ddd, J=10.4, 6.4, 1.2 Hz, 2H), 4.12 (ddd, J=10.4, 4.0, 1.2 Hz, 2H), 3.09 (s, 3H), 1.46 (s, 9H); LCMS calcd. for C$_9$H$_{13}$F$_3$N$_3$O$_2^+$ ([M+H]$^+$): 252.1, found: 252.1. The product is used without purification.

Step B: 4-Bromo-2,6-difluorophenol D1c (5.0 g, 24 mmol) is dissolved in dichloromethane (50 mL) and treated with imidazole (2.28 g, 33.5 mmol). The colorless solution is treated in portions, with stirring, with tert-butylchlorodimethylsilane (4 g, 26 mmol). The mixture is stirred at room temperature overnight. The mixture is diluted with water (150 mL) and extracted with dichloromethane. The organic phase is washed with sat. NH$_4$Cl solution, dried over Na$_2$SO$_4$ and concentrated in vacuo. Purification of the crude material by flash chromatography (hexanes/ethyl acetate gradient) affords (4-bromo-2,6-difluorophenoxy)(tert-butyl)dimethylsilane D1d as a clear oil. $^1$H-NMR (400 MHz, CDCl$_3$) δ=7.05 (d, J=7.2 Hz, 2H), 1.00 (s, 9H), 0.19 (s, 6H); no MS spectrum could be obtained.

Step C: 4-Bromo-2,6-difluorophenoxy)(tert-butyl)dimethylsilane D1d (1.0 g, 3.1 mmol) is dissolved under nitrogen in dry tetrahydrofuran (30 mL). The solution is cooled to −78° C. and treated with n-butyllithium (2.6 M solution in toluene; 1.44 mL, 3.7 mmol). The mixture is stirred at −78° C. for 15 min and at 0° C. for 30 min. The mixture is cooled again to −78° C. and treated with a solution of tert-butyl 4-oxopiperidine-1-carboxylate (0.68 g, 3.4 mmol) in 10 mL dry tetrahydrofuran. The mixture is stirred at −78° C. for 10 min and at room temperature for 30 min. The mixture is diluted with sat. aqueous NH$_4$Cl (15 mL) and extracted with EtOAc (2×). The combined organic phase is washed with brine, dried over Na$_2$SO$_4$ and concentrated in vacuo. The crude material is purified by flash chromatography (hexanes/ethyl acetate gradient) to afford tert-butyl 4-(4-(((tert-butyldimethylsilyl)oxy)-3,5-difluorophenyl)-4-hydroxypiperidine-1-carboxylate D1e as a colorless oil. $^1$H-NMR (400 MHz, CDCl$_3$) δ=6.97 (d, J=7.2 Hz, 2H), 4.03 (br. s, 2H), 3.19 (br. t, J=11 Hz, 2H), 1.90 (br. t, J=11 Hz, 2H), 1.68 (d, J=12.5 Hz, 2H), 1.58 (s, 1H), 1.48 (s, 9H), 1.01 (s, 9H), 0.19 (s, 6H); $^{19}$F-NMR (376 MHz, CDCl$_3$) δ=−127.94; LCMS calcd. for C$_{22}$H$_{36}$F$_2$NO$_4$Si$^+$ ([M+H]$^+$): 444.1, found: 443.9.

Step D: A solution of tert-butyl 4-(4-(((tert-butyldimethylsilyl)oxy)-3,5-difluorophenyl)-4-hydroxypiperidine-1-carboxylate D1e (1.0 g, 2.25 mmol) in tetrahydrofuran (10 mL) is treated with a solution of tetra-n-butylammonium fluoride in tetrahydrofuran (1.0 M; 3 mL, 1.33 mmol). The mixture is stirred at room temperature for 4 hours. Concentration and purification by flash chromatography (hexanes/ethyl acetate gradient) affords tert-butyl 4-(3,5-difluoro-4-hydroxyphenyl)-4-hydroxypiperidine-1-carboxylate D1f as an oil. $^1$H-NMR (400 MHz, CDCl$_3$) δ=7.01 (d, J=7.2 Hz, 2H), 4.03 (br. s, 2H), 3.19 (br. t, J=11 Hz, 2H), 1.89 (br. t, J=11 Hz, 2H), 1.67 (d, J=12.5 Hz, 2H), 1.58 (s, 1H), 1.48 (s, 9H); $^{19}$F-NMR (376 MHz, CDCl$_3$) δ=−134.41. No MS spectrum could be obtained.

Step E: In a plastic container, a solution of tert-butyl 4-(3,5-difluoro-4-hydroxyphenyl)-4-hydroxypiperidine-1-carboxylate D1f (0.4 g, 1.2 mmol) in dichloromethane (10 mL) is treated with DAST (0.31 mL, 2.4 mmol) at room temperature. The mixture is stirred for 30 min and treated with sat. aqueous NH$_4$Cl (3 mL). The mixture is extracted with dichloromethane, washed with sat. aqueous NaHCO$_3$, dried over Na$_2$SO$_4$ and concentrated in vacuo to yield tert-butyl 4-(3,5-difluoro-4-hydroxyphenyl)-4-fluoropiperidine-1-carboxylate D1g as an oil. $^1$H-NMR (400 MHz, CDCl$_3$) δ=7.01 (d, J=7.2 Hz, 2H), 4.03 (br. s, 2H), 3.19 (br. s, 2H), 1.88 td, J=13.3, 4.8 Hz, 2H), 1.66 (dq, J=14.1, 2.2 Hz, 2H), 1.47 (s, 9H); $^{19}$F-NMR (376 MHz, CDCl$_3$) δ=−134.1 (2F), −161.9 (1F). LCMS calcd. for C$_{16}$H$_{21}$F$_3$NO$_3^+$ ([M+H]$^+$): 332.1, found: 331.8. The product is used without purification.

Step F: tert-Butyl 4-(3,5-difluoro-4-hydroxyphenyl)-4-fluoropiperidine-1-carboxylate D1g in dichloromethane (1 mL) is added to a mixture of triphenylphosphine (48 mg, 0.2 mmol) and diethyl azodicarboxylate (30 mg, 0.2 mmol) in dichloromethane (2 mL), followed by 1-((3-(trifluoromethyl)-1,2,4-oxadiazol-5-yl)methyl)piperidin-4-ol D1b (40 mg, 0.15 mmol). The mixture is stirred at room temperature overnight. Concentration and flash chromatography purification (hexanes/ethyl acetate gradient) yields tert-butyl 4-(3,5-difluoro-4-((1-((3-(trifluoromethyl)-1,2,4-oxadiazol-5-yl)methyl)piperidin-4-yl)oxy)phenyl)-4-hydroxypiperidine-1-carboxylate D1h as an oil. $^{19}$F-NMR (376 MHz, CDCl$_3$) δ=−65.96 (3F), −126.00 (2F). LCMS calcd. for C$_{25}$H$_{32}$F$_5$N$_4$O$_5^+$ ([M+H]$^+$): 563.2, found: 562.7.

Step G: Using the same procedure as in Step E above starting from Intermediate D1h, tert-butyl 4-(3,5-difluoro-4-((1-((3-(trifluoromethyl)-1,2,4-oxadiazol-5-yl)methyl)piperidin-4-yl)oxy)phenyl)-4-fluoropiperidine-1-carboxylate D1i is obtained as a clear oil. LCMS calcd. for C$_{25}$H$_{31}$F$_6$N$_4$O$_4^+$ ([M+H]$^+$): 565.2, found: 565.2.

Step H: A solution of tert-butyl 4-(3,5-difluoro-4-((1-((3-(trifluoromethyl)-1,2,4-oxadiazol-5-yl)methyl)piperidin-4-yl)oxy)phenyl)-4-fluoropiperidine-1-carboxylate D1i in dichloromethane (5 mL) is treated with hydrogen chloride in dioxane (4 M solution; 0.1 mL, 0.4 mL). The mixture is stirred at room temperature for 1 hour and concentrated to yield 5-((4-(2,6-difluoro-4-(4-fluoropiperidin-4-yl)phenoxy)piperidin-1-yl)methyl)-3-(trifluoromethyl)-1,2,4-oxadiazole D1j (hydrochloride salt) as an oil. LCMS calcd. for C$_{20}$H$_{23}$F$_6$N$_4$O$_2^+$ ([M+H]$^+$): 465.2, found: 465.2.

Step I: A solution of 5-((4-(2,6-difluoro-4-(4-fluoropiperidin-4-yl)phenoxy)piperidin-1-yl)methyl)-3-(trifluoromethyl)-1,2,4-oxadiazole D1j (hydrochloride salt) in dichloromethane (5 mL) at 0° C. is treated with ethyl diisopropylamine (0.03 mL, 0.3 mmol) and solid methanesulfonic anhydride (20 mg, 0.1 mmol). After 1 hour, the mixture is treated at 0° C. with sat. NaHCO$_3$ and extracted with dichloromethane. The organic phase is dried over Na$_2$SO$_4$ and concentrated in vacuo. Purification of the crude material by reversed-phase HPLC (acetonitrile/water gradient) affords the title compound (Example D1): $^1$H-NMR (400 MHz, CD$_3$CN) δ=6.90 (d, J=9.6 Hz, 2H), 4.04 (septet, J=4.0 Hz, 1H), 3.79 (s, 2H), 3.52-3.47 (m, 2H), 2.69-2.40 (m, 2H), 2.64 (s, 3H), 2.29-2.23 (m, 2H), 2.05-1.90 (m, 2H), 1.89-1.81 (m, 2H), 1.64-1.56 (m, 2H), 1.10-0.97 (m, 2H); $^{19}$F-NMR (376 MHz, CD$_3$CN) δ=−67.09 (3F), −127.52 (2F), −160.74 (1F). LCMS calcd. for C$_{21}$H$_{25}$F$_6$N$_4$O$_4$S$^+$ ([M+H]$^+$): 543.2, found: 543.2.

Biological Assays

Generation of Stable Cell Line

Flp-In-CHO cells (Invitrogen, Cat. #R758-07) are maintained in Ham's F12 medium supplemented with 10% fetal bovine serum, 1% antibiotic mixture and 2 mM L-glutamine. The cells are transfected with a DNA mixture containing human GPR119 in pcDNA5/FRT vector and the pOG44 vector (1:9) using Fugene6 (Roche), according to the manufacturer's instruction. After 48 hours, the medium is changed to medium supplemented with 400 μg/ml hygromycin B to initiate the selection of stably transfected cells.

Cyclic AMP Assay in Stable Cell Line

To test the activity of compounds of the invention, Flp-In-CHO-hGPR119 cells are harvested and resuspended in DMEM plus 3% lipid-depleted fetal bovine serum. Forth μl of cells are plated in 384 well plates at a density of 15,000 cells/well. IBMX (3-isobutyl-1-methyl-xanthine) is added to the cells to a final concentration of 1 mM, followed by the addition of 500 nl of the compound to be tested. The cells are incubated at 37° C. for 30 minutes. Equal volume (20 μl) of the HTRF reagents, anti-cAMP-Cryptate and cAMP-XL665, are added to the cells. The plates are incubated at room temperature for 1 hour and read on a HTRF reader according to the manufacturer's instruction.

Compounds of Formula I, in free form or in pharmaceutically acceptable salt form, produced a concentration-dependent increase in intracellular cAMP level. Compound of the invention show an EC$_{50}$ of between $1\times10^{-5}$ and $1\times10^{-10}$M, preferably less than 500 nM, more preferably less than 100 nM.

For example, compounds of the invention show EC$_{50}$s according to the following table:

| Example Number | hGPR119 EC$_{50}$ (nM) |
|---|---|
| A1 | 118 |
| A2 | 979 |
| A3 | 20 |
| A4 | 12 |
| A5 | 9 |
| A6 | 69 |
| A7 | 13 |
| A8 | 70 |
| A9 | 38 |
| A10 | 666 |
| A11 | 22 |
| A12 | 341 |
| A13 | 237 |
| A14 | 238 |
| A15 | 134 |
| A16 | 884 |
| A17 | 26 |
| A18 | 11 |
| A19 | 12 |
| A20 | 9 |
| A21 | 39 |
| A22 | 116 |
| A23 | 12 |
| A24 | 177 |
| A25 | 246 |
| A26 | 330 |
| A27 | 764 |
| A28 | 49 |
| A29 | 1090 |
| A30 | 135 |
| A31 | 652 |
| A32 | 145 |
| A33 | 331 |
| A34 | 12 |
| A35 | 688 |
| A36 | 28 |
| A37 | 325 |
| A38 | 458 |
| A39 | 214 |
| A40 | 576 |
| A41 | 36 |
| A42 | 149 |
| A43 | 115 |
| A44 | 38 |
| A45 | 48 |
| B1 | 7 |
| B2 | 28 |
| B3 | 16 |
| B4 | 757 |
| B5 | 49 |
| B6 | 37 |
| B7 | 16 |
| B8 | 286 |
| B9 | 76 |
| B10 | 131 |
| B11 | 397 |
| B12 | 55 |
| B13 | 108 |
| B14 | 70 |
| B15 | 97 |
| B16 | 9 |
| B17 | 74 |
| B18 | 52 |
| B19 | 448 |
| B20 | 208 |
| B21 | 244 |
| B22 | 443 |
| B23 | 210 |
| B24 | 6 |
| B25 | 442 |
| B26 | 37 |
| B27 | 11 |
| B28 | 5 |
| B29 | 50 |
| B30 | 78 |
| C1 | 144 |
| C2 | 125 |
| C3 | 644 |
| D1 | 199 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

We claim:
1. A compound selected from Formula I:

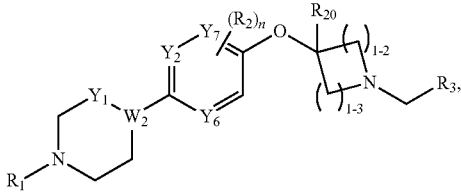

or the pharmaceutically acceptable salts thereof;
in which:
n is selected from 0, 1, and 2;
$R_1$ is selected from —S(O)$_2$X$_2$R$_{4a}$ —C(O)OX$_2$R$_{4a}$ and —C(O)X$_2$R$_{4a}$, X$_2$OR$_{4a}$;
wherein
$X_2$ is selected from a bond and $C_{1-4}$ alkylene;
$R_{4a}$ is selected from hydrogen, $C_{1-6}$alkyl, halo-substituted-$C_{1-6}$alkyl, hydroxy-substituted-$C_{1-6}$alkyl, phenyl, and, $C_{3-8}$heterocycloalkyl; wherein said heterocycloalkyl of $R_{4a}$ is optionally substituted with $C_{1-6}$alkyl or —C(O)OX$_4$R$_{5c}$; wherein $X_4$ is $C_{1-4}$alkylene; $R_{5c}$ is $C_{1-6}$alkyl;
$R_2$ is halo
$R_{20}$ is selected from hydrogen and methyl;
$W_2$ is selected from CR$_7$ and N; wherein R$_7$ is selected from hydrogen and halo;
$Y_1$ is selected from CH$_2$ and C(O); or $Y_1$ and $W_2$ taken together can form a double bond where $W_2$ is C and $Y_1$ is CH;
$Y_2$, $Y_6$ and $Y_7$ are independently selected from N and CH, where at least one of $Y_2$, $Y_6$ and $Y_7$ is CH;
$Y_5$ is —CH$_2$—;
$R_3$ is selected from $C_{6-10}$aryl and 5-6 membered heteroaryl; wherein said aryl or heteroaryl of $R_3$ is optionally substituted with 1 to 4 $R_{14}$ radicals; wherein each $R_{14}$ is independently selected from $C_{1-6}$alkyl, halo, $C_{1-6}$alkoxy, halo-substituted-$C_{1-6}$alkyl, halo-substituted-$C_{1-6}$alkoxy, and $C_{1-10}$ heterocycloalkyl; wherein the heterocycloalkyl of $R_{14}$ is optionally substituted by halo.
2. The compound of claim 1 of Formula Ia:

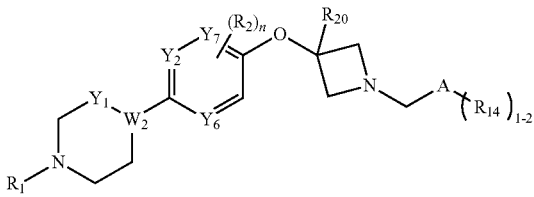

in which:
A is selected from phenyl and a 5-6 membered heteroaryl;
$R_1$ is selected from S(O)$_2$R$_{4a}$, —C(O)R$_{4a}$ and —C(O)OX$_2$R$_{4a}$; wherein $X_2$ is selected from a bond and $C_{1-4}$alkylene; $R_{4a}$ is selected from $C_{1-6}$alkyl, halo-substituted-$C_{1-6}$alkyl, and $C_{3-8}$heterocycloalkyl; wherein said $C_{3-8}$heterocycloalkyl of $R_{4a}$ is optionally substituted with $C_{1-6}$alkyl; and $R_{14}$ is selected from hydrogen, $C_{1-6}$alkyl, halo, cyano, $C_{1-6}$alkoxy, halo-substituted-$C_{1-6}$alkyl and halo-substituted-$C_{1-6}$alkoxy.
3. The compound of claim 2 in which:
A is selected from phenyl, pyridinyl, thiazolyl, 1H-1,2,4-triazole substituted with methyl, pyrimidinyl and naphthyl;
$R_1$ is selected from —S(O)$_2$R$_{4a}$, —C(O)R$_{4a}$ and —C(O)OX$_2$R$_{4a}$; wherein $X_2$ is selected from a bond and methylene; $R_{4a}$ is selected from methyl, trifluoromethyl, t-butyl, pyranyl, hydroxypropyl, propyl, piperidinyl substituted with t-butoxycarbonyl, pyrrolidinyl and phenyl; and
$W_2$ is selected from CH and N.
4. The compound of claim 3 in which:
$R_{14}$ is selected from hydrogen, halo, methyl, isopropyl, t-butyl, cyclopropyl, difluoroethyl, trifluoromethyl, trifluoromethoxy, methoxy, difluoromethoxy and fluorooxetanyl.
5. The compound of claim 1 selected from:
4-(methylsulfonyl)-1-(5-(1-(4(trifluoromethoxy)benzyl)azetidin-3-yloxy)pyrazin-2-yl)piperazin-2-one;
3-chloro-2-((3-(2,6-difluoro-4-(1(methylsulfonyl)piperidin-4-yl)phenoxy)azetidin-1-yl)methyl)-5(trifluoromethyl)pyridine;
2-((3-(2,6-difluoro-4-(1-(methylsulfonyl)piperidin-4-yl)phenoxy)azetidin-1-yl)methyl)-5-(trifluoromethyl)pyrimidine;
4-(3,5-difluoro-4-(1-(4-(3-fluorooxetan-3yl)benzyl)azetidin-3-yloxy)phenyl)-1-(methylsulfonyl)piperidine;
4-(3,5-difluoro-4-(1-(naphthalen-2-ylmethyl)azetidin-3-yloxy)phenyl)-1-(methylsulfonyl)piperidine;
4-(3,5-difluoro-4-(1-(naphthalen-1-ylmethyl)azetidin-3-yloxy)phenyl)-1-(methylsulfonyl)piperidine;
1-(3,5-difluoro-4-(1-(4-(trifluoromethyl)benzyl)azetidin-3-yloxy)phenyl)-4-(methylsulfonyl)piperazine;
1-(3,5-difluoro-4-(1-(4-(trifluoromethyl)benzyl)azetidin-3-yloxy)phenyl)-4-(methylsulfonyl)piperazin-2-one;
4-(3,5-difluoro-4-(1-(4-(trifluoromethyl)benzyl)azetidin-3-yloxy)phenyl)-1-(methylsulfonyl)-1,2,3,6-tetrahydropyridine;
1-(4-(3,5-difluoro-4-(1-(4-trifluoromethyl)benzyl)azetidin-3-yloxy)phenyl)-5,6-dihydropyridin-1(2H)-yl)-2,2,2-trifluoroethanone;
4-(3,5-difluoro-4-(1-(4-(trifluoromethyl)benzyl)azetidin-3-yloxy)phenyl)-1-(tetrahydro-2H-pyran-4-ylsulfonyl)piperidine;
tert-butyl 4-(4-(3,5-difluoro-4-(1-(4-(trifluoromethyl)benzyl)azetidin-3-yloxy)phenyl)piperidin-1-ylsulfonyl)piperidine-1-carboxylate;
4-(3,5-difluoro-4-(1-(4-(trifluoromethyl)benzyl)azetidin-3-yloxy)phenyl)-1-(piperidin-4-ylsulfonyl)piperidine;
t-butyl 3-(4-(3,5-difluoro-4-(1-(4-(trifluoromethyl)benzyl)azetidin-3-yloxy)phenyl)piperidin-1-ylsulfonyl)pyrrolidine-1-carboxylate;
4-(3,5-difluoro-4-(1-(4-(trifluoromethyl)benzyl)azetidin-3-yloxy)phenyl)-1-(pyrrolidin-3-ylsulfonyl)piperidine;
3-(4-(3,5-difluoro-4-(1-(4-(trifluoromethyl)benzyl)azetidin-3-yloxy)phenyl)piperidin-1-ylsulfonyl)propan-1-ol;
2-(4-(methylsulfonyl)piperazin-1-yl)-5-(1-(4-(trifluoromethyl)benzyl)azetidin-3-yloxy)pyrimidine;
4-(3,5-difluoro-4-(3 -methyl-1-(4-(trifluoromethyl)benzyl)azetidin-3 -yloxy)phenyl)-1-(methylsulfonyl)piperidine;

3-((3 -(2,6-difluoro-4-(1-(methylsulfonyl)piperidin-4-yl)
phenoxy)azetidin- 1-yl)methyl)-5-(trifluoromethyl)-
1,2,4-oxadiazole;
1-(3-fluoro-4-(1-(4-(trifluoromethyl)benzyl)azetidin-3-
yloxy)phenyl)-4-(methylsulfonyl)piperazine;
3-tert-butyl-5-((3-(2,6-difluoro-4-(1-(methylsulfonyl)pip-
eridin-4-yl)phenoxy)azetidin-1-yl)methyl)-1,2,4-oxa-
diazole;
5-((3 -(2,6-difluoro-4-(1-(methylsulfonyl)piperidin-4-yl)
phenoxy)azetidin- 1-yl)methyl)-3-isopropyl-1,2,4-oxa-
diazole;
3-cyclopropyl-5-((3-(2,6-difluoro-4-(1-(methylsulfonyl)
piperidin-4-yl)phenoxy)azetidin-1-yl)methyl)-1,2,4-
oxadiazole;
3-((3-(2,6-difluoro-4-(1-(methylsulfonyl)piperidin-4-yl)
phenoxy)azetidin- 1-yl)methyl)-5-isopropyl-1,2,4-oxa-
diazole;
5-((3 -(2,6-difluoro-4-(1-(methylsulfonyl)piperidin-4-yl)
phenoxy)azetidin- 1-yl)methyl)-3 -(trifluoromethyl)-1,
2,4-oxadiazole;
5-((3 -(2,6-difluoro-4-(1-(methylsulfonyl)piperidin-4-yl)
phenoxy)azetidin- 1-yl)methyl)-3-(1,1-difluoroethyl)-
1,2,4-oxadiazole;
4-(3,5-difluoro-4-(1-((1-methyl-3-(trifluoromethyl)-1H-
pyrazol-5-yl)methyl)azetidin-3-yloxy)phenyl)-1-(me-
thylsulfonyl)piperidine;
2-((3-(2,6-difluoro-4-(1-(methylsulfonyl)piperidin-4-yl)
phenoxy)azetidin- 1-yl)methyl)-4-(trifluoromethyl)
thiazole;
4-((3 -(2,6-difluoro-4-(1-(methylsulfonyl)piperidin-4-yl)
phenoxy)azetidin- 1-yl)methyl)-2-(trifluoromethyl)
thiazole;
4-(3 ,5-difluoro-4-(1-((1-methyl-3 -(trifluoromethyl)- 1H-
1,2,4-triazol-5-yl)methyl)azetidin-3 -yloxy)phenyl)-1-
(methylsulfonyl)piperidine;
4-(propane- 1-sulfonyl)- 1-{5-[(1-{[4-(trifluoromethyl)
phenyl]methyl }azetidin-3-yl)oxy]pyridin-2-
yl}piperazin-2-one;
4-methanesulfonyl- 1-{5-[(1-{[4-(propan-2-yl)phenyl]
methyl}azetidin-3-yl)oxy]pyridin-2-yl}piperazin-2-
one;
4-methanesulfonyl- 1-{5-[(1-{[4-(propan-2-yl)phenyl]
methyl}azetidin-3-yl)oxy]pyrazin-2-yl}piperazin-2-
one;
4-methanesulfonyl- 1-{5-[(1-{[4-(trifluoromethyl)phe-
nyl]methyl}azetidin-3-yl)oxy]pyrazin-2-yl}piperazin-
2-one;
2-(4-methanesulfonylpiperazin- 1-yl)-5-[(1-{[4-(propan-
2-yl)phenyl]methyl}azetidin-3-yl)oxy]pyrazine;
4-methanesulfonyl-1-{5-[(1-{[4-(trifluoromethyl)phenyl]
methyl}azetidin-3 -yl)oxy]pyridin-2-yl}piperazin-2-
one;
1 -methanesulfonyl-4-{5-[(1-{[4-(trifluoromethyl)phe-
nyl]methyl}azetidin-3-yl)oxy]pyridin-2-yl}piperazine;
1 -(propane-1-sulfonyl)-4-{5-[(1-{[4-(trifluoromethyl)
phenyl]methyl }azetidin-3-yl)oxy]pyridin-2-
yl}piperazine;
2-(4-methanesulfonylpiperazin- 1 -yl)-5-[(1-{[4-(trifluo-
romethyl)phenyl]methyl }azetidin-3-yl)oxy]pyrazine;
1 -methanesulfonyl-4-{5-[(1-{[4-(trifluoromethoxy)phe-
nyl]methyl}azetidin-3-yl)oxy]pyridin-2-yl}piperazine;
1 -methanesulfonyl-4-{4-[(1-{[4-(propan-2-yl)phenyl]
methyl }azetidin-3 -yl)oxy]phenyl}piperazine;
1 -methanesulfonyl-4-{5-[(1-{[4-(propan-2-yl)phenyl]
methyl}azetidin-3-yl)oxy]pyridin-2-yl}piperazine;
1-[5-({1-[(4-chlorophenyl)methyl]azetidin-3-yl}oxy)
pyridin-2-yl]-4-methanesulfonylpiperazine;
1-{5-[(1-{[4-(difluoromethoxy)phenyl]methyl}azetidin-
3-yl)oxy]pyridin-2-yl}-4-methanesulfonylpiperazine;
1-methanesulfonyl-4-[5-({1-[(4-methylphenyl)methyl]
azetidin-3-yl }oxy)pyridin-2-yl]piperazine;
1-methanesulfonyl-4-[5-({1-[(4-methoxyphenyl)methyl]
azetidin-3-yl}oxy)pyridin-2-yl]piperazine;
benzyl 4-{5-[(1-{[4-(propan-2-yl)phenyl]methyl }azeti-
din-3-yl)oxy]pyrazin-2-yl }piperazine-1-carboxylate;
1-methanesulfonyl-4-{5-[(1-{[3-(trifluoromethyl)phenyl]
methyl }azetidin-3-yl)oxy]pyridin-2-yl}piperazine;
and
benzyl 3-oxo-4-{5-[(1-{[4-(propan-2-yl)phenyl]
methyl }azetidin-3-yl)oxy]pyridin-2-yl}piperazine-1-
carboxylate.
6. The compound of claim 1 of Formula Ib:

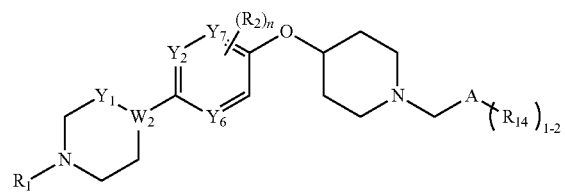

Ib in which:
A is selected from $C_{6-10}$aryl and a 5-6 membered het-
eroaryl;
$R_1$ is selected from $S(O)_2R_{4a}$ and —$C(O)OX_2R_{4a}$; wherein
$X_2$ is selected from a bond and $C_{1-4}$ alkylene; $R_{4a}$ is
selected from $C_{1-6}$alkyl and $C_{6-10}$aryl; and
$R_{14}$ is selected from $C_{1-6}$alkyl, halo, cyano, $C_{1-6}$alkoxy,
halo-substituted-$C_{1-6}$alkyl and halo-substituted-
$C_{1-6}$alkoxy.
7. The compound of claim 6 in which:
A is selected from phenyl, oxadiazolyl, 1H-1,2,4-triazol,
pyrazolyl and thiazolyl;
$R_1$ is selected from $S(O)_2R_{4a}$ and —$C(O)OX_2R_{4a}$; wherein
$X_2$ is methylene; $R_{4a}$ is selected from methyl, propyl and
phenyl; and
$W_2$ is selected from $CH_2$ and N;.
8. The compound of claim 7 in which:
$R_{14}$ is selected from methyl, halo, isopropyl, fluoroisopro-
pyl, t-butyl, cyclopropyl, difluoromethyl, difluoroethyl,
trifluoromethyl, trifluoromethoxy, methoxy and difluo-
romethoxy.
9. The compound of claim 1 selected from:
5-((4-(2,6-difluoro-4-(1-(methylsulfonyl)piperidin-4-yl)
phenoxy)piperidin-1-yl)methyl)-2-(trifluoromethyl)
pyridine;
4-(3,5-difluoro-4-(1-(3-(trifluoromethyl)benzyl)piperi-
din-4-yloxy)phenyl)-1-(methylsulfonyl)piperidine;
5-((4-(5-(4-(Methylsulfonyl)piperazin-1-yl)pyrazin-2-
yloxy)piperidin-1-yl)methyl)-3-(trifluoromethyl)-1,2,
4-oxadiazole;
5-((4-(2,6-difluoro-4-(4-fluoro-1-(methylsulfonyl)piperi-
din-4-yl)phenoxy) piperidin-1-yl)methyl)-3-(trifluo-
romethyl)-1,2,4-oxadiazole;
5-((4-(2,3-difluoro-4-(1-(methylsulfonyl)piperidin-4-yl)
phenoxy)piperidin-1-yl)methyl)-3-(trifluoromethyl)-1,
2,4-oxadiazole;
5-((4-(2,5-difluoro-4-(1-(methylsulfonyl)piperidin-4-yl)
phenoxy)piperidin-1-yl)methyl)-3-(trifluoromethyl)-1,
2,4-oxadiazole;

5-((4-(3,5-difluoro-4-(1-(methylsulfonyl)piperidin-4-yl) phenoxy)piperidin-1-yl)methyl)-3-(trifluoromethyl)-1, 2,4-oxadiazole;

5-((4-(2-fluoro-4-(1-(methylsulfonyl)piperidin-4-yl)phenoxy)piperidin-1-yl)methyl)-3-(trifluoromethyl)-1,2,4-oxadiazole;

5-((4-(3-fluoro-4-(1-(methylsulfonyl)piperidin-4-yl)phenoxy)piperidin-1-yl)methyl)-3-(trifluoromethyl)-1,2,4-oxadiazole;

4-(3,5-difluoro-4-(1-((1-methyl-3-(trifluoromethyl)-1H-pyrazol-5-yl)methyl)piperidin-4-yloxy)phenyl)-1-(methylsulfonyl)piperidine;

2-((4-(2,6-difluoro-4-(1-(methylsulfonyl)piperidin-4-yl) phenoxy)piperidin-1-yl)methyl)-4-(trifluoromethyl) thiazole;

4-((4-(2,6-difluoro-4-(1-(methylsulfonyl)piperidin-4-yl) phenoxy)piperidin-1-yl)methyl)-2-(trifluoromethyl) thiazole;

4-(3,5-difluoro-4-(1-((1-methyl-3-(trifluoromethyl)-1H-1,2,4-triazol-5-yl )methyl)piperidin-4-yloxy)phenyl)-1-(methylsulfonyl)piperidine;

3-((4-(2,6-difluoro-4-(1-(methylsulfonyl)piperidin-4-yl) phenoxy)piperidin-1-yl)methyl)-5-(trifluoromethyl)-1, 2,4-oxadiazole;

5-((4-(2,6-difluoro-4-(1-(methylsulfonyl)piperidin-4-yl) phenoxy)piperidin-1-yl)methyl)-3-isopropyl-1,2,4-oxadiazole;

2-((4-(5-(1-(methylsulfonyl)piperidin-4-yl)pyrazin-2-yloxy)piperidin-1-yl)methyl)-4-(trifluoromethyl)thiazole;

5-((4-(4-(1-(methylsulfonyl)piperidin-4-yl)phenoxy)piperidin-1-yl)methyl)-3-(trifluoromethyl)-1,2,4-oxadiazole;

4-(3,5-difluoro-4-((1-(4-trifluoromethyl)benzyl)piperidin-4-yl)oxy)phenyl)-1-(methylsulfonyl)piperidine;

5-((4-(2,6-Difluoro-4-(1-(methylsulfonyl)piperidin-4-yl) phenoxy)piperidin-1-yl)methyl)-3-(trifluoromethyl)-1, 2,4-oxadiazole;

5-((4-(2,6-difluoro-4-(1-(methylsulfonyl)piperidin-4-yl) phenoxy)piperidin-1-yl)methyl)-3-(1,1-difluoroethyl)-1,2,4-oxadiazole;

5-((4-(2,6-difluoro-4-(1-(methylsulfonyl)piperidin-4-yl) phenoxy)piperidin-1-yl)methyl)-3-(difluoromethyl)-1, 2,4-oxadiazole;

5-((4-(2,6-difluoro-4-(1-(methylsulfonyl)piperidin-4-yl) phenoxy)piperidin-1-yl)methyl)-3-(2-fluoropropan-2-yl)-1,2,4-oxadiazole; and 4-(3,5-Difluoro-4-(1-(4-(trifluoromethyl)benzyl)pyrrolidin-3-yloxy)phenyl)-1-(methylsulfonyl)piperidine.

10. A pharmaceutical composition comprising a therapeutically effective amount of a compound of any one of claim 1 in combination with a pharmaceutically acceptable excipient.

11. A compound selected from the group consisting of:

4-{3,5-difluoro-4-[(1-{1-[4-(trifluoromethyl)phenyl] ethyl }azetidin-3-yl)oxy]phenyl }-1-methanesulfonylpiperidine;

4-{3,5-difluoro-4-[(1-{1-[4-(trifluoromethyl)phenyl]propan-2-yl}azetidin-3-yl)oxy]phenyl }-1-methanesulfonylpiperidine;

4-(3,5-difluoro-4-(1-(1-(4-(trifluoromethyl)phenyl)propyl)azetidin-3-yloxy)phenyl)-1-(methylsulfonyl)piperidine;

2-(3-(2,6-difluoro-4-(1-(methylsulfonyl)piperidin-4-yl) phenoxy)azetidin-1-yl)-2-(4-(trifluoromethyl)phenyl) ethanol;

5-(1-(4-(2,6-difluoro-4-(1-(methylsulfonyl)piperidin-4-yl)phenoxy)piperidin-1-yl)ethyl)-3-(trifluoromethyl)-1,2,4-oxadiazole; and 4-(2,6-difluoro-4-(1-(methylsulfonyl)piperidin-4yl)phenoxy)-1-(4-(trifluoromethyl)benzyl)azepane.

12. A method for treating a disease or condition, wherein modulation of GPR119 activity can inhibit or ameliorate the pathology and/or symptomology of the disease or condition, comprising administering to a subject in need thereof a therapeutically effective amount of a compound as described in any one of claims 1 to 9 or a pharmaceutically acceptable salts or a pharmaceutical compositions thereof, wherein the disease or condition is selected from the group consisting of obesity, type 1 diabetes, type 2 diabetes mellitus, hyperlipidemia, idiopathic type 1 diabetes, latent autoimmune diabetes in adults, early-onset type 2 diabetes, youth-onset atypical diabetes, maturity onset diabetes of the young, malnutrition-related diabetes and gestational diabetes.

13. A method for treating a disease or condition, wherein modulation of GPR119 activity can inhibit or ameliorate the pathology and/or symptomology of the disease or condition, comprising administering to a subject in need thereof a therapeutically effective amount of a compound as described in any one of claims 1 to 9, or a pharmaceutically acceptable salt or a pharmaceutical composition thereof, wherein said disease or condition is selected from coronary heart disease, ischemic stroke, restenosis after angioplasty, peripheral vascular disease, intermittent claudication, myocardial infarction, dyslipidemia, post-prandial lipemia, conditions of impaired glucose tolerance, conditions of impaired fasting plasma glucose, metabolic acidosis, ketosis, arthritis, osteoporosis, hypertension, congestive heart failure, left ventricular hypertrophy, peripheral arterial disease, diabetic retinopathy, macular degeneration, cataract, diabetic nephropathy, glomerulosclerosis, chronic renal failure, diabetic neuropathy, metabolic syndrome, syndrome X, premenstrual syndrome, coronary heart disease, angina pectoris, thrombosis, atherosclerosis, myocardial infarction, transient ischemic attacks, stroke, vascular restenosis, hyperglycemia, hyperinsulinemia, hyperlipidemia, hypertrygliceridemia, insulin resistance, impaired glucose metabolism, conditions of impaired glucose tolerance, conditions of impaired fasting plasma glucose, obesity, erectile dysfunction, skin and connective tissue disorders, foot ulcerations and ulcerative colitis, endothelial dysfunction and impaired vascular compliance.

* * * * *